US009382328B2

(12) United States Patent
Jure-Kunkel et al.

(10) Patent No.: US 9,382,328 B2
(45) Date of Patent: *Jul. 5, 2016

(54) FULLY HUMAN ANTIBODIES AGAINST HUMAN 4-1BB

(71) Applicant: BRISTOL-MYERS SQUIBB COMPANY, Princeton, NJ (US)

(72) Inventors: Maria Jure-Kunkel, Plainsboro, NJ (US); Laura J. Hefta, Pennington, NJ (US); Marc Santoro, Yardley, PA (US); Subinay Ganguly, Newtown, PA (US); Edward L. Halk, Sunnyvale, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 122 days.

This patent is subject to a terminal disclaimer.

(21) Appl. No.: 14/211,438

(22) Filed: Mar. 14, 2014

(65) Prior Publication Data

US 2014/0193422 A1 Jul. 10, 2014

Related U.S. Application Data

(60) Continuation of application No. 13/368,710, filed on Feb. 8, 2012, now Pat. No. 8,716,452, which is a continuation of application No. 12/653,137, filed on Dec. 9, 2009, now Pat. No. 8,137,667, which is a continuation of application No. 11/903,106, filed on Sep. 20, 2007, now Pat. No. 7,659,384, which is a division of application No. 10/961,567, filed on Oct. 8, 2004, now Pat. No. 7,288,638.

(60) Provisional application No. 60/510,193, filed on Oct. 10, 2003.

(51) Int. Cl.
| *C07K 16/28* | (2006.01) |
| *A61K 39/395* | (2006.01) |
| *C07K 16/30* | (2006.01) |
| *A61K 39/00* | (2006.01) |
| *A61K 39/12* | (2006.01) |
| *A61K 39/39* | (2006.01) |

(52) U.S. Cl.
CPC ............ *C07K 16/30* (2013.01); *A61K 39/0011* (2013.01); *A61K 39/12* (2013.01); *A61K 39/39* (2013.01); *C07K 16/2878* (2013.01); *A61K 2039/505* (2013.01); *A61K 2039/53* (2013.01); *A61K 2039/55516* (2013.01); *C07K 2317/21* (2013.01); *C07K 2317/565* (2013.01); *C07K 2317/75* (2013.01); *C12N 2740/15034* (2013.01)

(58) Field of Classification Search
None
See application file for complete search history.

(56) References Cited

U.S. PATENT DOCUMENTS

| 6,458,934 B1 | 10/2002 | Hong et al. | |
| 6,569,997 B1 | 5/2003 | Kwon | |
| 7,288,638 B2 | 10/2007 | Jure-Kunkel et al. | |
| 7,659,384 B2 * | 2/2010 | Jure-Kunkel | A61K 39/011 435/252.3 |
| 8,137,667 B2 | 3/2012 | Jure-Kunkel et al. | |
| 8,716,452 B2 * | 5/2014 | Jure-Kunkel | A61K 39/0011 424/141.1 |

FOREIGN PATENT DOCUMENTS

| CA | 2108401 | 3/1995 |
| WO | WO 94/26290 | 11/1994 |
| WO | WO 95/07984 | 3/1995 |
| WO | WO 96/32495 | 1/1996 |
| WO | WO 96/29348 | 9/1996 |
| WO | WO 97/33898 | 9/1997 |
| WO | WO 98/16249 | 4/1998 |
| WO | WO 99/36093 | 7/1999 |
| WO | WO 99/44629 | 9/1999 |
| WO | WO 00/29445 | 5/2000 |
| WO | WO 02/36141 | 5/2002 |
| WO | WO 03/006632 | 1/2003 |
| WO | WO 03/031474 | 4/2003 |
| WO | WO 03/049755 | 6/2003 |
| WO | WO 03/083069 | 10/2003 |
| WO | WO 03/084999 | 10/2003 |
| WO | WO 2004/006853 | 1/2004 |
| WO | WO 2004/010947 | 2/2004 |
| WO | WO 2004/019866 | 3/2004 |
| WO | WO 2004/055513 | 7/2004 |
| WO | WO 2004/093831 | 11/2004 |

OTHER PUBLICATIONS

Abbas, A., et al., Chapter 7: "T Lymphocyte Antigen Recognition and Activation", Cellular and Molecular Immunology 3rd ed., pp. 139-170 (1997).
Alderson, M.R., et al., "Molecular and biological characterization of human 4-1BB and its ligand", Eur. J. Immunol., vol. 24, pp. 2219-2227 (1994).
Angal, S., et al., Molecular Immunology, "A Single Amino Acid Substitution Abolishes the Heterogeneity of Chimeric Mouse/Human (IgG4) Antibody", vol. 30, No. 1, pp. 105-108 (1993).
Antonia, S. et al., "Current developments of Immunotherapy in the clinic", Current Opinion in Immunology, vol. 16, pp. 130-136 (2004).
Ashkenazi, A., "Targeting Death and Decoy Receptors of the Tumor-Necrosis Factor Superfamily", Nature, vol. 2, pp. 420-430 (2002).
Bansal-Pakala, P. et al., "Defective T Cell Priming Associated with Aging Can Be Rescued by Signaling Through 4-1BB (CD137)", The Journal of Immunology, vol. 169, pp. 5005-5009 (2002).
Bassi, P.F., "BCG (Bacillus of Calmette Guerin) therapy of high-risk superficial bladder cancer", Surgical Oncology, vol. 11, pp. 77-83, (2002).

(Continued)

*Primary Examiner* — Ilia Ouspenski
(74) *Attorney, Agent, or Firm* — Stephen C. D'Amico

(57) ABSTRACT

Fully human antibodies and antigen-binding portions thereof that bind to human 4-1BB and that allow binding of human 4-1BB to a human 4-1BB ligand. In one aspect, the antibody is an IgG4 antibody. Also provided is a method for treating a disease in a subject comprising administering a therapeutically effective amount of the antibody to said subject.

6 Claims, 34 Drawing Sheets

(56) References Cited

OTHER PUBLICATIONS

Bertley, F., et al., "Control of Simian/Human Immunodeficiency Virus Viremia and Disease Progression after IL-2-Augmented DNA-Modified Vaccinia Virus Ankara Nasal Vaccination in Nonhuman Primates", The Journal of Immunology, vol. 172, pp. 3745-3757, (2004).
Bu, Z., et al., "Enhanced cellular immune response against SIV Gag induced by immunization with DNA vaccines expressing assembly and release-defective SIV Gag proteins", Virology, vol. 309, pp. 272-281, (2003).
Chambers C. et al., "Co-Stimulation in T-Cell Responses", Current Opinion in Immunology, vol. 19, pp. 396-404 (1997).
Chothia, C., et al., "Canonical Structures for the Hypervariable Regions of Immunoglobulins", J. Mol. Biol., vol. 196, pp. 901-917 (1987).
Cooper, D., "4-1BB (CD137) controls the clonal expansion and survival of CD8 T cells in vivo but does not contribute to the development of cytotoxicity", Eur. J. Immunology, vol. 32, pp. 521-529 (2002).
DeBenedette, M. et al., "Costimulation of CD28 T Lymphocytes by 4-1BB Ligand", Journal of Immunology, vol. 158, pp. 551-559 (1997).
DeBenedette, M., et al., "Analysis of 4-1BB Ligand (4-1BBL)-Deficient Mice and of Mice Lacking Both 4-1BBL and CD28 Reveals a Role for 4-1BBL in Skin Allograft Rejection and in the Cytotoxic T Cell Response to Influenza Virus", pp. 4833-4841 (1999).
Dranoff, G., et al., "Vaccination with irradiated tumor cells engineered to secrete murine granulocyte-macrophage colony-stimulating factor stimulates potent, specific, and long-lasting anti-tumor immunity", Proc. Nat'l. Acad. Sci. USA, vol. 90, pp. 3539-3543, (1993).
Elder, D., "Tumor Progression,Early Diagnosis and Pregnosis of Melanoma", Acta Oncologica, vol. 38, pp. 535-547 (1999).
Fishman, M. et al., "Novel Therapies for High-Risk Superficial Bladder Cancer", Expert Opin. Investig. Drugs, vol. 11, pp. 77-83 (2002).
Foell, J., et al., "CD137-Mediated T Cell Co-Stimulation Terminates Existing Autoimmune Disease in SLE-Prone NZB/NZW F1 Mice", N.Y. Acad. Sci., vol. 987, pp. 230-235 (2003).
Foote, J. et al., "Antibody Framework Residues Affecting the Conformation of the Hypervariable Loops", J. Mol. Biol., vol. 224, pp. 487-499 (1992).
Futagawa, T., et al., "Expression and function of 4-1BB and 4-1BB ligand on murine dendritic cells", International Immunology, vol. 14, pp. 275-286, (2001).
Goodwin, R.G., et al., "Molecular cloning of a ligand for the inducible T cell gene 4-1BB: a member of an emerging family of cytokines with homology to tumor necrosis factor", Eur. J. Immunol., vol. 23, pp. 2631-2641 (1993).
Gramaglia, I. et al., "Co-stimulation of antigen-specific CD4 T cells by 4-1BB ligand", Eur. J. Immunol., vol. 30, pp. 293-402, (2000).
Guinn, B., et al., "4-1BBL Cooperates with B7-1 and B7-2 in Converting a B Cell Lymphoma Cell Line into a Long-Lasting Antitumor Vaccine", The American Association of Immunologists, vol. 162 pp. 5003-5010, (1999).
Hakim, F.T., et al., "Aging, Immunity and Cancer", Current Opinion in Immunology, vol. 16, pp. 151-156, (2004).
Halapi, E, "Oligoclonal T cells in human cancer", Medical Oncology, vol. 15, pp. 203-211, (1998).
Hong, H.J., "A Humanized Anti-4-1BB Monoclonal Antibody Suppresses Antigen-Induced Humoral Immune Response in Nonhuman Primates", Journal of Immunotherapy, vol. 23, pp. 613-621, (2000).
Hurtado, J.C., et al., "Potential Role of 4-1BB in T Cell Activation", Journal of Immunology, vol. 155, pp. 3360-3367 (1995).
Hurtado, J.C., et al., "Signals Through 4-1BB are Costimulatory to Previously Activated Splenic T Cells and Inhibit Activation-Induced Cell Death", The American Association of Immunologists, pp. 2600-2609 (1997).
Jaffee, E.M., et al., "Novel Allogeneic Granulocyte-Macrophage Colony-Stimulating Factor-Secreting Tumor Vaccine for Pancreatic Cancer: A Phase I Trial of Safety and Immune Activation", Journal of Clinical Oncology, vol. 19, No. 1, pp. 145-156 (2001).
Jones, P. et al., "Replacing the Complementary-Determining Regions in a Human Antibody With Those From a Mouse", Nature, vol. 321, pp. 522-525 (1986).
Ju., S., et al., "A Functional Anti-Human 4-1BB Ligand Monoclonal Antibody that Enhances Proliferation of Monocytes by Reverse Signaling of 4-1BBL", Hybridoma and Hybridomincs, vol. 22, No. 5, pp. 333-338, (2003).
Kearny, J. et al., "A New Mouse Myeloma Cell Line That has Lost Immunoglobulin Expression But Permits the Construction of Antibody Secreting Hybrid Cell Lines", Journal of Immunology, vol. 123, No. 4, pp. 1548-1550 (1979).
Kim, J.J. et al., "Engineering Enhancement of Immune Responses to DNA-based Vaccines in a Prostate Cancer Model in Rhesus Macaques through the Use of Cytokine Gene Adjuvants", Clinical Cancer Research, vol. 7, pp. 882s-889s, (2001).
Kim, J.J., "Induction of Immune responses and safety profiles in rhesus macaques immunized with a DNA vaccine expressing human prostate specific antigen", Oncogene, vol. 20, pp. 4497-4506, (2001).
Kim, J.A., et al., "Divergent Effects of 4-1BB Antibodies on Antitumor Immunity and on Tumor-reactive T-Cell Generation", Cancer Research, vol. 61, pp. 2031-2037, (2001).
Kim, N.W., et al., "Specific Association of Human Telomerase Activity with Immortal Cells and Cancer", Science, vol. 266, pp. 2011-2015 (1994).
Kim, Y. et al., "Human 4-1BB Regulates CD28 Co-Stimulation to Promote Th1 Cell Responses", Eur. J. Immnol., vol. 28, pp. 881-890 (1998).
Kwon, B.S., et al., "cDNA sequences of two Inducible T-cell genes", Proc. Natl. Acad. Sci. USA, pp. 1963-1967 (1989).
Kwon., B.S., et al., "Immune Responses in 4-1BB (CD137)-Deficient Mice", The Journal of Immunology, pp. 5483-5490 (2002).
Kwon, B. et al., "4-1BB: Still in the Midal of Darkness", Mol. Cells, vol. 10, No. 2, pp. 119-126 (2000).
Kwon, B., et al., "Involvement of tumor necrosis factor receptor superfamily (TNFRSF) members in the pathogenesis of inflammatory diseases", Experimental and Molecular Medicine, vol. 35, No. 1, pp. 8-16 (2003).
Kwon, E.D., et al.,"Elimination of residual metastatic prostate cancer after surgery and adjunctive cytotoxic T lymphocyte-associated antigen 4 (CTLA-4) blockade immunology", PNAS, vol. 96, pp. 15-74-15079 (1999).
Laderach, D., et al., "4-1BB co-stimulation enhances human CD8+ T cell priming by augmenting the proliferation and survival of effector CD8+ T Cells" International Immunology, vol. 14, No. 10, pp. 1155-1167 (2002).
Lane, R., "A Short-Duration Polyethylene Glycol Fusion Technique for Increasing Production of Monoclonal Antibody-Secreting Hybridomas", Journal of Immunological Methods, vol. 81, pp. 223-228 (1985).
Langstein, J., et al., "CD137 (ILA/4-Ibb), a Member of the TNF Receptor Family, Induces Monocyte Activation via Bidirectional Signaling", The Journal of Immunology, vol. 160, pp. 2488-2494 (1998).
Langstein, J., et al., "Identification of CD137 as a potent monocyte survival factor", J. Leukoc. Biol., vol. 65, pp. 829-833 (1999).
Lee, H., et al., "4-1BB Promotes the Survival of CD8+ T Lymphocytes by Increasing Expression of Bel-$X_L$ and Bfl-1" , The Journal of Immunology, vol. 169, pp. 4882-4888 (2002).
Lenschow, D. et al.,"CD28/B7 System of T Cell Costimulation", Annu. Rev. Imnnunol., vol. 14, pp. 233-258 (1996).
Lesk, A. et al., Chapter 1: "Antibody Structure and Structural Predictions Useful in Guiding Antibody Engineering", Antibody Engineering, A Practical Guide, pp. 1-38 (1992).
Letvin, N.L., et al., "Heterologous Envelope Immunogens Contribute to AIDS Vaccine Protection in Rhesus Monkeys", Journal of Virology, vol. 78, No. 14, pp. 7490-7497 (2004).
Lindstedt, M. et al., "Expression of CD137 (4-1BB) on Human Follicular Dendritic Cells", Scandinavian Journal of Immunology, vol. 57, pp. 305-310 (2003).

(56) References Cited

OTHER PUBLICATIONS

Loh, E. et al. "Polymerase Chain Reaction With Single-Sided Specificity: Analysis of T Cell Receptor δ Chain", Science, vol. 243, pp. 217-220 (1989).

Makitalo, B., et al., "Enhanced cellular immunity and systemic control of SHIV infection by combined parenteral and mucosal administration of a DNA prime MVA boost vaccine regimen", Journal of General Virology, vol. 85, pp. 2407-2419 (2004).

Martinet, O., et al., "T cell activation with systemic agonistic antibody versus local 4-1BB ligand gene delivery combined with interleukin-12 eradicate liver metastases of breast cancer", Gene Therapy, vol. 9, No. 12, pp. 786-792 (2002).

Maus, M., et al., "Ex vivo expansion of polyclonal and antigen-specific cytotoxic T lymphocytes by artificial APCs expressing ligands for the T-cell receptor, CD28 and 4-1BB", Nature Biotechnology, vol. 20, pp. 143-148 (2002).

Melero, I., et al., "Monoclonal antibodies against the 4-1BB T-cell activation molecule eradicate established tumors", Nature Medicine, vol. 3, No. 6, pp. 682-685 (1997).

Melero, I. et al., "NK1.1 Cells Express 4-1BB (CDw137) Costimulatory Molecule and Are Required for Tumor Immunity Elicited by Anti-4-1BB Monoclonal Antibodies", Cellular Immunology, vol. 190, pp. 167-172 (1998).

Miller, R.A., "Effect of aging on T lymphocyte activation", Vaccine, vol. 18, pp. 1654-1660 (2000).

Miller, R.A., "The Aging Immune System: Primer and Prospectus", Science, vol. 273, pp. 70-74 (1996).

Miller, R.E., et al., "4-1BB-Specific Monoclonal Antibody Promotes the Generation of Tumor-Specific Immune Responses by Direct Activation of CD8 T Cells in a CD40-Dependent Manner", The Journal of Immunology, vol. 169, pp. 1792-1800 (2002).

Mittler, R.S., et al., "Anti-4-1BB Monoclonal Antibodies Abrogate T Cell-dependent Humoral Immune Responses In Vivo through the Induction of Helper T Cell Anergy", J. Exp. Med., vol. 190, No. 10, pp. 1535-1540 (1999).

Mogi et al., "Tumor rejection by gene transfer of 4-1BB ligand into a $CD80^+$ murine squamous cell carcinoma and the requirements of co-stimulatory molecules on tumor and host cells", Immunology, vol. 101, pp. 541-547 (2000).

Mossman, S.F., et al., "Protective Immunity to SIV Challenge Elicited by Vaccination of Macaques with Multigenic DNA Vaccines Producing Virus-Like Particles", Aids Research and Human Retroviruses, vol. 20, No. 4, pp. 425-434 (2004).

Muthumani, K., et al., "A Gag-Pol/Env-Rev SIV239 DNA vaccine improves CD4 counts, and reduce viral loads after pathogenic intrarectal $SIV_{mac}251$ challenge in Rhesus Macaques", Vaccine, vol. 21, pp. 629-637, pp. 629-637.

Naito, Y., et al., "$CD8^+$ T Cells Infiltrated within Cancer Cell Nests as a Prognostic Favor in Human Colorectal Cancer", Cancer Research, vol. 58, pp. 3491-3494 (1998).

O'Neill, E., et al., "IL-12/GM-CSF Coadministration in an SIV DNA Prime/Protein Boost Protocol Enhances Gag-Specific T Cells But Not Virus-Specific Neutralizing Antibodies in Rhesus Macaques", Aids Research and Human Retroviruses, vol. 19, No. 10, pp. 883-890 (2003).

Pan, P. et al., "Regulation of Dendritic Cell Function by NK Cells: Mechanisms Underlying the Synergism in the Combination Therapy of IL-12 and 4-1BB Activation", The Journal of Immunology, vol. 172, pp. 4779-4789.

Patterson, L.J., et al., "Protection against Mucosal Simian Immunodeficiency Virus $SIV_{mac251}$ Challenge by Using Replicating Adenovirus-SIV Multigene Vaccine Priming and Subunit Boosting", Journal of Virology, vol. 78, No. 5, pp. 2212-2221(2004).

Pauly, S., et al., "CD137 is expressed by follicular dendritic cells and costimulates B lymphocyte activation in germinal centers", Journal of Leukocyte Biology, vol. 72, pp. 35-42 (2002).

Pavlenko, M., et al., "A phase I trial of DNA vaccination with a plasmid expressing prostate-specific antigen in patients with hormone-refractory prostate cancer", British Journal of Cancer, vol. 91, pp. 688-694 (2004).

Pollok, K. et al., "Inducible T Cell Antigen 4-1BB",The Journal of Immunology, vol. 150, No. 3, pp. 771-781 (1993).

Pollak, K. et al., "4-1BB T-Cell Antigen Binds to Malura B Cells and Macrophages and Costimulates Anti-μ-Primed Splenic B Cells", Eur. J. Immunol, vol. 24, pp. 367-374 (1994).

Resser, J., et al. "Immunotherapy of Head and Neck Cancer", Current Opinion in Oncology, vol. 10, pp. 226-232 (1998).

Resser, J. et al., "Immunotherapy of Head and Neck Cancer", Current Opinion in Oncology, vol. 10, pp. 226-232 (1998).

Rosenberg, S.A., "Interleukin-2 and the Development of Immunotherapy for the Treatment of Patients With Cancer", The Cancer Journal From Scientific American, vol. 6, pp. S2-S7 (2000).

Rosenberg, S.A., "The Identification of Cancer Antigens: Impact on the Development of Cancer Vaccines", The Cancer Journal, vol. 6, pp. S142-S144 (2000).

Rosenberg, S.A., et al., et al., "A New Era Cancer Immunotherapy Based on the Genes that Encode Cancer Antigens", Immunity, vol. 10, pp. 281-287 (1999).

Rosenberg, S.A., "Progress in human tumour immunology and immunotherapy", Nature, vol. 411, pp. 380-384 (2001).

Saiki, R. et al., "Primer-Directed Enzymatic Amplifications of DNS with a Thermostable DNA Polymerase", Science, vol. 239, pp. 487-491 (1987).

Salgia, R., et al., "Vaccination With Irradiated Antologous Tumor Cells Engineered to Secrete Granulocyte-Macrophage Colony-Stimulating Factor Augments Antitumor Immunity in Some Patients With Metastatic Non-Small-Cell Lung Carcinoma", Journal of Clinical Oncology, vol. 21, No. 4, pp. 624-630 (2003).

Salih, H.R., et al., "Constitutive Expression of Functional 4-1BB (CD137) Ligand on Carcinoma Cells", The Journal of Immunology, vol. 165, pp. 2903-2910 (2000).

Salih, H.R., et al., "Soluble CD137 (4-1BB) Ligand is Released Following Leukocyte Activation and is Found in Sera of Patients with Hematological Malignancies", The Journal of Immunology, vol. 167, pp. 4059-4066 (2001).

Schwarz, H., et al., "A receptor induced by lymphocyte activation (ILA): a new member of the human nerve-growth-factor/tumor-necrosis-factor receptor family", Gene, vol. 134, No. 2, pp. 295-298 (1993).

Seo, S.K. et al., "4-1BB-mediated immunotherapy of rheumatoid arthritis", Nature Medicine, vol. 10, No. 10, pp. 1088-1094 (2004).

Shuford, W.W., et al., "4-1BB Costimulatory Signals Preferentially Induce $CD8^+$ T Cell Proliferation and Lead to the Amplification In Vivo of Cytotoxic T Cell Responses", J. Ex. Med., vol. 186, No. 1, pp. 47-55 (1997).

Sun, Y. et al., "Costimulatory molecule-targeted antibody therapy of a spontaneous autoimmune disease", Nature Medicine, vol. 8, No. 12, pp. 1405-1413 (2002).

Suto, R., et al., "A Mechanism for the Specific Immunogenicity of Heat Shock Protein-Chaperoned Peptides", Science, vol. 269, pp. 1585-1588 (1995).

Takahashi, C., et al., "Cutting Edge: 4-1BB is a Bona Fide CD8 T Cell Survival Signal", The American Association of Immunologists, pp. 5037-5040 (1999).

Tamura, Y., et al., "Immunotherapy of Tumors with Autologous Tumor-Derived Heat Shock Protein Preparations", Science, vol. 278, pp. 117-120 (1997).

Tan, J.T., et al., "4-1BB Costimulation is Required for Protective Anti-Viral Immunity After Peptide Vaccination", The American Association of Immunologists, pp. 2320-2325 (2000).

van der Bruggen, P., et al., "Tumor-specific shared antigenic peptides recognized by human T cells", Immunological Reviews, vol. 188, pp. 51-64 (2002).

Vinay, D.S., et al., "Immunity in the absence of CD28 and CD137 (4-1BB) molecules", Immunology and Cell Biology, vol. 81, pp. 176-184 (2003).

Vinay, D.S., et al., "Role of 4-1BB in immune responses", Immunology, vol. 10, pp. 481-489, (1998).

Wan, Y. et al., "Expression of co-stimulator 4-1BB molecule in hepatocellular carcinoma and adjacent non-tumor liver tissue, and its possible role in tumor immunity", World J. Gastroenterol, vol. 10, No. 2, pp. 195-199 (2004).

(56) References Cited

OTHER PUBLICATIONS

Wen, T., et al., "4-1BB Ligand-Mediated Costimulation of Human T Cells Induces CD4 and CD8 T Cell Expansion, Cytokine Production, and the Development of Cytolytic Effector Function", Journal of Immunology, vol. 168, pp. 4897-4906 (2002).

Wilcox, R.A., et al., "Impaired Infiltration of Tumor-specific Cytolytic T Cells in the Absence of Interferon-v despite Their Normal Maturation in Lymphoid Organs during CD137 Monoclonal Antibody Therapy", Cancer Research, vol. 62, pp. 4413-4418 (2002).

Wilcox, R. et al., "Cutting Edge: Expression of Functional CD137 Receptor by Dendritic Cells", Journal of Immunology, vol. 168, pp. 4262-4267 (2002).

Wilcox, R.A., et al., "Signaling Through NK Cell-Associated CD137 Promotes Both Helper Function for $CD8^+$ Cytolytic T Cells and Responsiveness to IL-2 But Not Cytolytic Activity[1]", The Journal of Immunology, vol. 169, pp. 4230-4236 (2002).

Wolchok, J.D., et al., "DNA Vaccines: An Active Immunization Strategy for Prostate Cancer", Seminars in Oncology, vol. 30, No. 5, pp. 659-666 (2003).

Zhang, H., et al., "Tumor Expression of 4-1BB Ligand Sustains Tumor Lytic T Cells", Cancer Biology & Therapy, vol. 2, No. 5, pp. 579-586 (2003).

Zhang, L., et al., "Intratumoral T Cells, Recurrence, and Survival in Epithelial Ovarian Cancer", The New England Journal of Medicine, vol. 348, pp. 203-213 (2003).

Zhou, Z. et al., "Characterization of human homologus of 4-1BB and its ligand", Immunology Letters, vol. 45, pp. 67-73 (1995).

Blazer et al., J. Immunol., vol. 157, pp. 3250-3259 (1996).

Boon et al., Annu. Rev. Immunol., vol. 24, pp. 175-208 (2006).

Kim et al., Immunology, vol. 107, pp. 472-479 (2002).

Lee et al., Advances in Experimental Medicine and Biology, vol. 647, pp. 120-129 (2009).

Lee et al., Cancer J. Immunol., vol. 163, pp. 6292-6300 (1999).

Loo, D.T. et al., "Analysis of 4-1BBL and Laminin Binding to Murine 4-1BB, a Member of the Tumor Necrosis Factor Receptor, Superfamily, and Comparison with Human 4-1BB", The J. of Biological Chemistry, vol. 272(10), pp. 6448-6456 (1997).

Nielsen et al., Cancer Chemother. Pharmacol., vol. 46 (Suppl): pp. S62-S66.

Palma et al., Int. J. Cancer, vol. 108, pp. 390-398 (2004).

Phase II, $2^{nd}$ Line Melanoma—RAND Monotherapy—ClincalTrials.gov, 2011, 4 pages.

Ye Znengmao et al., "Gene Therapy for Cancer Using Single-Chain Fv Fragments Specific for 4-1BB", Nature Medicine, vol. 8(4), pp. 343-348 (2002).

\* cited by examiner

```
  1  CGATGTACGG GCCAGATATA CGCGTTGACA TTGATTATTG ACTAGTTATT
     GCTACATGCC CGGTCTATAT GCGCAACTGT AACTAATAAC TGATCAATAA
 51  AATAGTAATC AATTACGGGG TCATTAGTTC ATAGCCCATA TATGGAGTTC
     TTATCATTAG TTAATGCCCC AGTAATCAAG TATCGGGTAT ATACCTCAAG
101  CGCGTTACAT AACTTACGGT AAATGGCCCG CCTGGCTGAC CGCCCAACGA
     GCGCAATGTA TTGAATGCCA TTTACCGGGC GGACCGACTG GCGGGTTGCT
151  CCCCCGCCCA TTGACGTCAA TAATGACGTA TGTTCCCATA GTAACGCCAA
     GGGGGCGGGT AACTGCAGTT ATTACTGCAT ACAAGGGTAT CATTGCGGTT
201  TAGGGACTTT CCATTGACGT CAATGGGTGG ACTATTTACG GTAAACTGCC
     ATCCCTGAAA GGTAACTGCA GTTACCCACC TGATAAATGC CATTTGACGG
251  CACTTGGCAG TACATCAAGT GTATCATATG CCAAGTACGC CCCCTATTGA
     GTGAACCGTC ATGTAGTTCA CATAGTATAC GGTTCATGCG GGGGATAACT
301  CGTCAATGAC GGTAAATGGC CCGCCTGGCA TTATGCCCAG TACATGACCT
     GCAGTTACTG CCATTTACCG GGCGGACCGT AATACGGGTC ATGTACTGGA
351  TATGGGACTT TCCTACTTGG CAGTACATCT ACGTATTAGT CATCGCTATT
     ATACCCTGAA AGGATGAACC GTCATGTAGA TGCATAATCA GTAGCGATAA
401  ACCATGGTGA TGCGGTTTTG GCAGTACATC AATGGGCGTG GATAGCGGTT
     TGGTACCACT ACGCCAAAAC CGTCATGTAG TTACCCGCAC CTATCGCCAA
451  TGACTCACGG GGATTTCCAA GTCTCCACCC CATTGACGTC AATGGGAGTT
     ACTGAGTGCC CCTAAAGGTT CAGAGGTGGG GTAACTGCAG TTACCCTCAA
501  TGTTTTGGCA CCAAAATCAA CGGGACTTTC CAAAATGTCG TAACAACTCC
     ACAAAACCGT GGTTTTAGTT GCCCTGAAAG GTTTTACAGC ATTGTTGAGG
551  GCCCCATTGA CGCAAATGGG CGGTAGGCGT GTACGGTGGG AGGTCTATAT
     CGGGGTAACT GCGTTTACCC GCCATCCGCA CATGCCACCC TCCAGATATA
601  AAGCAGAGCT CTCTGGCTAA CTAGAGAACC CACTGCTTAC TGGCTTATCG
     TTCGTCTCGA GAGACCGATT GATCTCTTGG GTGACGAATG ACCGAATAGC
                                                        ~~~~~
                                                        M  K  ·
651  AAATTAATAC GACTCACTAT AGGGAGACCC AAGCTTGGTA CCGCCATGAA
     TTTAATTATG CTGAGTGATA TCCCTCTGGG TTCGAACCAT GGCGGTACTT
                  natural Ig leader peptide
     ~~~~~~~~~~~~~~~~~~~~~~~~~~~~~~~~~~~~~~~~~~~~~~~~~~~~~
     ·  H  L  W     F  F  L  L     L  V  A  A  P  R     W  V  L  S  ·
701  ACACCTGTGG TTCTTCCTCC TCCTGGTGGC AGCTCCAGA TGGGTCCTGT
     TGTGGACACC AAGAAGGAGG AGGACCACCG TCGAGGGTCT ACCCAGGACA
     natural Ig leader sequence
     ~~
            20H4-9 HC variable region
     ~~~~~~~~~~~~~~~~~~~~~~~~~~~~~~~~~~~~~~~~~~~~~~~~~~~~~
     ·  Q  V  Q     L  Q  Q     W  G  A  G     L  L  K     P  S  E
751  CCCAGGTGCA ACTACAGCAG TGGGGCGCAG GACTGTTGAA GCCTTCGGAG
     GGGTCCACGT TGATGTCGTC ACCCCGCGTC CTGACAACTT CGGAAGCCTC
                                                          CDR 1
                                                          ~~~~~~~
            20H4-9 HC variable region
     ~~~~~~~~~~~~~~~~~~~~~~~~~~~~~~~~~~~~~~~~~~~~~~~~~~~~~
       T  L  S  L     T  C  A     V  Y  G     G  S  F  S     G  Y  Y  ·
801  ACCCTGTCCC TCACCTGCGC TGTCTATGGT GGGTCCTTCA GTGGTTACTA
     TGGGACAGGG AGTGGACGCG ACAGATACCA CCCAGGAAGT CACCAATGAT
        CDR 1                                            CDR 2
     ~~~~~~~                                              ~
            20H4-9 HC variable region
     ~~~~~~~~~~~~~~~~~~~~~~~~~~~~~~~~~~~~~~~~~~~~~~~~~~~~~
      · W  S  W     I  R  Q  S     P  E  K     G  L  E     W  I  G  E  ·
851  CTGGAGCTGG ATACGCCAGT CCCCAGAGAA GGGGCTGGAG TGGATTGGGG
     GACCTCGACC TATGCGGTCA GGGGTCTCTT CCCCGACCTC ACCTAACCCC
```

FIG. 3A

```
                              CDR 2
              ~~~~~~~~~~~~~~~~~~~~~~~~~~~~~~~~~~~~~~~~~~~~~~~~~~~~~~
                       20H4-9 HC variable region
              ~~~~~~~~~~~~~~~~~~~~~~~~~~~~~~~~~~~~~~~~~~~~~~~~~~~~~~~~
              ·  I    N   H    G   G    Y    V   T    Y   N    P    S    L    E    S   R
       901    AAATCAATCA TGGTGGATAC GTCACCTACA ATCCGTCCCT CGAGAGTCGA
              TTTAGTTAGT ACCACCTATG CAGTGGATGT TAGGCAGGGA GCTCTCAGCT
                       20H4-9 HC variable region
              ~~~~~~~~~~~~~~~~~~~~~~~~~~~~~~~~~~~~~~~~~~~~~~~~~~~~~~~~
                V    T    I    S    V    D   T    S    K   N    Q    F    S    L    K    L    S   ·
       951    GTCACCATAT CAGTAGACAC GTCCAAGAAC CAGTTCTCCC TGAAGCTGAG
              CAGTGGTATA GTCATCTGTG CAGGTTCTTG GTCAAGAGGG ACTTCGACTC
                                                                         CDR 3
                                                                         ~~~~~~~
                       20H4-9 HC variable region
              ~~~~~~~~~~~~~~~~~~~~~~~~~~~~~~~~~~~~~~~~~~~~~~~~~~~~~~~~
              ·  S    V   T    A    A    D    T    A    V    Y    Y   C    A    R    D    Y   G    ·
      1001    CTCTGTGACC GCCGCGGACA CGGCTGTATA TTACTGTGCG AGGGACTATG
              GAGACACTGG CGGCGCCTGT GCCGACATAT AATGACACGC TCCCTGATAC
                            CDR 3
              ~~~~~~~~~~~~~~~~~~~~~~~~~~~~~~~~~~~~~
                       20H4-9 HC variable region
              ~~~~~~~~~~~~~~~~~~~~~~~~~~~~~~~~~~~~~~~~~~~~~~~~~~~~~~~~
              ·  P    G    N    Y    D   W    Y    F    D    L   W    G    R    G    T   L
      1051    GTCCGGGGAA TTATGACTGG TACTTCGATC TCTGGGGCCG TGGCACCCTG
              CAGGCCCCTT AATACTGACC ATGAAGCTAG AGACCCCGGC ACCGTGGGAC
                                                                              IgG4 CH1 domain
                                                                         ~~~~~~~~~~~~~~~~~~~~~~~~~~~~~
              20H4-9 HC variable region
              ~~~~~~~~~~~~~~~~~~~~~
                 V    T    V    S    S    A   S    T    K    G    P    S    V    F    P    L    A   ·
      1101    GTCACTGTCT CCTCAGCTAG CACCAAGGGC CCATCCGTCT TCCCCCTGGC
              CAGTGACAGA GGAGTCGATC GTGGTTCCCG GGTAGGCAGA AGGGGGACCG
                              IgG4 CH1 domain
              ~~~~~~~~~~~~~~~~~~~~~~~~~~~~~~~~~~~~~~~~~~~~~~~~~~~~~~~~
              ·  P   C    S    R    S    T   S    E    S    T    A    A    L   G    C    L    V   ·
      1151    GCCCTGCTCC AGGAGCACCT CCGAGAGCAC AGCCGCCCTG GGCTGCCTGG
              CGGGACGAGG TCCTCGTGGA GGCTCTCGTG TCGGCGGGAC CCGACGGACC
                              IgG4 CH1 domain
              ~~~~~~~~~~~~~~~~~~~~~~~~~~~~~~~~~~~~~~~~~~~~~~~~~~~~~~~~
              ·  K   D    Y    F    P    E    P    V   T    V    S   W    N    S    G    A
      1201    TCAAGGACTA CTTCCCCGAA CCGGTGACGG TGTCGTGGAA CTCAGGCGCC
              AGTTCCTGAT GAAGGGGCTT GGCCACTGCC ACAGCACCTT GAGTCCGCGG
                              IgG4 CH1 domain
              ~~~~~~~~~~~~~~~~~~~~~~~~~~~~~~~~~~~~~~~~~~~~~~~~~~~~~~~~
                 L   T    S    G   V    H    T    F    P    A    V    L    Q    S    S    G    L   ·
      1251    CTGACCAGCG GCGTGCACAC CTTCCCGGCT GTCCTACAGT CCTCAGGACT
              GACTGGTCGC CGCACGTGTG GAAGGGCCGA CAGGATGTCA GGAGTCCTGA
                              IgG4 CH1 domain
              ~~~~~~~~~~~~~~~~~~~~~~~~~~~~~~~~~~~~~~~~~~~~~~~~~~~~~~~~
              ·  Y    S   L    S    S    V   V    T    V    P    S    S    S    L    G    T    K   ·
      1301    CTACTCCCTC AGCAGCGTGG TGACCGTGCC CTCCAGCAGC TTGGGCACGA
              GATGAGGGAG TCGTCGCACC ACTGGCACGG GAGGTCGTCG AACCCGTGCT
```

FIG. 3B

```
                              IgG4 CH1 domain
       ~~~~~~~~~~~~~~~~~~~~~~~~~~~~~~~~~~~~~~~~~~~~~~~~~~~~~~~~~
         · T   Y   T    C   N   V    D   H   K    P   S   N    T   K   V   D ·
 1351    AGACCTACAC CTGCAACGTA GATCACAAGC CCAGCAACAC CAAGGTGGAC
         TCTGGATGTG GACGTTGCAT CTAGTGTTCG GGTCGTTGTG GTTCCACCTG
                              IgG4 hinge region
                      ~~~~~~~~~~~~~~~~~~~~~~~~~~~~~~~~~~~~~~~~~~
IgG4 CH1 domain
~~~~~~~~~          ~~~~~
           K   R   V   E    S   K   Y    G   P   P    C   P   P    C   P   A   P ·
 1401      AAGAGAGTTG AGTCCAAATA TGGTCCACCT TGCCCACCTT GCCCAGCACC
           TTCTCTCAAC TCAGGTTTAT ACCAGGTGGA ACGGGTGGAA CGGGTCGTGG
                              IgG4 CH2 domain
            ~~~~~~~~~~~~~~~~~~~~~~~~~~~~~~~~~~~~~~~~~~~~~~~~~~~~
         · E   F   L    G   G   P    S   V   F    L   F   P    P   K   P   K   D ·
 1451    TGAGTTCCTG GGGGGACCAT CAGTCTTCCT GTTCCCCCCA AAACCCAAGG
         ACTCAAGGAC CCCCCTGGTA GTCAGAAGGA CAAGGGGGGT TTTGGGTTCC
                              IgG4 CH2 domain
         ~~~~~~~~~~~~~~~~~~~~~~~~~~~~~~~~~~~~~~~~~~~~~~~~~~~~~~~
         · T   L   M    I   S   R    T   P   E   V    T   C   V    V   V   D
 1501    ACACTCTCAT GATCTCCCGG ACCCCTGAGG TCACGTGCGT GGTGGTGGAC
         TGTGAGAGTA CTAGAGGGCC TGGGGACTCC AGTGCACGCA CCACCACCTG
                              IgG4 CH2 domain
         ~~~~~~~~~~~~~~~~~~~~~~~~~~~~~~~~~~~~~~~~~~~~~~~~~~~~~~~
           V   S   Q   E    D   P   E    V   Q   F    N   W   Y   V    D   G   V ·
 1551      GTGAGCCAGG AAGACCCCGA GGTCCAGTTC AACTGGTACG TGGATGGCGT
           CACTCGGTCC TTCTGGGGCT CCAGGTCAAG TTGACCATGC ACCTACCGCA
                              IgG4 CH2 domain
          ~~~~~~~~~~~~~~~~~~~~~~~~~~~~~~~~~~~~~~~~~~~~~~~~~~~~~~
         · E   V   H    N   A   K   T    K   P   R    E   E   Q    F   N   S   T ·
 1601    GGAGGTGCAT AATGCCAAGA CAAAGCCGCG GGAGGAGCAG TTCAACAGCA
         CCTCCACGTA TTACGGTTCT GTTTCGGCGC CCTCCTCGTC AAGTTGTCGT
                              IgG4 CH2 domain
          ~~~~~~~~~~~~~~~~~~~~~~~~~~~~~~~~~~~~~~~~~~~~~~~~~~~~~~
         · Y   R   V    V   S   V    L   T   V   L    H   Q   D    W   L   N
 1651    CGTACCGTGT GGTCAGCGTC CTCACCGTCC TGCACCAGGA CTGGCTGAAC
         GCATGGCACA CCAGTCGCAG GAGTGGCAGG ACGTGGTCCT GACCGACTTG
                              IgG4 CH2 domain
          ~~~~~~~~~~~~~~~~~~~~~~~~~~~~~~~~~~~~~~~~~~~~~~~~~~~~~~
           G   K   E   Y    K   C   K    V   S   N    K   G   L    P   S   S   I ·
 1701      GGCAAGGAGT ACAAGTGCAA GGTCTCCAAC AAAGGCCTCC CGTCCTCCAT
           CCGTTCCTCA TGTTCACGTT CCAGAGGTTG TTTCCGGAGG GCAGGAGGTA
                                         IgG4 CH3 domain
                                  ~~~~~~~~~~~~~~~~~~~~~~~~~~~~
IgG4 CH2 domain
~~~~~~~~~~~~~~~~~~~~~~~~~~~~
         · E   K   T    I   S   K   A    K   G   Q    P   R   E    P   Q   V   Y ·
 1751    CGAGAAAACC ATCTCCAAAG CCAAAGGGCA GCCCCGAGAG CCACAGGTGT
         GCTCTTTTGG TAGAGGTTTC GGTTTCCCGT CGGGGCTCTC GGTGTCCACA
                              IgG4 CH3 domain
           ~~~~~~~~~~~~~~~~~~~~~~~~~~~~~~~~~~~~~~~~~~~~~~~~~~~~
         · T   L   P    P   S   Q    E   E   M   T    K   N   Q    V   S   L
 1801    ACACCCTGCC CCCATCCCAG GAGGAGATGA CCAAGAACCA GGTCAGCCTG
         TGTGGGACGG GGGTAGGGTC CTCCTCTACT GGTTCTTGGT CCAGTCGGAC
```

FIG. 3C

```
                        IgG4 CH3 domain
       ~~~~~~~~~~~~~~~~~~~~~~~~~~~~~~~~~~~~~~~~~~~~~~~~~~~~~
         T   C   L   V   K   G   F   Y   P   S   D   I   A   V   E   W   E ·
1851   ACCTGCCTGG TCAAAGGCTT CTACCCCAGC GACATCGCCG TGGAGTGGGA
       TGGACGGACC AGTTTCCGAA GATGGGGTCG CTGTAGCGGC ACCTCACCCT
                        IgG4 CH3 domain
       ~~~~~~~~~~~~~~~~~~~~~~~~~~~~~~~~~~~~~~~~~~~~~~~~~~~~~
       · S   N   G   Q   P   E   N   N   Y   K   T   T   P   P   V   L   D ·
1901   GAGCAATGGG CAGCCGGAGA ACAACTACAA GACCACGCCT CCCGTGCTGG
       CTCGTTACCC GTCGGCCTCT TGTTGATGTT CTGGTGCGGA GGGCACGACC
                        IgG4 CH3 domain
       ~~~~~~~~~~~~~~~~~~~~~~~~~~~~~~~~~~~~~~~~~~~~~~~~~~~~~
       ·  S   D   G   S   F   F   L   Y   S   R   L   T   V   D   K   S
1951   ACTCCGACGG CTCCTTCTTC CTCTACAGCA GGCTAACCGT GGACAAGAGC
       TGAGGCTGCC GAGGAAGAAG GAGATGTCGT CCGATTGGCA CCTGTTCTCG
                        IgG4 CH3 domain
       ~~~~~~~~~~~~~~~~~~~~~~~~~~~~~~~~~~~~~~~~~~~~~~~~~~~~~
         R   W   Q   E   G   N   V   F   S   C   S   V   M   H   E   A   L ·
2001   AGGTGGCAGG AGGGGAATGT CTTCTCATGC TCCGTGATGC ATGAGGCTCT
       TCCACCGTCC TCCCCTTACA GAAGAGTACG AGGCACTACG TACTCCGAGA
                        IgG4 CH3 domain
       ~~~~~~~~~~~~~~~~~~~~~~~~~~~~~~~~~~~~~~~~~~~~~~~~~~~~~
       · H   N   H   Y   T   Q   K   S   L   S   L   S   L   G   K
2051   GCACAACCAC TACACACAGA AGAGCCTCTC CCTGTCTCTG GGTAAATGAT
       CGTGTTGGTG ATGTGTGTCT TCTCGGAGAG GGACAGAGAC CCATTTACTA
2101   CTAGAGGGCC CTATTCTATA GTGTCACCTA AATGCTAGAG CTCGCTGATC
       GATCTCCCGG GATAAGATAT CACAGTGGAT TTACGATCTC GAGCGACTAG
2151   AGCCTCGACT GTGCCTTCTA GTTGCCAGCC ATCTGTTGTT TGCCCCTCCC
       TCGGAGCTGA CACGGAAGAT CAACGGTCGG TAGACAACAA ACGGGGAGGG
2201   CCGTGCCTTC CTTGACCCTG GAAGGTGCCA CTCCCACTGT CCTTTCCTAA
       GGCACGGAAG GAACTGGGAC CTTCCACGGT GAGGGTGACA GGAAAGGATT
2251   TAAAATGAGG AAATTGCATC GCATTGTCTG AGTAGGTGTC ATTCTATTCT
       ATTTTACTCC TTTAACGTAG CGTAACAGAC TCATCCACAG TAAGATAAGA
2301   GGGGGGGTGGG GTGGGGCAGG ACAGCAAGGG GGAGGATTGG GAAGACAATA
       CCCCCCACCC CACCCCGTCC TGTCGTTCCC CCTCCTAACC CTTCTGTTAT
2351   GCAGGCATGC TGGGGATGCG GTGGGCTCTA TGGCTTCTGA GGCGGAAAGA
       CGTCCGTACG ACCCCTACGC CACCCGAGAT ACCGAAGACT CCGCCTTTCT
2401   ACCAGCTGGG GCTCTAGGGG GTATCCCCAC GCGCCCTGTA GCGGCGCATT
       TGGTCGACCC CGAGATCCCC CATAGGGGTG CGCGGGACAT CGCCGCGTAA
2451   AAGCGCGGCG GGTGTGGTGG TTACGCGCAG CGTGACCGCT ACACTTGCCA
       TTCGCGCCGC CCACACCACC AATGCGCGTC GCACTGGCGA TGTGAACGGT
2501   GCGCCCTAGC GCCCGCTCCT TTCGCTTTCT TCCCTTCCTT TCTCGCCACG
       CGCGGGATCG CGGGCGAGGA AAGCGAAAGA AGGGAAGGAA AGAGCGGTGC
2551   TTCGCCGGGC CTCTCAAAAA AGGGAAAAAA AGCATGCATC TCAATTAGTC
       AAGCGGCCCG GAGAGTTTTT TCCCTTTTTT TCGTACGTAG AGTTAATCAG
2601   AGCAACCATA GTCCCGCCCC TAACTCCGCC CATCCCGCCC CTAACTCCGC
       TCGTTGGTAT CAGGGCGGGG ATTGAGGCGG GTAGGGCGGG GATTGAGGCG
2651   CCAGTTCCGC CCATTCTCCG CCCCATGGCT GACTAATTTT TTTTATTTAT
       GGTCAAGGCG GGTAAGAGGC GGGGTACCGA CTGATTAAAA AAAATAAATA
2701   GCAGAGGCCG AGGCCGCCTC GGCCTCTGAG CTATTCCAGA AGTAGTGAGG
       CGTCTCCGGC TCCGGCGGAG CCGGAGACTC GATAAGGTCT TCATCACTCC
2751   AGGCTTTTTT GGAGGCCTAG GCTTTTGCAA AAAGCTTGGA CAGCTCAGGG
       TCCGAAAAAA CCTCCGGATC CGAAAACGTT TTTCGAACCT GTCGAGTCCC
2801   CTGCGATTTC GCGCCAAACT TGACGGCAAT CCTAGCGTGA AGGCTGGTAG
       GACGCTAAAG CGCGGTTTGA ACTGCCGTTA GGATCGCACT TCCGACCATC
```

FIG. 3D

```
2851  GATTTTATCC CCGCTGCCAT CATGGTTCGA CCATTGAACT GCATCGTCGC
      CTAAAATAGG GGCGACGGTA GTACCAAGCT GGTAACTTGA CGTAGCAGCG
2901  CGTGTCCCAA AATATGGGGA TTGGCAAGAA CGGAGACCTA CCCTGGCCTC
      GCACAGGGTT TTATACCCCT AACCGTTCTT GCCTCTGGAT GGGACCGGAG
2951  CGCTCAGGAA CGAGTTCAAG TACTTCCAAA GAATGACCAC AACCTCTTCA
      GCGAGTCCTT GCTCAAGTTC ATGAAGGTTT CTTACTGGTG TTGGAGAAGT
3001  GTGGAAGGTA AACAGAATCT GGTGATTATG GGTAGGAAAA CCTGGTTCTC
      CACCTTCCAT TTGTCTTAGA CCACTAATAC CCATCCTTTT GGACCAAGAG
3051  CATTCCTGAG AAGAATCGAC CTTTAAAGGA CAGAATTAAT ATAGTTCTCA
      GTAAGGACTC TTCTTAGCTG GAAATTTCCT GTCTTAATTA TATCAAGAGT
3101  GTAGAGAACT CAAAGAACCA CCACGAGGAG CTCATTTTCT TGCCAAAAGT
      CATCTCTTGA GTTTCTTGGT GGTGCTCCTC GAGTAAAAGA ACGGTTTTCA
3151  TTGGATGATG CCTTAAGACT TATTGAACAA CCGGAATTGG CAAGTAAAGT
      AACCTACTAC GGAATTCTGA ATAACTTGTT GGCCTTAACC GTTCATTTCA
3201  AGACATGGTT TGGATAGTCG GAGGCAGTTC TGTTTACCAG GAAGCCATGA
      TCTGTACCAA ACCTATCAGC CTCCGTCAAG ACAAATGGTC CTTCGGTACT
3251  ATCAACCAGG CCACCTTAGA CTCTTTGTGA CAAGGATCAT GCAGGAATTT
      TAGTTGGTCC GGTGGAATCT GAGAAACACT GTTCCTAGTA CGTCCTTAAA
3301  GAAAGTGACA CGTTTTTCCC AGAAATTGAT TTGGGGAAAT ATAAACTTCT
      CTTTCACTGT GCAAAAGGG TCTTTAACTA AACCCCTTTA TATTTGAAGA
3351  CCCAGAATAC CCAGGCGTCC TCTCTGAGGT CCAGGAGGAA AAAGGCATCA
      GGGTCTTATG GGTCCGCAGG AGAGACTCCA GGTCCTCCTT TTTCCGTAGT
3401  AGTATAAGTT TGAAGTCTAC GAGAAGAAAG ACTAACAGGA AGATGCTTTC
      TCATATTCAA ACTTCAGATG CTCTTCTTTC TGATTGTCCT TCTACGAAAG
3451  AAGTTCTCTG CTCCCCTCCT AAAGCTATGC ATTTTTATAA GACCATGGGA
      TTCAAGAGAC GAGGGGAGGA TTTCGATACG TAAAAATATT CTGGTACCCT
3501  CTTTTGCTGG CTTTAGATCT CTTTGTGAAG GAACCTTACT TCTGTGGTGT
      GAAAACGACC GAAATCTAGA GAAACACTTC CTTGGAATGA AGACACCACA
3551  GACATAATTG GACAAACTAC CTACAGAGAT TTAAAGCTCT AAGGTAAATA
      CTGTATTAAC CTGTTTGATG GATGTCTCTA AATTTCGAGA TTCCATTTAT
3601  TAAAATTTTT AAGTGTATAA TGTGTTAAAC TACTGATTCT AATTGTTTGT
      ATTTTAAAAA TTCACATATT ACACAATTTG ATGACTAAGA TTAACAAACA
3651  GTATTTTAGA TTCCAACCTA TGGAACTGAT GAATGGGAGC AGTGGTGGAA
      CATAAAATCT AAGGTTGGAT ACCTTGACTA CTTACCCTCG TCACCACCTT
3701  TGCCTTTAAT GAGGAAAACC TGTTTGCTC AGAAGAAATG CCATCTAGTG
      ACGGAAATTA CTCCTTTTGG ACAAACGAG TCTTCTTTAC GGTAGATCAC
3751  ATGATGAGGC TACTGCTGAC TCTCAACATT CTACTCCTCC AAAAAAGAAG
      TACTACTCCG ATGACGACTG AGAGTTGTAA GATGAGGAGG TTTTTCTTC
3801  AGAAAGGTAG AAGACCCCAA GGACTTTCCT TCAGAATTGC TAAGTTTTTT
      TCTTTCCATC TTCTGGGGTT CCTGAAAGGA AGTCTTAACG ATTCAAAAAA
3851  GAGTCATGCT GTGTTTAGTA ATAGAACTCT TGCTTGCTTT GCTATTTACA
      CTCAGTACGA CACAAATCAT TATCTTGAGA ACGAACGAAA CGATAAATGT
3901  CCACAAAGGA AAAAGCTGCA CTGCTATACA AGAAAATTAT GGAAAAATAT
      GGTGTTTCCT TTTTCGACGT GACGATATGT TCTTTTAATA CCTTTTTATA
3951  TCTGTAACCT TTATAAGTAG GCATAACAGT TATAATCATA ACATACTGTT
      AGACATTGGA AATATTCATC CGTATTGTCA ATATTAGTAT TGTATGACAA
4001  TTTTCTTACT CCACACAGGC ATAGAGTGTC TGCTATTAAT AACTATGCTC
      AAAAGAATGA GGTGTGTCCG TATCTCACAG ACGATAATTA TTGATACGAG
4051  AAAAATTGTG TACCTTTAGC TTTTTAATTT GTAAAGGGGT TAATAAGGAA
      TTTTTAACAC ATGGAAATCG AAAAATTAAA CATTTCCCCA ATTATTCCTT
4101  TATTTGATGT ATAGTGCCTT GACTAGAGAT CATAATCAGC CATACCACAT
      ATAAACTACA TATCACGGAA CTGATCTCTA GTATTAGTCG GTATGGTGTA
4151  TTGTAGAGGT TTTACTTGCT TTAAAAAACC TCCCACACCT CCCCCTGAAC
      AACATCTCCA AAATGAACGA AATTTTTGG AGGGTGTGGA GGGGGACTTG
4201  CTGAAACATA AAATGAATGC AATTGTTGTT GTTAACTTGT TTATTGCAGC
```

FIG. 3E

```
       GACTTTGTAT TTTACTTACG TTAACAACAA CAATTGAACA AATAACGTCG
 4251  TTATAATGGT TACAAATAAA GCAATAGCAT CACAAATTTC ACAAATAAAG
       AATATTACCA ATGTTTATTT CGTTATCGTA GTGTTTAAAG TGTTTATTTC
 4301  CATTTTTTTC ACTGCATTCT AGTTGTGGTT TGTCCAAACT CATCAATGTA
       GTAAAAAAAG TGACGTAAGA TCAACACCAA ACAGGTTTGA GTAGTTACAT
 4351  TCTTATCATG TCTGGATCGG CTGGATGATC CTCCAGCGCG GGGATCTCAT
       AGAATAGTAC AGACCTAGCC GACCTACTAG GAGGTCGCGC CCCTAGAGTA
 4401  GCTGGAGTTC TTCGCCCACC CCAACTTGTT TATTGCAGCT TATAATGGTT
       CGACCTCAAG AAGCGGGTGG GGTTGAACAA ATAACGTCGA ATATTACCAA
 4451  ACAAATAAAG CAATAGCATC ACAAATTTCA CAAATAAAGC ATTTTTTTCA
       TGTTTATTTC GTTATCGTAG TGTTTAAAGT GTTTATTTCG TAAAAAAAGT
 4501  CTGCATTCTA GTTGTGGTTT GTCCAAACTC ATCAATGTAT CTTATCATGT
       GACGTAAGAT CAACACCAAA CAGGTTTGAG TAGTTACATA GAATAGTACA
 4551  CTGTATACCG TCGACCTCTA GCTAGAGCTT GGCGTAATCA TGGTCATAGC
       GACATATGGC AGCTGGAGAT CGATCTCGAA CCGCATTAGT ACCAGTATCG
 4601  TGTTTCCTGT GTGAAATTGT TATCCGCTCA CAATTCCACA ACATACGA
       ACAAAGGACA CACTTTAACA ATAGGCGAGT GTTAAGGTGT GTTGTATGCT
 4651  GCCGGAAGCA TAAAGTGTAA AGCCTGGGGT GCCTAATGAG TGAGCTAACT
       CGGCCTTCGT ATTTCACATT TCGGACCCCA CGGATTACTC ACTCGATTGA
 4701  CACATTAATT GCGTTGCGCT CACTGCCCGC TTTCCAGTCG GGAAACCTGT
       GTGTAATTAA CGCAACGCGA GTGACGGGCG AAAGGTCAGC CCTTTGGACA
 4751  CGTGCCAGCT GCATTAATGA ATCGGCCAAC GCGCGGGGAG AGGCGGTTTG
       GCACGGTCGA CGTAATTACT TAGCCGGTTG CGCGCCCCTC TCCGCCAAAC
 4801  CGTATTGGGC GCTCTTCCGC TTCCTCGCTC ACTGACTCGC TGCGCTCGGT
       GCATAACCCG CGAGAAGGCG AAGGAGCGAG TGACTGAGCG ACGCGAGCCA
 4851  CGTTCGGCTG CGGCGAGCGG TATCAGCTCA CTCAAAGGCG GTAATACGGT
       GCAAGCCGAC GCCGCTCGCC ATAGTCGAGT GAGTTTCCGC CATTATGCCA
 4901  TATCCACAGA ATCAGGGGAT AACGCAGGAA AGAACATGTG AGCAAAAGGC
       ATAGGTGTCT TAGTCCCCTA TTGCGTCCTT TCTTGTACAC TCGTTTTCCG
 4951  CAGCAAAAGG CCAGGAACCG TAAAAAGGCC GCGTTGCTGG CGTTTTTCCA
       GTCGTTTTCC GGTCCTTGGC ATTTTTCCGG CGCAACGACC GCAAAAAGGT
 5001  TAGGCTCCGC CCCCCTGACG AGCATCACAA AAATCGACGC TCAAGTCAGA
       ATCCGAGGCG GGGGGACTGC TCGTAGTGTT TTTAGCTGCG AGTTCAGTCT
 5051  GGTGGCGAAA CCCGACAGGA CTATAAAGAT ACCAGGCGTT TCCCCCTGGA
       CCACCGCTTT GGGCTGTCCT GATATTTCTA TGGTCCGCAA AGGGGGACCT
 5101  AGCTCCCTCG TGCGCTCTCC TGTTCCGACC CTGCCGCTTA CCGGATACCT
       TCGAGGGAGC ACGCGAGAGG ACAAGGCTGG GACGGCGAAT GGCCTATGGA
 5151  GTCCGCCTTT CTCCCTTCGG GAAGCGTGGC GCTTTCTCAA TGCTCACGCT
       CAGGCGGAAA GAGGGAAGCC CTTCGCACCG CGAAAGAGTT ACGAGTGCGA
 5201  GTAGGTATCT CAGTTCGGTG TAGGTCGTTC GCTCCAAGCT GGGCTGTGTG
       CATCCATAGA GTCAAGCCAC ATCCAGCAAG CGAGGTTCGA CCCGACACAC
 5251  CACGAACCCC CCGTTCAGCC CGACCGCTGC GCCTTATCCG GTAACTATCG
       GTGCTTGGGG GGCAAGTCGG GCTGGCGACG CGGAATAGGC CATTGATAGC
 5301  TCTTGAGTCC AACCCGGTAA GACACGACTT ATCGCCACTG GCAGCAGCCA
       AGAACTCAGG TTGGGCCATT CTGTGCTGAA TAGCGGTGAC CGTCGTCGGT
 5351  CTGGTAACAG GATTAGCAGA GCGAGGTATG TAGGCGGTGC TACAGAGTTC
       GACCATTGTC CTAATCGTCT CGCTCCATAC ATCCGCCACG ATGTCTCAAG
 5401  TTGAAGTGGT GGCCTAACTA CGGCTACACT AGAAGGACAG TATTTGGTAT
       AACTTCACCA CCGGATTGAT GCCGATGTGA TCTTCCTGTC ATAAACCATA
 5451  CTGCGCTCTG CTGAAGCCAG TTACCTTCGG AAAAAGAGTT GGTAGCTCTT
       GACGCGAGAC GACTTCGGTC AATGGAAGCC TTTTTCTCAA CCATCGAGAA
 5501  GATCCGGCAA ACAAACCACC GCTGGTAGCG GTGGTTTTTT TGTTTGCAAG
       CTAGGCCGTT TGTTTGGTGG CGACCATCGC CACCAAAAAA ACAAACGTTC
 5551  CAGCAGATTA CGCGCAGAAA AAAAGGATCT CAAGAAGATC CTTTGATCTT
       GTCGTCTAAT GCGCGTCTTT TTTTCCTAGA GTTCTTCTAG GAAACTAGAA
```

FIG. 3F

```
5601   TTCTACGGGG TCTGACGCTC AGTGGAACGA AAACTCACGT TAAGGGATTT
       AAGATGCCCC AGACTGCGAG TCACCTTGCT TTTGAGTGCA ATTCCCTAAA
5651   TGGTCATGAG ATTATCAAAA AGGATCTTCA CCTAGATCCT TTTAAATTAA
       ACCAGTACTC TAATAGTTTT TCCTAGAAGT GGATCTAGGA AAATTTAATT
5701   AAATGAAGTT TTAAATCAAT CTAAAGTATA TATGAGTAAA CTTGGTCTGA
       TTTACTTCAA AATTTAGTTA GATTTCATAT ATACTCATTT GAACCAGACT
5751   CAGTTACCAA TGCTTAATCA GTGAGGCACC TATCTCAGCG ATCTGTCTAT
       GTCAATGGTT ACGAATTAGT CACTCCGTGG ATAGAGTCGC TAGACAGATA
5801   TTCGTTCATC CATAGTTGCC TGACTCCCCG TCGTGTAGAT AACTACGATA
       AAGCAAGTAG GTATCAACGG ACTGAGGGGC AGCACATCTA TTGATGCTAT
5851   CGGGAGGGCT TACCATCTGG CCCCAGTGCT GCAATGATAC CGCGAGACCC
       GCCCTCCCGA ATGGTAGACC GGGGTCACGA CGTTACTATG GCGCTCTGGG
5901   ACGCTCACCG GCTCCAGATT TATCAGCAAT AAACCAGCCA GCCGGAAGGG
       TGCGAGTGGC CGAGGTCTAA ATAGTCGTTA TTTGGTCGGT CGGCCTTCCC
5951   CCGAGCGCAG AAGTGGTCCT GCAACTTTAT CCGCCTCCAT CCAGTCTATT
       GGCTCGCGTC TTCACCAGGA CGTTGAAATA GGCGGAGGTA GGTCAGATAA
6001   AATTGTTGCC GGGAAGCTAG AGTAAGTAGT TCGCCAGTTA ATAGTTTGCG
       TTAACAACGG CCCTTCGATC TCATTCATCA AGCGGTCAAT TATCAAACGC
6051   CAACGTTGTT GCCATTGCTA CAGGCATCGT GGTGTCACGC TCGTCGTTTG
       GTTGCAACAA CGGTAACGAT GTCCGTAGCA CCACAGTGCG AGCAGCAAAC
6101   GTATGGCTTC ATTCAGCTCC GGTTCCCAAC GATCAAGGCG AGTTACATGA
       CATACCGAAG TAAGTCGAGG CCAAGGGTTG CTAGTTCCGC TCAATGTACT
6151   TCCCCCATGT TGTGCAAAAA AGCGGTTAGC TCCTTCGGTC CTCCGATCGT
       AGGGGGTACA ACACGTTTTT TCGCCAATCG AGGAAGCCAG GAGGCTAGCA
6201   TGTCAGAAGT AAGTTGGCCG CAGTGTTATC ACTCATGGTT ATGGCAGCAC
       ACAGTCTTCA TTCAACCGGC GTCACAATAG TGAGTACCAA TACCGTCGTG
6251   TGCATAATTC TCTTACTGTC ATGCCATCCG TAAGATGCTT TTCTGTGACT
       ACGTATTAAG AGAATGACAG TACGGTAGGC ATTCTACGAA AAGACACTGA
6301   GGTGAGTACT CAACCAAGTC ATTCTGAGAA TAGTGTATGC GGCGACCGAG
       CCACTCATGA GTTGGTTCAG TAAGACTCTT ATCACATACG CCGCTGGCTC
6351   TTGCTCTTGC CCGGCGTCAA TACGGGATAA TACCGCGCCA CATAGCAGAA
       AACGAGAACG GGCCGCAGTT ATGCCCTATT ATGGCGCGGT GTATCGTCTT
6401   CTTTAAAAGT GCTCATCATT GGAAAACGTT CTTCGGGGCG AAAACTCTCA
       GAAATTTTCA CGAGTAGTAA CCTTTTGCAA GAAGCCCGC TTTTGAGAGT
6451   AGGATCTTAC CGCTGTTGAG ATCCAGTTCG ATGTAACCCA CTCGTGCACC
       TCCTAGAATG GCGACAACTC TAGGTCAAGC TACATTGGGT GAGCACGTGG
6501   CAACTGATCT TCAGCATCTT TTACTTTCAC CAGCGTTTCT GGGTGAGCAA
       GTTGACTAGA AGTCGTAGAA AATGAAAGTG GTCGCAAAGA CCCACTCGTT
6551   AAACAGGAAG GCAAAATGCC GCAAAAAAGG GAATAAGGGC GACACGGAAA
       TTTGTCCTTC CGTTTTACGG CGTTTTTTCC CTTATTCCCG CTGTGCCTTT
6601   TGTTGAATAC TCATACTCTT CCTTTTTCAA TATTATTGAA GCATTATCA
       ACAACTTATG AGTATGAGAA GGAAAAGTT ATAATAACTT CGTAAATAGT
6651   GGGTTATTGT CTCATGAGCG GATACATATT TGAATGTATT TAGAAAAATA
       CCCAATAACA GAGTACTCGC CTATGTATAA ACTTACATAA ATCTTTTTAT
6701   AACAAATAGG GGTTCCGCGC ACATTTCCCC GAAAAGTGCC ACCTGACGTC
       TTGTTTATCC CCAAGGCGCG TGTAAAGGGG CTTTTCACGG TGGACTGCAG
6751   GACGGATCGG GAGATCTGCT AGGTGACCTG AGGCGCGCCG CTTCGAATA
       CTGCCTAGCC CTCTAGACGA TCCACTGGAC TCCGCGCGGC GAAGCTTAT
6801   GCCAGAGTAA CCTTTTTTTT TAATTTTATT TTATTTTATT TTTGAGATGG
       CGGTCTCATT GGAAAAAAAA ATTAAAATAA AATAAAATAA AAACTCTACC
6851   AGTTTGGCGC CGATCTCCCG ATCCCTATG GTCGACTCTC AGTACAATCT
       TCAAACCGCG GCTAGAGGGC TAGGGGATAC CAGCTGAGAG TCATGTTAGA
6901   GCTCTGATGC CGCATAGTTA AGCCAGTATC TGCTCCCTGC TTGTGTGTTG
       CGAGACTACG GCGTATCAAT TCGGTCATAG ACGAGGGACG AACACACAAC
6951   GAGGTCGCTG AGTAGTGCGC GAGCAAAATT TAAGCTACAA CAAGGCAAGG
```

FIG. 3G

```
          CTCCAGCGAC TCATCACGCG CTCGTTTTAA ATTCGATGTT GTTCCGTTCC
    7001  CTTGACCGAC AATTGCATGA AGAATCTGCT TAGGGTTAGG CGTTTTGCGC
          GAACTGGCTG TTAACGTACT TCTTAGACGA ATCCCAATCC GCAAAACGCG
    7051  TGCTTCG
          ACGAAGC
```

FIG. 3H

```
   1 GACGGATCGG GAGATCTGCT AGCCCGGGTG ACCTGAGGCG CGCCGGCTTC
     CTGCCTAGCC CTCTAGACGA TCGGGCCCAC TGGACTCCGC GCGGCCGAAG
  51 GAATAGCCAG AGTAACCTTT TTTTTTAATT TTATTTTATT TTATTTTTGA
     CTTATCGGTC TCATTGGAAA AAAAAATTAA AATAAAATAA AATAAAAACT
 101 GATGGAGTTT GGCGCCGATC TCCCGATCCC CTATGGTCGA CTCTCAGTAC
     CTACCTCAAA CCGCGGCTAG AGGGCTAGGG GATACCAGCT GAGAGTCATG
 151 AATCTGCTCT GATGCCGCAT AGTTAAGCCA GTATCTGCTC CCTGCTTGTG
     TTAGACGAGA CTACGGCGTA TCAATTCGGT CATAGACGAG GGACGAACAC
 201 TGTTGGAGGT CGCTGAGTAG TGCGCGAGCA AAATTTAAGC TACAACAAGG
     ACAACCTCCA GCGACTCATC ACGCGCTCGT TTTAAATTCG ATGTTGTTCC
 251 CAAGGCTTGA CCGACAATTG CATGAAGAAT CTGCTTAGGG TTAGGCGTTT
     GTTCCGAACT GGCTGTTAAC GTACTTCTTA GACGAATCCC AATCCGCAAA
 301 TGCGCTGCTT CGCGATGTAC GGGCCAGATA TACGCGTTGA CATTGATTAT
     ACGCGACGAA GCGCTACATG CCCGGTCTAT ATGCGCAACT GTAACTAATA
 351 TGACTAGTTA TTAATAGTAA TCAATTACGG GGTCATTAGT TCATAGCCCA
     ACTGATCAAT AATTATCATT AGTTAATGCC CCAGTAATCA AGTATCGGGT
 401 TATATGGAGT TCCGCGTTAC ATAACTTACG GTAAATGGCC CGCCTGGCTG
     ATATACCTCA AGGCGCAATG TATTGAATGC CATTTACCGG GCGGACCGAC
 451 ACCGCCCAAC GACCCCCGCC CATTGACGTC AATAATGACG TATGTTCCCA
     TGGCGGGTTG CTGGGGGCGG GTAACTGCAG TTATTACTGC ATACAAGGGT
 501 TAGTAACGCC AATAGGGACT TTCCATTGAC GTCAATGGGT GGAGTATTTA
     ATCATTGCGG TTATCCCTGA AAGGTAACTG CAGTTACCCA CCTCATAAAT
 551 CGGTAAACTG CCCACTTGGC AGTACATCAA GTGTATCATA TGCCAAGTAC
     GCCATTTGAC GGGTGAACCG TCATGTAGTT CACATAGTAT ACGGTTCATG
 601 GCCCCTATT GACGTCAATG ACGGTAAATG GCCCGCCTGG CATTATGCCC
     CGGGGGATAA CTGCAGTTAC TGCCATTTAC CGGGCGGACC GTAATACGGG
 651 AGTACATGAC CTTATGGGAC TTTCCTACTT GGCAGTACAT CTACGTATTA
     TCATGTACTG GAATACCCTG AAAGGATGAA CCGTCATGTA GATGCATAAT
 701 GTCATCGCTA TTACCATGGT GATGCGGTTT TGGCAGTACA TCAATGGGCG
     CAGTAGCGAT AATGGTACCA CTACGCCAAA ACCGTCATGT AGTTACCCGC
 751 TGGATAGCGG TTTGACTCAC GGGGATTTCC AAGTCTCCAC CCCATTGACG
     ACCTATCGCC AAACTGAGTG CCCCTAAAGG TTCAGAGGTG GGGTAACTGC
 801 TCAATGGGAG TTTGTTTTGG CACCAAAATC AACGGGACTT TCCAAAATGT
     AGTTACCCTC AAACAAAACC GTGGTTTTAG TTGCCCTGAA AGGTTTTACA
 851 CGTAACAACT CCGCCCCATT GACGCAAATG GGCGGTAGGC GTGTACGGTG
     GCATTGTTGA GGCGGGGTAA CTGCGTTTAC CCGCCATCCG CACATGCCAC
 901 GGAGGTCTAT ATAAGCAGAG CTCTCTGGCT AACTAGAGAA CCCACTGCTT
     CCTCCAGATA TATTCGTCTC GAGAGACCGA TTGATCTCTT GGGTGACGAA
 951 ACTGGCTTAT CGAAATTAAT ACGACTCACT ATAGGGAGAC CCAAGCTTAT
     TGACCGAATA GCTTTAATTA TGCTGAGTGA TATCCCTCTG GGTTCGAATA
                                                       Natural Ig leader
                                                       ~~~~~~~~~~~~~~~~~
                                                         M   E   A  P   A   Q ·
1001 CAACAAGTTT GTACAAAAAA GCAGGCTGGT ACCATGGAAG CCCCAGCTCA
     GTTGTTCAAA CATGTTTTTT CGTCCGACCA TGGTACCTTC GGGGTCGAGT
                                                           ~~~~~~~
            Natural Ig leader peptide
     ~~~~~~~~~~~~~~~~~~~~~~~~~~~~~~~~~~~~~~~~~~~~~~~~
     · L   L   F   L   L   L   L   W   L   P   D   T   T   G   E   I   V ·
1051 GCTTCTCTTC CTCCTGCTAC TCTGGCTCCC AGATACCACC GGAGAAATTG
     CGAAGAGAAG GAGGACGATG AGACCGAGGG TCTATGGTGG CCTCTTTAAC
```

FIG. 4A

20H4-9 LC variable region

```
           ·  L    T    Q    S    P    A    T    L    S    L    S    P    G    E    R    A
1101       TGTTGACACA GTCTCCAGCC ACCCTGTCTT TGTCTCCAGG GGAAAGAGCC
           ACAACTGTGT CAGAGGTCGG TGGGACAGAA ACAGAGGTCC CCTTTCTCGG
```

20H4-9 LC variable region

CDR 1

```
            T    L    S    C    R    A    S    Q    S    V    S    S    Y    L    A    W    Y ·
1151       ACCCTCTCCT GCAGGGCCAG TCAGAGTGTT AGCAGCTACT TAGCCTGGTA
           TGGGAGAGGA CGTCCCGGTC AGTCTCACAA TCGTCGATGA ATCGGACCAT
```

20H4-9 LC variable region

CDR 2

```
           · Q    Q    K    P    G    Q    A    P    R    L    L    I    Y    D    A    S    N ·
1201       CCAACAGAAA CCTGGCCAGG CTCCCAGGCT CCTCATCTAT GATGCATCCA
           GGTTGTCTTT GGACCGGTCC GAGGGTCCGA GGAGTAGATA CTACGTAGGT
```

20H4-9 LC variable region

CDR 2

```
           ·  R    A    T    G    I    P    A    R    F    S    G    S    G    S    T
1251       ACAGGGCCAC TGGCATCCCA GCCAGGTTCA GTGGCAGTGG GTCTGGGACA
           TGTCCCGGTG ACCGTAGGGT CGGTCCAAGT CACCGTCACC CAGACCCTGT
```

20H4-9 LC variable region

```
            D    F    T    L    T    I    S    S    L    E    P    E    D    F    A    V    Y ·
1301       GACTTCACTC TCACCATCAG CAGCCTAGAG CCTGAAGATT TTGCAGTTTA
           CTGAAGTGAG AGTGGTAGTC GTCGGATCTC GGACTTCTAA AACGTCAAAT
```

CDR 3

20H4-9 LC variable region

```
           · Y    C    Q    Q    R    S    N    W    P    P    A    L    T    F    G    G    G ·
1351       TTACTGTCAG CAGCGTAGCA ACTGGCCTCC GGCGCTCACT TTCGGCGGAG
           AATGACAGTC GTCGCATCGT TGACCGGAGG CCGCGAGTGA AAGCCGCCTC
```

C-kappa

20H4-9 LC variable region

```
           ·  T    K    V    E    I    K    R    T    V    A    A    P    S    V    F    I
1401       GGACCAAGGT GGAGATCAAA CGTACGGTGG CTGCACCATC TGTCTTCATC
           CCTGGTTCCA CCTCTAGTTT GCATGCCACC GACGTGGTAG ACAGAAGTAG
```

C-kappa

```
            F    P    P    S    D    E    Q    L    K    S    G    T    A    S    V    V    C ·
1451       TTCCCGCCAT CTGATGAGCA GTTGAAATCT GGAACTGCCT CTGTTGTGTG
           AAGGGCGGTA GACTACTCGT CAACTTTAGA CCTTGACGGA GACAACACAC
```

C-kappa

```
           · L    L    N    N    F    Y    P    R    E    A    K    V    Q    W    K    V    D ·
1501       CCTGCTGAAT AACTTCTATC CCAGAGAGGC CAAAGTACAG TGGAAGGTGG
           GGACGACTTA TTGAAGATAG GGTCTCTCCG GTTTCATGTC ACCTTCCACC
```

FIG. 4B

```
                   C-kappa
      ~~~~~~~~~~~~~~~~~~~~~~~~~~~~~~~~~~~~~~~~~~~~~~~~~~
      ·  N  A  L     Q  S  G     N  S  Q  E     S  V  T     E  Q  D
1551  ATAACGCCCT CCAATCGGGT AACTCCCAGG AGAGTGTCAC AGAGCAGGAC
      TATTGCGGGA GGTTAGCCCA TTGAGGGTCC TCTCACAGTG TCTCGTCCTG
                   C-kappa
      ~~~~~~~~~~~~~~~~~~~~~~~~~~~~~~~~~~~~~~~~~~~~~~~~~~
         S  K  D  S     T  Y  S     L  S  S     T  L  T     L  S  K  A ·
1601  AGCAAGGACA GCACCTACAG CCTCAGCAGC ACCCTGACGC TGAGCAAAGC
      TCGTTCCTGT CGTGGATGTC GGAGTCGTCG TGGGACTGCG ACTCGTTTCG
                   C-kappa
      ~~~~~~~~~~~~~~~~~~~~~~~~~~~~~~~~~~~~~~~~~~~~~~~~~~
      ·  D  Y  E     K  H  K  V     Y  A  C     E  V  T     H  Q  G  L ·
1651  AGACTACGAG AAACACAAAG TCTACGCCTG CGAAGTCACC CATCAGGGCC
      TCTGATGCTC TTTGTGTTTC AGATGCGGAC GCTTCAGTGG GTAGTCCCGG
                   C-kappa
      ~~~~~~~~~~~~~~~~~~~~~~~~~~~~~~~~~~~~~~~~~~~~~~~~~~
      ·  S  S  P     V  T  K     S  F  N  R     G  E  C
1701  TGAGCTCGCC CGTCACAAAG AGCTTCAACA GGGGAGAGTG TTAGACCCAG
      ACTCGAGCGG GCAGTGTTTC TCGAAGTTGT CCCCTCTCAC AATCTGGGTC
1751  CTTTCTTGTA CAAAGTGGTT GATCTAGAGG GCCCTATTCT ATAGTGTCAC
      GAAAGAACAT GTTTCACCAA CTAGATCTCC CGGGATAAGA TATCACAGTG
1801  CTAAATGCTA GAGCTCGCTG ATCAGCCTCG ACTGTGCCTT CTAGTTGCCA
      GATTTACGAT CTCGAGCGAC TAGTCGGAGC TGACACGGAA GATCAACGGT
1851  GCCATCTGTT GTTTGCCCCT CCCCCGTGCC TTCCTTGACC CTGGAAGGTG
      CGGTAGACAA CAAACGGGGA GGGGGCACGG AAGGAACTGG GACCTTCCAC
1901  CCACTCCCAC TGTCCTTTCC TAATAAAATG AGGAAATTGC ATCGCATTGT
      GGTGAGGGTG ACAGGAAAGG ATTATTTTAC TCCTTTAACG TAGCGTAACA
1951  CTGAGTAGGT GTCATTCTAT TCTGGGGGGT GGGGTGGGGC AGGACAGCAA
      GACTCATCCA CAGTAAGATA AGACCCCCCA CCCCACCCCG TCCTGTCGTT
2001  GGGGGAGGAT TGGGAAGACA ATAGCAGGCA TGCTGGGGAT GCGGTGGGCT
      CCCCCTCCTA ACCCTTCTGT TATCGTCCGT ACGACCCCTA CGCCACCCGA
2051  CTATGGCTTC TGAGGCGGAA AGAACCAGCT GGGGCTCTAG GGGGTATCCC
      GATACCGAAG ACTCCGCCTT TCTTGGTCGA CCCCGAGATC CCCCATAGGG
2101  CACGCGCCCT GTAGCGGCGC ATTAAGCGCG GCGGGTGTGG TGGTTACGCG
      GTGCGCGGGA CATCGCCGCG TAATTCGCGC CGCCCACACC ACCAATGCGC
2151  CAGCGTGACC GCTACACTTG CCAGCGCCCT AGCGCCCGCT CCTTTCGCTT
      GTCGCACTGG CGATGTGAAC GGTCGCGGGA TCGCGGGCGA GGAAAGCGAA
2201  TCTTCCCTTC CTTTCTCGCC ACGTTCGCCG GCCTCTCAA AAAAGGGAAA
      AGAAGGGAAG GAAAGAGCGG TGCAAGCGGC CGGAGAGTT TTTTCCCTTT
2251  AAAAGCATGC ATCTCAATTA GTCAGCAACC ATAGTCCCGC CCCTAACTCC
      TTTTCGTACG TAGAGTTAAT CAGTCGTTGG TATCAGGGCG GGGATTGAGG
2301  GCCCATCCCG CCCCTAACTC CGCCCAGTTC CGCCCATTCT CCGCCCCATG
      CGGGTAGGGC GGGGATTGAG GCGGGTCAAG GCGGGTAAGA GGCGGGGTAC
2351  GCTGACTAAT TTTTTTTATT TATGCAGAGG CCGAGGCCGC CTCGGCCTCT
      CGACTGATTA AAAAAAATAA ATACGTCTCC GGCTCCGGCG GAGCCGGAGA
2401  GAGCTATTCC AGAAGTAGTG AGGAGGCTTT TTTGGAGGCC TAGGCTTTTG
      CTCGATAAGG TCTTCATCAC TCCTCCGAAA AAACCTCCGG ATCCGAAAAC
2451  CAAAAAGCTT GGGGGGACAG CTCAGGGCTG CGATTTCGCG CCAAACTTGA
      GTTTTTCGAA CCCCCCTGTC GAGTCCCGAC GCTAAAGCGC GGTTTGAACT
2501  CGGCAATCCT AGCGTGAAGG CTGGTAGGAT TTTATCCCCG CTGCCATCAT
      GCCGTTAGGA TCGCACTTCC GACCATCCTA AAATAGGGGC GACGGTAGTA
2551  GGTTCGACCA TTGAACTGCA TCGTCGCCGT GTCCCAAAAT ATGGGGATTG
      CCAAGCTGGT AACTTGACGT AGCAGCGGCA CAGGGTTTTA TACCCCTAAC
```

FIG. 4C

```
2601  GCAAGAACGG AGACCTACCC TGGCCTCCGC TCAGGAACGA GTTCAAGTAC
      CGTTCTTGCC TCTGGATGGG ACCGGAGGCG AGTCCTTGCT CAAGTTCATG
2651  TTCCAAAGAA TGACCACAAC CTCTTCAGTG GAAGGTAAAC AGAATCTGGT
      AAGGTTTCTT ACTGGTGTTG GAGAAGTCAC CTTCCATTTG TCTTAGACCA
2701  GATTATGGGT AGGAAAACCT GGTTCTCCAT TCCTGAGAAG AATCGACCTT
      CTAATACCCA TCCTTTTGGA CCAAGAGGTA AGGACTCTTC TTAGCTGGAA
2751  TAAAGGACAG AATTAATATA GTTCTCAGTA GAGAACTCAA AGAACCACCA
      ATTTCCTGTC TTAATTATAT CAAGAGTCAT CTCTTGAGTT TCTTGGTGGT
2801  CGAGGAGCTC ATTTTCTTGC AAAAGTTTG GATGATGCCT TAAGACTTAT
      GCTCCTCGAG TAAAAGAACG TTTTCAAAC CTACTACGGA ATTCTGAATA
2851  TGAACAACCG GAATTGGCAA GTAAAGTAGA CATGGTTTGG ATAGTCGGAG
      ACTTGTTGGC CTTAACCGTT CATTTCATCT GTACCAAACC TATCAGCCTC
2901  GCAGTTCTGT TTACCAGGAA GCCATGAATC AACCAGGCCA CCTCAGACTC
      CGTCAAGACA AATGGTCCTT CGGTACTTAG TTGGTCCGGT GGAGTCTGAG
2951  TTTGTGACAA GGATCATGCA GGAATTTGAA AGTGACACGT TTTTCCCAGA
      AAACACTGTT CCTAGTACGT CCTTAAACTT TCACTGTGCA AAAAGGGTCT
3001  AATTGATTTG GGGAAATATA AACTTCTCCC AGAATACCCA GGCGTCCTCT
      TTAACTAAAC CCCTTTATAT TTGAAGAGGG TCTTATGGGT CCGCAGGAGA
3051  CTGAGGTCCA GGAGGAAAAA GGCATCAAGT ATAAGTTTGA AGTCTACGAG
      GACTCCAGGT CCTCCTTTTT CCGTAGTTCA TATTCAAACT TCAGATGCTC
3101  AAGAAAGACT AACAGGAAGA TGCTTTCAAG TTCTCTGCTC CCCTCCTAAA
      TTCTTTCTGA TTGTCCTTCT ACGAAAGTTC AAGAGACGAG GGGAGGATTT
3151  GCTATGCATT TTTATAAGAC CATGGGACTT TTGCTGGCTT TAGATCTGAT
      CGATACGTAA AAATATTCTG GTACCCTGAA AACGACCGAA ATCTAGACTA
3201  CTTTGTGAAG GAACCTTACT TCTGTGGTGT GACATAATTG GACAAACTAC
      GAAACACTTC CTTGGAATGA AGACACCACA CTGTATTAAC CTGTTTGATG
3251  CTACAGAGAT TTAAAGCTCT AAGGTAAATA TAAAATTTTT AAGTGTATAA
      GATGTCTCTA AATTTCGAGA TTCCATTTAT ATTTTAAAAA TTCACATATT
3301  TGTGTTAAAC TACTGATTCT AATTGTTTGT GTATTTTAGA TTCCAACCTA
      ACACAATTTG ATGACTAAGA TTAACAAACA CATAAAATCT AAGGTTGGAT
3351  TGGAACTGAT GAATGGGAGC AGTGGTGGAA TGCCTTTAAT GAGGAAAACC
      ACCTTGACTA CTTACCCTCG TCACCACCTT ACGGAAATTA CTCCTTTTGG
3401  TGTTTTGCTC AGAAGAAATG CCATCTAGTG ATGATGAGGC TACTGCTGAC
      ACAAAACGAG TCTTCTTTAC GGTAGATCAC TACTACTCCG ATGACGACTG
3451  TCTCAACATT CTACTCCTCC AAAAAAGAAG AGAAAGGTAG AAGACCCCAA
      AGAGTTGTAA GATGAGGAGG TTTTTTCTTC TCTTTCCATC TTCTGGGGTT
3501  GGACTTTCCT TCAGAATTGC TAAGTTTTTT GAGTCATGCT GTGTTTAGTA
      CCTGAAAGGA AGTCTTAACG ATTCAAAAAA CTCAGTACGA CACAAATCAT
3551  ATAGAACTCT TGCTTGCTTT GCTATTTACA CCACAAAGGA AAAAGCTGCA
      TATCTTGAGA ACGAACGAAA CGATAAATGT GGTGTTTCCT TTTTCGACGT
3601  CTGCTATACA AGAAAATTAT GGAAAATATAT TCTGTAACCT TTATAAGTAG
      GACGATATGT TCTTTTAATA CCTTTTTATA AGACATTGGA ATATTCATC
3651  GCATAACAGT TATAATCATA ACATACTGTT TTTTCTTACT CCACACAGGC
      CGTATTGTCA ATATTAGTAT TGTATGACAA AAAAGAATGA GGTGTGTCCG
3701  ATAGAGTGTC TGCTATTAAT AACTATGCTC AAAAATTGTG TACCTTTAGC
      TATCTCACAG ACGATAATTA TTGATACGAG TTTTTAACAC ATGGAAATCG
3751  TTTTTAATTT GTAAAGGGGT TAATAAGGAA TATTTGATGT ATAGTGCCTT
      AAAAATTAAA CATTTCCCCA ATTATTCCTT ATAAACTACA TATCACGGAA
3801  GACTAGAGAT CGATCATAAT CAGCCATACC ACATTTGTAG AGGTTTTACT
      CTGATCTCTA GCTAGTATTA GTCGGTATGG TGTAAACATC TCCAAAATGA
3851  TGCTTTAAAA AACCTCCCAC ACCTCCCCCT GAACCTGAAA CATAAAATGA
      ACGAAATTTT TTGGAGGGTG TGGAGGGGGA CTTGGACTTT GTATTTTACT
3901  ATGCAATTGT TGTTGTTAAC TTGTTTATTG CAGCTTATAA TGGTTACAAA
      TACGTTAACA ACAACAATTG AACAAATAAC GTCGAATATT ACCAATGTTT
```

FIG. 4D

```
3951  TAAAGCAATA GCATCACAAA TTTCACAAAT AAAGCATTTT TTTCACTGCA
      ATTTCGTTAT CGTAGTGTTT AAAGTGTTTA TTTCGTAAAA AAAGTGACGT
4001  TTCTAGTTGT GGTTTGTCCA AACTCATCAA TGTATCTTAT CATGTCTGGA
      AAGATCAACA CCAAACAGGT TTGAGTAGTT ACATAGAATA GTACAGACCT
4051  TCGGCTGGAT GATCCTCCAG CGCGGGGATC TCATGCTGGA GTTCTTCGCC
      AGCCGACCTA CTAGGAGGTC GCGCCCCTAG AGTACGACCT CAAGAAGCGG
4101  CACCCCAACT TGTTTATTGC AGCTTATAAT GGTTACAAAT AAAGCAATAG
      GTGGGGTTGA ACAAATAACG TCGAATATTA CCAATGTTTA TTTCGTTATC
4151  CATCACAAAT TCACAAATA AAGCATTTTT TTCACTGCAT TCTAGTTGTG
      GTAGTGTTTA AAGTGTTTAT TCGTAAAAA AAGTGACGTA AGATCAACAC
4201  GTTTGTCCAA ACTCATCAAT GTATCTTATC ATGTCTGTAT ACCGTCGACC
      CAAACAGGTT TGAGTAGTTA CATAGAATAG TACAGACATA TGGCAGCTGG
4251  TCTAGCTAGA GCTTGGCGTA ATCATGGTCA TAGCTGTTTC CTGTGTGAAA
      AGATCGATCT CGAACCGCAT TAGTACCAGT ATCGACAAAG GACACACTTT
4301  TTGTTATCCG CTCACAATTC CACACAACAT ACGAGCCGGA AGCATAAAGT
      AACAATAGGC GAGTGTTAAG GTGTGTTGTA TGCTCGGCCT TCGTATTTCA
4351  GTAAAGCCTG GGGTGCCTAA TGAGTGAGCT AACTCACATT AATTGCGTTG
      CATTTCGGAC CCCACGGATT ACTCACTCGA TTGAGTGTAA TTAACGCAAC
4401  CGCTCACTGC CCGCTTTCCA GTCGGGAAAC CTGTCGTGCC AGCTGCATTA
      GCGAGTGACG GGCGAAAGGT CAGCCCTTTG GACAGCACGG TCGACGTAAT
4451  ATGAATCGGC CAACGCGCGG GGAGAGGCGG TTTGCGTATT GGGCGCTCTT
      TACTTAGCCG GTTGCGCGCC CCTCTCCGCC AAACGCATAA CCCGCGAGAA
4501  CCGCTTCCTC GCTCACTGAC TCGCTGCGCT CGGTCGTTCG GCTGCGGCGA
      GGCGAAGGAG CGAGTGACTG AGCGACGCGA GCCAGCAAGC CGACGCCGCT
4551  GCGGTATCAG CTCACTCAAA GGCGGTAATA CGGTTATCCA CAGAATCAGG
      CGCCATAGTC GAGTGAGTTT CCGCCATTAT GCCAATAGGT GTCTTAGTCC
4601  GGATAACGCA GGAAAGAACA TGTGAGCAAA AGGCCAGCAA AAGGCCAGGA
      CCTATTGCGT CCTTTCTTGT ACACTCGTTT TCCGGTCGTT TTCCGGTCCT
4651  ACCGTAAAAA GGCCGCGTTG CTGGCGTTTT TCCATAGGCT CCGCCCCCCT
      TGGCATTTTT CCGGCGCAAC GACCGCAAAA AGGTATCCGA GGCGGGGGGA
4701  GACGAGCATC ACAAAAATCG ACGCTCAAGT CAGAGGTGGC GAAACCCGAC
      CTGCTCGTAG TGTTTTTAGC TGCGAGTTCA GTCTCCACCG CTTTGGGCTG
4751  AGGACTATAA AGATACCAGG CGTTTCCCCC TGGAAGCTCC CTCGTGCGCT
      TCCTGATATT TCTATGGTCC GCAAAGGGGG ACCTTCGAGG GAGCACGCGA
4801  CTCCTGTTCC GACCCTGCCG CTTACCGGAT ACCTGTCCGC CTTTCTCCCT
      GAGGACAAGG CTGGGACGGC GAATGGCCTA TGGACAGGCG GAAAGAGGGA
4851  TCGGGAAGCG TGGCGCTTTC TCATAGCTCA CGCTGTAGGT ATCTCAGTTC
      AGCCCTTCGC ACCGCGAAAG AGTATCGAGT GCGACATCCA TAGAGTCAAG
4901  GGTGTAGGTC GTTCGCTCCA AGCTGGGCTG TGTGCACGAA CCCCCCGTTC
      CCACATCCAG CAAGCGAGGT TCGACCCGAC ACACGTGCTT GGGGGGCAAG
4951  AGCCCGACCG CTGCGCCTTA TCCGGTAACT ATCGTCTTGA GTCCAACCCG
      TCGGGCTGGC GACGCGGAAT AGGCCATTGA TAGCAGAACT CAGGTTGGGC
5001  GTAAGACACG ACTTATCGCC ACTGGCAGCA GCCACTGGTA ACAGGATTAG
      CATTCTGTGC TGAATAGCGG TGACCGTCGT CGGTGACCAT TGTCCTAATC
5051  CAGAGCGAGG TATGTAGGCG GTGCTACAGA GTTCTTGAAG TGGTGGCCTA
      GTCTCGCTCC ATACATCCGC CACGATGTCT CAAGAACTTC ACCACCGGAT
5101  ACTACGGCTA CACTAGAAGG AACAGTATTT GGTATCTGCG CTCTGCTGAA
      TGATGCCGAT GTGATCTTCC TTGTCATAAA CCATAGACGC GAGACGACTT
5151  GCCAGTTACC TTCGGAAAAA GAGTTGGTAG CTCTTGATCC GGCAAACAAA
      CGGTCAATGG AAGCCTTTTT CTCAACCATC GAGAACTAGG CCGTTTGTTT
5201  CCACCGCTGG TAGCGGTGGT TTTTTTGTTT GCAAGCAGCA GATTACGCGC
      GGTGGCGACC ATCGCCACCA AAAAACAAA CGTTCGTCGT CTAATGCGCG
5251  AGAAAAAAAG GATCTCAAGA AGATCCTTTG ATCTTTTCTA CGGGGTCTGA
      TCTTTTTTTC CTAGAGTTCT TCTAGGAAAC TAGAAAAGAT GCCCCAGACT
```

FIG. 4E

```
5301  CGCTCAGTGG AACGAAAACT CACGTTAAGG GATTTTGGTC ATGAGATTAT
      GCGAGTCACC TTGCTTTTGA GTGCAATTCC CTAAAACCAG TACTCTAATA
5351  CAAAAAGGAT CTTCACCTAG ATCCTTTTAA ATTAAAAATG AAGTTTTAAA
      GTTTTTCCTA GAAGTGGATC TAGGAAAATT TAATTTTTAC TTCAAAATTT
5401  TCAATCTAAA GTATATATGA GTAAACTTGG TCTGACAGTT ACCAATGCTT
      AGTTAGATTT CATATATACT CATTTGAACC AGACTGTCAA TGGTTACGAA
5451  AATCAGTGAG GCACCTATCT CAGCGATCTG TCTATTTCGT TCATCCATAG
      TTAGTCACTC CGTGGATAGA GTCGCTAGAC AGATAAAGCA AGTAGGTATC
5501  TTGCCTGACT CCCCGTCGTG TAGATAACTA CGATACGGGA GGGCTTACCA
      AACGGACTGA GGGGCAGCAC ATCTATTGAT GCTATGCCCT CCCGAATGGT
5551  TCTGGCCCCA GTGCTGCAAT GATACCGCGA GACCCACGCT CACCGGCTCC
      AGACCGGGGT CACGACGTTA CTATGGCGCT CTGGGTGCGA GTGGCCGAGG
5601  AGATTTATCA GCAATAAACC AGCCAGCCGG AAGGGCCGAG CGCAGAAGTG
      TCTAAATAGT CGTTATTTGG TCGGTCGGCC TTCCCGGCTC GCGTCTTCAC
5651  GTCCTGCAAC TTTATCCGCC TCCATCCAGT CTATTAATTG TTGCCGGGAA
      CAGGACGTTG AAATAGGCGG AGGTAGGTCA GATAATTAAC AACGGCCCTT
5701  GCTAGAGTAA GTAGTTCGCC AGTTAATAGT TTGCGCAACG TTGTTGCCAT
      CGATCTCATT CATCAAGCGG TCAATTATCA AACGCGTTGC AACAACGGTA
5751  TGCTACAGGC ATCGTGGTGT CACGCTCGTC GTTTGGTATG GCTTCATTCA
      ACGATGTCCG TAGCACCACA GTGCGAGCAG CAAACCATAC CGAAGTAAGT
5801  GCTCCGGTTC CCAACGATCA AGGCGAGTTA CATGATCCCC CATGTTGTGC
      CGAGGCCAAG GGTTGCTAGT TCCGCTCAAT GTACTAGGGG GTACAACACG
5851  AAAAAAGCGG TTAGCTCCTT CGGTCCTCCG ATCGTTGTCA GAAGTAAGTT
      TTTTTTCGCC AATCGAGGAA GCCAGGAGGC TAGCAACAGT CTTCATTCAA
5901  GGCCGCAGTG TTATCACTCA TGGTTATGGC AGCACTGCAT AATTCTCTTA
      CCGGCGTCAC AATAGTGAGT ACCAATACCG TCGTGACGTA TTAAGAGAAT
5951  CTGTCATGCC ATCCGTAAGA TGCTTTTCTG TGACTGGTGA GTACTCAACC
      GACAGTACGG TAGGCATTCT ACGAAAAGAC ACTGACCACT CATGAGTTGG
6001  AAGTCATTCT GAGAATAGTG TATGCGGCGA CCGAGTTGCT CTTGCCCGGC
      TTCAGTAAGA CTCTTATCAC ATACGCCGCT GGCTCAACGA GAACGGGCCG
6051  GTCAATACGG GATAATACCG CGCCACATAG CAGAACTTTA AAAGTGCTCA
      CAGTTATGCC CTATTATGGC GCGGTGTATC GTCTTGAAAT TTTCACGAGT
6101  TCATTGGAAA ACGTTCTTCG GGGCGAAAAC TCTCAAGGAT CTTACCGCTG
      AGTAACCTTT TGCAAGAAGC CCCGCTTTTG AGAGTTCCTA GAATGGCGAC
6151  TTGAGATCCA GTTCGATGTA ACCCACTCGT GCACCCAACT GATCTTCAGC
      AACTCTAGGT CAAGCTACAT TGGGTGAGCA CGTGGGTTGA CTAGAAGTCG
6201  ATCTTTTACT TTCACCAGCG TTTCTGGGTG AGCAAAAACA GGAAGGCAAA
      TAGAAAATGA AAGTGGTCGC AAAGACCCAC TCGTTTTGT CCTTCCGTTT
6251  ATGCCGCAAA AAAGGGAATA AGGGCGACAC GGAAATGTTG AATACTCATA
      TACGGCGTTT TTTCCCTTAT TCCCGCTGTG CCTTTACAAC TTATGAGTAT
6301  CTCTTCCTTT TTCAATATTA TTGAAGCATT TATCAGGGTT ATTGTCTCAT
      GAGAAGGAAA AAGTTATAAT AACTTCGTAA ATAGTCCCAA TAACAGAGTA
6351  GAGCGGATAC ATATTTGAAT GTATTTAGAA AAATAAACAA ATAGGGGTTC
      CTCGCCTATG TATAAACTTA CATAAATCTT TTTATTTGTT TATCCCCAAG
6401  CGCGCACATT TCCCCGAAAA GTGCCACCTG ACGTC
      GCGCGTGTAA AGGGGCTTTT CACGGTGGAC TGCAG
```

FIG. 4F

20H4.9-IgG1 Heavy Chain

20H4.9 Light chain

```
                        natural Ig leader peptide
         ~~~~~~~~~~~~~~~~~~~~~~~~~~~~~~~~~~~~~~~~~~~~~~~~~~~
          M   K   H   L   W   F   F   L   L   L   V   A   A   P   R   W   V  ·
    1   ATGAAACACC TGTGGTTCTT CCTCCTCCTG GTGGCAGCTC CCAGATGGGT
        TACTTTGTGG ACACCAAGAA GGAGGAGGAC CACCGTCGAG GGTCTACCCA ~~~~~~~
                        20H4.9 HC variable region
         ~~~~~~~~~~~~~~~~~~~~~~~~~~~~~~~~~~~~~~~~~~~~~~~~~~~
         ·  L   S   Q   V   Q   L   Q   Q   W   G   A   G   L   L   K   P   S  ·
    51  CCTGTCCCAG GTGCAACTAC AGCAGTGGGG CGCAGGACTG TTGAAGCCTT
        GGACAGGGTC CACGTTGATG TCGTCACCCC GCGTCCTGAC AACTTCGGAA
                                                                        CDR 1
                                                                          ~~~
                        20H4.9 HC variable region
         ~~~~~~~~~~~~~~~~~~~~~~~~~~~~~~~~~~~~~~~~~~~~~~~~~~~
         ·  E   T   L   S   L   T   C   A   V   Y   G   G   S   F   S   G
   101  CGGAGACCCT GTCCCTCACC TGCGCTGTCT ATGGTGGGTC CTTCAGTGGT
        GCCTCTGGGA CAGGGAGTGG ACGCGACAGA TACCACCCAG GAAGTCACCA
             CDR 1
        ~~~~~~~~~~~~~~
                        20H4.9 HC variable region
         ~~~~~~~~~~~~~~~~~~~~~~~~~~~~~~~~~~~~~~~~~~~~~~~~~~~
          Y   Y   W   S   W   I   R   Q   S   P   E   K   G   L   E   W   I  ·
   151  TACTACTGGA GCTGGATACG CCAGTCCCCA GAGAAGGGGC TGGAGTGGAT
        ATGATGACCT CGACCTATGC GGTCAGGGGT CTCTTCCCCG ACCTCACCTA
                                         CDR 2
                ~~~~~~~~~~~~~~~~~~~~~~~~~~~~~~~~~~~~~~~~~~~~~~~~~~
                        20H4.9 HC variable region
         ~~~~~~~~~~~~~~~~~~~~~~~~~~~~~~~~~~~~~~~~~~~~~~~~~~~
         ·  G   E   I   N   H   G   G   Y   V   T   Y   N   P   S   L   E   S  ·
   201  TGGGGAAATC AATCATGGTG GATACGTCAC CTACAATCCG TCCCTCGAGA
        ACCCCTTTAG TTAGTACCAC CTATGCAGTG GATGTTAGGC AGGGAGCTCT
        CDR 2
        ~~
                        20H4.9 HC variable region
         ~~~~~~~~~~~~~~~~~~~~~~~~~~~~~~~~~~~~~~~~~~~~~~~~~~~
         ·  R   V   T   I   S   V   D   T   S   K   N   Q   F   S   L   K
   251  GTCGAGTCAC CATATCAGTA GACACGTCCA AGAACCAGTT CTCCCTGAAG
        CAGCTCAGTG GTATAGTCAT CTGTGCAGGT TCTTGGTCAA GAGGGACTTC
                                                                        CDR 3
                                                                          ~~
                        20H4.9 HC variable region
         ~~~~~~~~~~~~~~~~~~~~~~~~~~~~~~~~~~~~~~~~~~~~~~~~~~~
          L   S   S   V   T   A   A   D   T   A   V   Y   Y   C   A   R   D  ·
   301  CTGAGCTCTG TGACCGCCGC GGACACGGCT GTATATTACT GTGCGAGGGA
        GACTCGAGAC ACTGGCGGCG CCTGTGCCGA CATATAATGA CACGCTCCCT
                                                       CDR 3
         ~~~~~~~~~~~~~~~~~~~~~~~~~~~~~~~~~~~~~~~~~~~~
                        20H4.9 HC variable region
         ~~~~~~~~~~~~~~~~~~~~~~~~~~~~~~~~~~~~~~~~~~~~~~~~~~~
         ·  Y   G   P   G   N   Y   D   W   Y   F   D   L   W   G   R   G   T  ·
   351  CTATGGTCCG GGGAATTATG ACTGGTACTT CGATCTCTGG GGCCGTGGCA
        GATACCAGGC CCCTTAATAC TGACCATGAA GCTAGAGACC CCGGCACCGT
```

FIG. 7A

```
                                        IgG1 CH1 domain
                                        ~~~~~~~~~~~~~~~~~~~~~~~~~~~~~~~~~
      20H4.9 HC variable region
      ~~~~~~~~~~~~~~~~~~~~~~
         · L   V   T   V   S   S   A   S   T   K   G   P   S   V   F   P
      401  CCCTGGTCAC TGTCTCCTCA GCCTCCACCA AGGGCCCATC GGTCTTCCCC
           GGGACCAGTG ACAGAGGAGT CGGAGGTGGT TCCCGGGTAG CCAGAAGGGG
                                        IgG1 CH1 domain
                              ~~~~~~~~~~~~~~~~~~~~~~~~~~~~~~~~~~~~~~
            L   A   P   S   S   K   S   T   S   G   G   T   A   A   L   G   C   ·
      451  CTGGCACCCT CCTCCAAGAG CACCTCTGGG GGCACAGCGG CCCTGGGCTG
           GACCGTGGGA GGAGGTTCTC GTGGAGACCC CCGTGTCGCC GGGACCCGAC
                                        IgG1 CH1 domain
                              ~~~~~~~~~~~~~~~~~~~~~~~~~~~~~~~~~~~~~~
         · L   V   K   D   Y   F   P   E   P   V   T   V   S   W   N   S   G   ·
      501  CCTGGTCAAG GACTACTTCC CCGAACCGGT GACGGTGTCG TGGAACTCAG
           GGACCAGTTC CTGATGAAGG GGCTTGGCCA CTGCCACAGC ACCTTGAGTC
                                        IgG1 CH1 domain
                              ~~~~~~~~~~~~~~~~~~~~~~~~~~~~~~~~~~~~~~
         · A   L   T   S   G   V   H   T   F   P   A   V   L   Q   S   S
      551  GCGCCCTGAC CAGCGGCGTG CACACCTTCC CGGCTGTCCT ACAGTCCTCA
           CGCGGGACTG GTCGCCGCAC GTGTGGAAGG GCCGACAGGA TGTCAGGAGT
                                        IgG1 CH1 domain
                              ~~~~~~~~~~~~~~~~~~~~~~~~~~~~~~~~~~~~~~
            G   L   Y   S   L   S   S   V   V   T   V   P   S   S   S   L   G   ·
      601  GGACTCTACT CCCTCAGCAG CGTGGTGACC GTGCCCTCCA GCAGCTTGGG
           CCTGAGATGA GGGAGTCGTC GCACCACTGG CACGGGAGGT CGTCGAACCC
                                        IgG1 CH1 domain
                              ~~~~~~~~~~~~~~~~~~~~~~~~~~~~~~~~~~~~~~
         · T   Q   T   Y   I   C   N   V   N   H   K   P   S   N   T   K   V   ·
      651  CACCCAGACC TACATCTGCA ACGTGAATCA CAAGCCCAGC AACACCAAGG
           GTGGGTCTGG ATGTAGACGT TGCACTTAGT GTTCGGGTCG TTGTGGTTCC
           IgG1 CH1 domain
           ~~~~~~~~~~~~~
                                        IgG1 hinge region
                                        ~~~~~~~~~~~~~~~~~~~~~~~~~~~~~~~
         · D   K   R   V   E   P   K   S   C   D   K   T   H   T   C   P
      701  TGGACAAGAG AGTTGAGCCC AAATCTTGTG ACAAAACTCA CACATGCCCA
           ACCTGTTCTC TCAACTCGGG TTTAGAACAC TGTTTTGAGT GTGTACGGGT
                                        IgG1 CH2 domain
                                        ~~~~~~~~~~~~~~~~~~~~~~~~~~~~~~~
      IgG1 hinge region
      ~~~~~~~~~~~
            P   C   P   A   P   E   L   L   G   G   P   S   V   F   L   F   P   ·
      751  CCGTGCCCAG CACCTGAACT CCTGGGGGGA CCGTCAGTCT TCCTCTTCCC
           GGCACGGGTC GTGGACTTGA GGACCCCCCT GGCAGTCAGA AGGAGAAGGG
                                        IgG1 CH2 domain
                              ~~~~~~~~~~~~~~~~~~~~~~~~~~~~~~~~~~~~~~
         · P   K   P   K   D   T   L   M   I   S   R   T   P   E   V   T   C   ·
      801  CCCAAAACCC AAGGACACCC TCATGATCTC CCGGACCCCT GAGGTCACAT
           GGGTTTTGGG TTCCTGTGGG AGTACTAGAG GGCCTGGGGA CTCCAGTGTA
```

FIG. 7B

```
                    IgG1 CH2 domain
       ~~~~~~~~~~~~~~~~~~~~~~~~~~~~~~~~~~~~~~~~~~~~~~~~~~~
         ·  V   V   V   D   V   S   H   E   D   P   E   V   K   F   N   W
 851   GCGTGGTGGT GGACGTGAGC CACGAAGACC CTGAGGTCAA GTTCAACTGG
       CGCACCACCA CCTGCACTCG GTGCTTCTGG GACTCCAGTT CAAGTTGACC
                    IgG1 CH2 domain
       ~~~~~~~~~~~~~~~~~~~~~~~~~~~~~~~~~~~~~~~~~~~~~~~~~~~
          Y   V   D   G   V   E   V   H   N   A   K   T   K   P   R   E   E  ·
 901   TACGTGGACG GCGTGGAGGT GCATAATGCC AAGACAAAGC CGCGGGAGGA
       ATGCACCTGC CGCACCTCCA CGTATTACGG TTCTGTTTCG GCGCCCTCCT
                    IgG1 CH2 domain
       ~~~~~~~~~~~~~~~~~~~~~~~~~~~~~~~~~~~~~~~~~~~~~~~~~~~
         ·  Q   Y   N   S   T   Y   R   V   V   S   V   L   T   V   L   H   Q  ·
 951   GCAGTACAAC AGCACGTACC GTGTGGTCAG CGTCCTCACC GTCCTGCACC
       CGTCATGTTG TCGTGCATGG CACACCAGTC GCAGGAGTGG CAGGACGTGG
                    IgG1 CH2 domain
       ~~~~~~~~~~~~~~~~~~~~~~~~~~~~~~~~~~~~~~~~~~~~~~~~~~~
         ·  D   W   L   N   G   K   E   Y   K   C   K   V   S   N   K   A
1001   AGGACTGGCT GAATGGCAAG GAGTACAAGT GCAAGGTCTC CAACAAAGCC
       TCCTGACCGA CTTACCGTTC CTCATGTTCA CGTTCCAGAG GTTGTTTCGG
                                                           IgG1 CH3 domain
                                                           ~~~~~~~~~~~~~
              IgG1 CH2 domain
       ~~~~~~~~~~~~~~~~~~~~~~~~~~~~~~~~~~~~~~~~~~~~~~~
          L   P   A   P   I   E   K   T   I   S   K   A   K   G   Q   P   R  ·
1051   CTCCCAGCCC CCATCGAGAA AACCATCTCC AAAGCCAAAG GGCAGCCCCG
       GAGGGTCGGG GGTAGCTCTT TTGGTAGAGG TTTCGGTTTC CCGTCGGGGC
                    IgG1 CH3 domain
       ~~~~~~~~~~~~~~~~~~~~~~~~~~~~~~~~~~~~~~~~~~~~~~~~~~~
         ·  E   P   Q   V   Y   T   L   P   P   S   R   D   E   L   T   K   N  ·
1101   AGAACCACAG GTGTACACCC TGCCCCCATC CCGGGATGAG CTGACCAAGA
       TCTTGGTGTC CACATGTGGG ACGGGGGTAG GGCCCTACTC GACTGGTTCT
                    IgG1 CH3 domain
       ~~~~~~~~~~~~~~~~~~~~~~~~~~~~~~~~~~~~~~~~~~~~~~~~~~~
         ·  Q   V   S   L   T   C   L   V   K   G   F   Y   P   S   D   I
1151   ACCAGGTCAG CCTGACCTGC CTGGTCAAAG GCTTCTATCC CAGCGACATC
       TGGTCCAGTC GGACTGGACG GACCAGTTTC CGAAGATAGG GTCGCTGTAG
                    IgG1 CH3 domain
       ~~~~~~~~~~~~~~~~~~~~~~~~~~~~~~~~~~~~~~~~~~~~~~~~~~~
          A   V   E   W   E   S   N   G   Q   P   E   N   N   Y   K   T   T  ·
1201   GCCGTGGAGT GGGAGAGCAA TGGGCAGCCG GAGAACAACT ACAAGACCAC
       CGGCACCTCA CCCTCTCGTT ACCCGTCGGC CTCTTGTTGA TGTTCTGGTG
                    IgG1 CH3 domain
       ~~~~~~~~~~~~~~~~~~~~~~~~~~~~~~~~~~~~~~~~~~~~~~~~~~~
         ·  P   P   V   L   D   S   D   G   S   F   F   L   Y   S   K   L   T  ·
1251   GCCTCCCGTG CTGGACTCCG ACGGCTCCTT CTTCCTCTAC AGCAAGCTCA
       CGGAGGGCAC GACCTGAGGC TGCCGAGGAA GAAGGAGATG TCGTTCGAGT
                    IgG1 CH3 domain
       ~~~~~~~~~~~~~~~~~~~~~~~~~~~~~~~~~~~~~~~~~~~~~~~~~~~
         ·  V   D   K   S   R   W   Q   Q   G   N   V   F   S   C   S   V
1301   CCGTGGACAA GAGCAGGTGG CAGCAGGGGA ACGTCTTCTC ATGCTCCGTG
       GGCACCTGTT CTCGTCCACC GTCGTCCCCT TGCAGAAGAG TACGAGGCAC
```

FIG. 7C

```
              IgG1 CH3 domain
       ~~~~~~~~~~~~~~~~~~~~~~~~~~~~~~~~~~~~~~~~~~~~~~~~~~~~
         M   H   E   A   L   H   N   H   Y   T   Q   K   S   L   S   L   S ·
  1351  ATGCATGAGG CTCTGCACAA CCACTACACG CAGAAGAGCC TCTCCCTGTC
        TACGTACTCC GAGACGTGTT GGTGATGTGC GTCTTCTCGG AGAGGGACAG
        IgG1 CH3 domain
        ~~~~~~~~~~~~
         ·  P   G   K
  1401  CCCGGGTAAA TGA
        GGGCCCATTT ACT
```

FIG. 7D

FULLY HUMAN ANTIBODIES AGAINST HUMAN 4-1BB

This application is a continuation of U.S. application Ser. No. 13/368,710 filed on Feb. 8, 2012, and published as US2012/0141494, which is a continuation of U.S. application Ser. No. 12/653,137 filed on Dec. 9, 2009, issued as U.S. Pat. No. 8,137,667, which is a continuation of U.S. Divisional application Ser. No. 11/903,106 filed on Sep. 20, 2007, issued as U.S. Pat. No. 7,659,384, which claims priority to Non-Provisional application Ser. No. 10/961,567 filed Oct. 8, 2004, issued as U.S. Pat. No. 7,288,638, which claims priority to U.S. Provisional Application No. 60/510,193, filed Oct. 10, 2003, whose contents are hereby incorporated by reference.

FIELD OF THE INVENTION

The invention is directed to fully human antibodies and, more specifically, to fully human antibodies to human 4-1BB (CD137).

BACKGROUND OF THE INVENTION

An extensive body of evidence has unequivocally demonstrated that some degree of immune response against cancer exists in humans and animals. In cancer patients, cellular components of the immune system are able to recognize antigens expressed by tumor cells, such as differentiation of oncofetal antigens or mutated gene products (S. Rosenberg, Nature, 411:380-4 (2001); P. van der Bruggen et al., Immunological Rev., 188:51-64 (2002)). A number of clinical studies have shown that tumor-infiltrating lymphocytes have favorable prognostic significance (E. Halapi, Med. Oncol., 15(4):203-11 (1998); Y. Naito et al., Cancer Res., 58(16): 3491-4 (1998); L. Zhang et al., N. E. J. Med., 348(3):203-13 (2003)). Furthermore, treatment with immunomodulators, such as cytokines or bacterial products, cancer vaccines, or adoptive immunotherapy has led to tumor regression in a number of patients (S. Rosenberg, Cancer J. Sci. Am. 6(S):2 (2000); P. Bassi, Surg. Oncol., 11(1-2):77-83 (2002); S. Antonia et al., Current Opinion in Immunol., 16:130-6 (2004)). Despite these responses, immunity against cancer frequently fails to effectively eliminate tumor cells. The causes for this failure can be grouped into three major categories: (i) impaired tumor recognition by immune cells, either by variable expression of tumor antigens or reduced expression of class I major histocompatibility complex (MHC); (ii) immunosuppressive tumor microenvironment, as a result of secretion of inhibitory cytokines by tumor cells (e.g., TGF-β); and (iii) poor tumor immunogenicity due to the lack of expression of co-stimulatory molecules on tumor cells, which results in the inability of the tumor cells to effectively stimulate T-cells. Advances in our understanding of the requirements for tumor antigen recognition and immune effector function indicate that a potential strategy to enhance an anti-tumor immune response is to provide co-stimulation through an auxiliary molecule. Tumor antigen-specific T-cells require costimulation to initiate and maintain effector functions. Thus, therapies that target costimulatory molecules can be applied to modulate and enhance the immune response to tumors.

The current model for T-cell activation postulates that naive T-cells require two signals for full activation: (i) a signal provided through the binding of processed antigens presented to the T-cell receptor by major histocompatibility complex (MHC) class I molecules; and (ii) an additional signal provided by the interaction of co-stimulatory molecules on the surface of T-cells and their ligands on antigen presenting cells. Recognition of an antigen by a naive T-cell is insufficient in itself to trigger T-cell activation. Without a co-stimulatory signal, T-cells may be eliminated either by death or by induction of anergy. Signaling through the CD28 costimulatory molecule appears to be key for the initiation of T-cell responses. However, CD137 (4-1BB) signaling has been shown to be primordial for the maintenance and expansion of the immune response to antigens, as well as, for the generation of memory T-cells.

CD137 (4-1BB) is a member of the tumor necrosis receptor (TNF-R) gene family, which includes proteins involved in regulation of cell proliferation, differentiation, and programmed cell death. CD137 is a 30 kDa type I membrane glycoprotein expressed as a 55 kDa homodimer. The receptor was initially described in mice (B. Kwon et al., P.N.A.S. USA, 86:1963-7 (1989)), and later identified in humans (M. Alderson et al., Eur. J. Immunol., 24: 2219-27 (1994); Z. Zhou et al., Immunol. Lett., 45:67 (1995)) (See, also, Published PCT Applications WO95/07984 and WO96/29348, and U.S. Pat. No. 6,569,997, hereby incorporated by reference (See, SEQ ID NO:2.)). The human and murine forms of CD137 are 60% identical at the amino acid level. Conserved sequences occur in the cytoplasmic domain, as well as 5 other regions of the molecule, indicating that these residues might be important for function of the CD137 molecule (Z. Zhou et al., Immunol. Lett., 45:67 (1995)). Expression of CD137 has been shown to be predominantly on cells of lymphoid lineage such as activated T-cells, activated Natural Killer (NK) cells, NKT-cells, CD4CD25 regulatory T-cells, and also on activated thymocytes, and intraepithelial lymphocytes. In addition, CD137 has also been shown to be expressed on cells of myeloid origin like dendritic cells, monocytes, neutrophils, and eosinophils. Even though CD137 expression is mainly restricted to immune/inflammatory cells, there have been reports describing its expression on endothelial cells associated with a small number of tissues from inflammatory sites and tumors.

Functional activities of CD137 on T-cells have been amply characterized. Signaling through CD137 in the presence of suboptimal doses of anti-CD3 has been demonstrated to induce T-cell proliferation and cytokine synthesis (mainly IFN-γ), and to inhibit activated cell death. These effects have been observed with both murine and human T-cells (W. Shuford et al., J. Exp. Med., 186(1):47-55 (1997); D. Vinay et al., Semin. Immunol., 10(6):481-9 (1998); D. Laderach et al., Int. Immunol., 14(10):1155-67 (2002)). In both humans and mice, co-stimulation enhances effector functions, such as IFN-γ production and cytotoxicity, by augmenting the numbers of antigen-specific and effector CD8+ T-cells. In the absence of anti-CD3 signaling, stimulation through CD137 does not alter T-cell function, indicating that CD137 is a co-stimulatory molecule.

The physiological events observed following CD137 stimulation on T-cells are mediated by NF-κB and PI3K/ERK1/2 signals with separate physiological functions. NF-κB signals trigger expression of Bcl-$_{XL}$, an anti-apoptotic molecule, thus resulting in increased survival, whereas PI3K and ERK1/2 signals are specifically responsible for CD137-mediated cell cycle progression (H. Lee et al., J. Immunol., 169(9):4882-8 (2002)). The effect of CD137 activation on the inhibition of activation-induced cell death was shown in vitro by Hurtado et al. (J. Hurtado et al., J. Immunol., 158(6): 2600-9 (1997)), and in an in vivo system in which anti-CD137 monoclonal antibodies (mabs) were shown to produce long-term survival of superantigen-activated CD8+ T-cells by preventing clonal deletion (C. Takahashi et al., J. Immunol., 162:5037 (1999)). Later, two reports demonstrated, under different experimental conditions, that the CD137 signal regulated both clonal expansion and survival of CD8+ T-cells (D. Cooper et al., Eur. J. Immunol., 32(2):521-9 (2002); M. Maus et al., Nat. Biotechnol., 20:143 (2002)). Reduced apoptosis observed after co-stimulation correlated with increased levels of Bcl-$_{xL}$ in CD8+ T-cells, while Bcl-2 expression remained unchanged. Up-regulation of the anti-apoptotic genes Bcl-$_{xL}$ and bfl-1 via 4-1BB was shown to be mediated by NF-κB activation, since PDTC, an NF-κB-specific blocker, inhibited 4-1BB-mediated up-regulation of Bcl-$_{xL}$ (H. Lee et al., J. Immunol., 169(9):4882-8 (2002)). On the other hand, clonal expansion of activated T-cells appears to be mediated by increased expression of cyclins D2, D3, and E, and down-regulation of the p27$^{kip1}$ protein. This effect occurs in both an IL-2 dependent and independent fashion (H. Lee et al., J. Immunol., 169(9):4882-8 (2002)).

Altogether, CD137 stimulation results in enhanced expansion, survival, and effector functions of newly primed CD8+ T-cells, acting, in part, directly on these cells. Both CD4+ and CD8+ T-cells have been shown to respond to CD137 stimulation, however, it appears that enhancement of T-cell function is greater in CD8+ cells (W. Shuford et al., J. Exp. Med., 186(1):47-55 (1997); I. Gramaglia et al., Eur. J. Immunol., 30(2):392-402 (2000); C. Takahashi et al., J. Immunol., 162: 5037 (1999)). Based on the critical role of CD137 stimulation in CD8+ T-cell function and survival, manipulation of the CD137/CD137L system provides a plausible approach for the treatment of tumors and viral pathogens.

Recently, the constitutive expression of CD137 on freshly isolated dendritic cells (DCs) was demonstrated in mice (R. Wilcox et al., J. Immunol., 169(8):4230-6 (2002); T. Futagawa et al., Int. Immunol., 14(3):275-86 (2002)) and humans (S. Pauly et al., J. Leukoc. Biol. 72(1):35-42 (2002)). These reports showed that stimulation of CD137 on DCs resulted in secretion of IL-6 and IL-12, and, more importantly, it enhanced DC ability to stimulate T-cell responses to alloantigens. Furthermore, Pan et al. demonstrated that CD137 signaling in DCs resulted in upregulation of MHC Class I and costimulatory molecules, and produced an increased ability of DCs to infiltrate tumors (P. Pan et al., J. Immunol., 172(8): 4779-89 (2004)). Therefore, CD137 costimulation on DCs appears to be a novel pathway for proliferation, maturation, and migration of DCs.

Activated Natural Killer (NK) cells express CD137 following stimulation with cytokines (I. Melero et al., Cell Immunol., 190(2):167-72 (1998); R. Wilcox et al., J. Immunol., 169(8):4230-6 (2002)). Several reports demonstrated that NK cells appear to be critical for the modulation of the antitumor immune response induced by agonistic CD137 antibodies ((I. Melero et al., Cell Immunol., 190(2):167-72 (1998); R. Miller et al., J. Immunol, 169(4):1792-800 (2002); R. Wilcox et al., J. Immunol., 169(8):4230-6 (2002)). Depletion of NK cells significantly reduces the antitumor activity of anti-CD137 mabs. Ligation of CD137 on NK cells induces proliferation and IFN-γ secretion, but does not affect their cytolytic activity. Notably, in vitro, CD137-stimulated NK cells presented an immunoregulatory or "helper" activity for CD8+ cytolytic T-cells resulting in expansion of activated T-cells. Therefore, CD137 signaling on NK cells may modulate innate immunity to tumors.

A paradoxical effect has been described for CD137 stimulation in that agonistic CD137 antibodies can induce suppression of the humoral responses to T-cell antigens in primates and mouse models (H. Hong et al., J. Immunother., 23(6): 613-21 (2000); R. Mittler et al., J. Exp. Med., 190(10):1535-40 (1999)). Notably, CD137 agonistic antibodies were shown to produce significant amelioration of the symptoms associated with antibody dependent autoimmune diseases such as systemic lupus erythematosus and experimental autoimmune encephalomyelitis (J. Foell et al., N.Y. Acad. Sci., 987:230-5 (2003); Y. Sun et al., Nat. Med., 8(12):1405-13 (2002)). Recently, Seo et al. demonstrated that, in a mouse model of rheumatoid arthritis, treatment with an agonistic anti-CD137 antibody prevented the development of the disease, and remarkably, blocked disease progression (S. K. Seo et al., Nat. Med. 10; 1099-94 (2004)). The mechanism responsible for this effect has not been well defined, but in the model of rheumatoid arthritis it was shown that treatment with a CD137 agonistic antibody resulted in the expansion of IFN-γ-producing CD11C-CD8+ T cells. IFN-γ in turn stimulated dendritic cells to produce indolamine-2,3-dioxygenase (IDO), which exerts immuno-suppressive activities. It has also been postulated that CD137 signaling on antigen-activated CD4+ T-cells results in induction of IFN-γ secretion which activates macrophages. Activated macrophages can in turn produce death signals for B cells. Continuous signaling through CD137 on CD4+ T-cells may subsequently induce activation-induced cell death (AICD) of these CD4+ activated T-cells. Therefore, by eliminating antigen-activated T-cells and B cells, a reduced antibody response is observed and, consequently, a dramatic reduction of Th2-mediated inflammatory diseases is observed (B. Kwon et al., J. Immunol., 168(11):5483-90 (2002)). These studies suggest a role for the use of agonistic CD137 antibodies for the treatment of inflammatory or autoimmune diseases, without inducing a general suppression of the immune system.

The natural ligand for CD137, CD137 ligand (CD137L), a 34 kDa glycoprotein member of the TNF superfamily, is detected mainly on activated antigen-presenting cells (APC), such as B cells, macrophages, dendritic cells, and also on murine B-cell lymphomas, activated T-cells, and human carcinoma lines of epithelial origin (R. Goodwin et al., Eur. J. Immunol., 23(10):2631-41 (1993); Z. Zhou et al., Immunol. Lett., 45:67 (1995); H. Salih et al., J. Immunol., 165(5):2903-10 (2000)). Human CD137L shares 36% homology with its murine counterpart (M. Alderson et al., Eur. J. Immunol., 24: 2219-27 (1994)).

In addition to delivering signals to CD137-expressing cells, binding of CD137 to CD137L initiates a bidirectional signal resulting in functional effects on CD137L-expressing cells. Langstein et al. demonstrated that binding of CD137-Ig fusion protein to CD137L on activated monocytes induced the production of IL-6, IL-8, and TNF-α, upregulated ICAM, and inhibited IL-10, resulting in increased adherence (J. Langstein et al., J. Immunol., 160(5):2488-94 (1998)). In addition, proliferation of monocytes was demonstrated along with a higher rate of apoptosis (J. Langstein et al., J. Leukoc. Biol., 65(6):829-33 (1999)). These observations were confirmed by the studies of Ju et al. (S. Ju et al., Hybrid Hybridomics, 22(5):333-8 (2003)), which showed that a functional anti-CD137L antibody induced a high rate of proliferation of peripheral blood monocytes. Blocking the ligand resulted in inhibition of T-cell activation. In addition, soluble CD137L was found in the serum of patients with rheumatoid arthritis and hematological malignancies (H. Salih et al., J. Immunol., 167(7):4059-66 (2001)). Thus, the interaction of CD137 with CD137L influences and produces functional effects on T-cells and APC.

In another important aspect of T-cell function, it has been demonstrated that agonistic anti-CD137 antibodies rescued T-cell responses to protein antigens in aged mice. It has been well documented that an age-related decline in the immune response to antigens occurs, a process known as immunosenescence (R. Miller, Science, 273:70-4 (1996); R. Miller, Vaccine, 18:1654-60 (2000); F. Hakim et al., Curr. Opinion Immunol., 16:151-156 (2004)). This phenomenon appears to be due to alterations in the equilibrium between the extent of cellular expansion and cellular survival or death. Bansal-Pakala et al. tested the hypothesis that secondary costimulation through CD137 can be used to enhance T-cell responses in situations where T-cells do not receive sufficient stimulation, due to either reduced expression of CD3 or CD28, or reduced quality of signals. Their studies showed that aged mice had a deficient in vitro recall response compared to young mice (P. Bansal-Pakala et al., J. Immunol., 169(9): 5005-9 (2002)). However, when aged mice were treated with anti-CD137 mabs, the proliferative and cytokine responses of T-cells were identical to the responses observed in young mice. While the specific mechanism responsible for this effect was not elucidated, it was speculated that enhancing both the expression of anti-apoptotic molecules like Bcl-$_{XL}$, and the promotion of IL-2 secretion in vivo may play a role in rescuing defective T-cell responses. These studies demonstrated the potential for agonistic anti-CD137 antibodies to rescue weak T-cell responses in elderly immuno-compromised individuals, and has profound implications for the use of anti-CD137 antibodies in cancer patients.

A role for CD137 targeted therapy in the treatment of cancer was suggested by in vivo efficacy studies in mice utilizing agonistic anti-murine CD137 monoclonal antibodies. In a paper by Melero et al., agonistic anti-mouse CD137 antibody produced cures in P815 mastocytoma tumors, and in the low immunogenic tumor model Ag104 (I. Melero et al., Nat. Med., 3(6):682-5 (1997)). The anti-tumor effect required both CD4+ and CD8+ T-cells and NK cells, since selective in vivo depletion of each subpopulation resulted in the reduction or complete loss of the anti-tumor effect. It was also demonstrated that a minimal induction of an immune response was necessary for anti-CD137 therapy to be effective. Several investigators have used anti-CD137 antibodies to demonstrate the viability of this approach for cancer therapy (J. Kim et al., Cancer Res., 61(5):2031-7 (2001); O. Martinet et al., Gene Ther., 9(12):786-92 (2002); R. Miller et al., J. Immunol., 169(4):1792-800 (2002); R. Wilcox et al., Cancer Res., 62(15):4413-8 (2002)).

In support of the anti-tumor efficacy data with agonistic CD137 antibodies, signals provided by CD137L have been shown to elicit CTL activity and anti-tumor responses (M. DeBenedette et al., J. Immunol., 163(9):4833-41 (1999); B. Guinn et al., J. Immunol., 162(8):5003-10 (1999)). Several reports demonstrated that gene transfer of CD137 ligand into murine carcinomas resulted in tumor rejection, demonstrating the requirement of costimulation in generating an efficient immune response (S. Mogi et al., Immunology, 101(4):541-7 (2000); I. Melero et al., Cell Immunol., 190(2):167-72 (1998); B. Guinn et al., J. Immunol., 162(8):5003-10 (1999)). Salih et al. reported the expression of CD137L in human carcinomas and human carcinoma cell lines (H. Salih et al., J. Immunol., 165(5):2903-10 (2000)), and demonstrated that tumors cells expressing the ligand were able to deliver a co-stimulatory signal to T-cells which resulted in the release of IFN-γ and IL-2, and that this effect correlated with the levels of CD137L on tumors. Whether expression of CD137L in human tumors could make these tumors more susceptible to agonistic CD137 antibodies is not known.

CD137L−/− mice have underscored the importance of the CD137/CD137L system in T-cell responses to both viruses and tumors (M. DeBenedette et al., J. Immunol., 163(9): 4833-41 (1999); J. Tan et al., J. Immunol., 164(5):2320-5 (2000); B. Kwon et al., J. Immunol., 168(11):5483-90 (2002)). Studies using CD137- and CD137L-deficient mice have demonstrated the importance of CD137 costimulation in graft-vs-host disease, and anti-viral cytolytic T-cell responses. CD137-deficient mice had an enhanced proliferation of T-cells, but a reduction in cytokine production and cytotoxic T-cell activity (B. Kwon et al., J. Immunol., 168 (11):5483-90 (2002); D. Vinay et al., Immunol. Cell Biol., 81(3):176-84 (2003)). More recently, it was shown that knockout mice (CD137−/−) had a higher frequency of tumor metastases (4-fold) compared to control mice. These data suggest that restoration of CD137 signaling by the use of agonistic anti-CD137 antibodies is a feasible approach for augmenting cellular immune responses to viral pathogens and cancers.

In addition to the data in mouse in vivo models which supports the involvement of CD137 signaling in antitumor immune responses, studies conducted in primary human tumor samples have confirmed the role of CD137 in generating effector T-cells. In patients with Ewing sarcoma, Zhang et al. showed that intratumoral effector T-cells presented the CD3+/CD8+/CD28−/CD137+ phenotype. Unexpectedly, coexistence of progressive tumor growth and anti-tumor immunity (effector T-cells) was observed. Ex vivo stimulation studies with patients' cells demonstrated that tumor-induced T-cell proliferation and activation required costimulation with CD137L. Stimulation of PBL with anti-CD3/CD137L, but not anti-CD3/anti-CD28, induced tumor lytic effectors. These studies provided further evidence that CD137 mediated costimulation could result in expansion of tumor reactive CTLs (H. Zhang et al., Cancer Biol. Ther., 2(5):579-86 (2003)). Furthermore, expression of CD137 was demonstrated in tumor infiltrating lymphocytes in hepatocellular carcinomas (HCC) (Y. Wan et al., World J. Gastroenterol, 10(2):195-9 (2004)). CD137 expression was detected in 19 out of 19 HCC by RT-PCR, and in 13/19 by immunofluorescence staining. Conversely, CD137 was not detected in the peripheral mononuclear cells of the same patients. Analyses conducted in healthy donor liver tissues failed to demonstrate expression of CD137. These studies did not attempt to correlate clinical disease with CD137 expression. Thus, studies conducted in Ewing sarcoma and hepatocellular carcinoma revealed the presence of TIL that express CD137, with concomitant disease progression. In Ewing sarcomas it was demonstrated that CD137+TILs were able to kill tumor cells ex-vivo suggesting that the CD137 pathway was intact in these patients, and that perhaps suppressive factors in the tumor microenvironment inhibited their function. Hence, it can be postulated that systemic administration of agonistic CD137 antibodies may provide the signal necessary for expansion of these effector T-cells.

In addition to its role in the development of immunity to cancer, experimental data supports the use of CD137 agonistic antibodies for the treatment of autoimmune and viral diseases (B. Kwon et al., Exp. Mol. Med., 35(1):8-16 (2003); H. Salih et al., J. Immunol., 167(7):4059-66 (2001); E. Kwon et al., P.N.A.S. USA, 96:15074-79 (1999); J. Foell et al., N.Y. Acad. Sci., 987:230-5 (2003); Y. Sun et al., Nat. Med., 8(12): 1405-13 (2002) S. K. Seo et al, Nat. Med. 10; 1099-94 (2004)).

Consequently, based on the roles of 4-1BB in modulating immune response, it would be desirable to produce anti-human 4-1BB antibodies with agonistic activities that could be used for the treatment or prevention of human diseases such as cancer, infectious diseases, and autoimmune diseases.

BRIEF SUMMARY OF THE INVENTION

The present invention provides fully human antibodies that bind to human 4-1BB (H4-1BB) and that allow binding of H4-1BB to a human 4-1BB ligand (H4-1BBL). Thus, the invention is directed to antibodies that bind to H4-1BB and that do not block the binding of H4-1BB to H4-1BBL, thereby permitting the binding of both an antibody of the invention and H4-1BBL to H4-1BB. The invention also provides antibodies with agonistic activities in that binding of the antibodies to H4-1BB results in an enhancement and stimulation of H4-1BB mediated immune responses. These antibodies can be used as immuno-enhancers of an anti-tumor or anti-viral immune response, or as immunomodulators of T cell mediated autoimmune diseases. The antibodies can also be used as diagnostic tools for the detection of H4-1BB in blood or tissues of patients with cancer, autoimmune, or other diseases.

In one aspect, the invention provides a monoclonal antibody or antigen-binding portion thereof that specifically binds to H4-1BB, comprising a light chain variable region and a heavy chain variable region, wherein the light chain variable region comprises a CDR1 (complementary determining region 1), a CDR2 (complementary determining region 2), and a CDR3 (complementary determining region 3) as depicted in FIG. 4, and the heavy chain variable region comprises a CDR1 (complementary determining region 1), a CDR2 (complementary determining region 2), and a CDR3 (complementary determining region 3) as depicted in FIG. 3 or FIG. 7. The monoclonal antibody (mab) can be, for example, an IgG4 antibody or IgG1 antibody.

In another aspect, the invention provides a monoclonal antibody or antigen-binding portion thereof, wherein the light chain comprises a variable region as depicted in FIG. 4, and the heavy chain comprises a variable region as depicted in FIG. 3 or FIG. 7.

In another aspect, the invention provides a monoclonal antibody comprising a light chain and a heavy chain, wherein the light chain comprises amino acid residues 21-236 of SEQ ID NO:6 and the heavy chain comprises amino acid residues 20-467 of SEQ ID NO:3. In another aspect, the invention provides a monoclonal antibody comprising a light chain and a heavy chain, wherein the light chain comprises amino acid residues 21-236 of SEQ ID NO:6 and the heavy chain comprises amino acid residues 20-470 of SEQ ID NO:9.

The antibodies of the invention have wide therapeutic applications as immunomodulators of diseases such as cancer, autoimmune diseases, inflammatory diseases, and infectious diseases.

The invention further provides methods for treating cancer in a subject comprising administering a therapeutically effective amount of an antibody of the invention to the subject. In one aspect, this method further comprises administering a vaccine. Suitable vaccines include, for example, a tumor cell vaccine, a DNA vaccine, a GM-CSF-modified tumor cell vaccine, or an antigen-loaded dendritic cell vaccine. The cancer can be, for example, prostate cancer, melanoma, or epithelial cancer.

In another aspect, the invention provides a method for enhancing the immune response, comprising administration of an antibody of the invention and a SIV gag vaccine. In another aspect, the invention provides a method for enhancing the immune response, comprising administration of an antibody of the invention and a PSA vaccine. In another aspect, the invention provides a method for enhancing the immune response to a SIV gag vaccine, comprising administration of an antibody of the invention. In another aspect, the invention provides a method for enhancing the immune response to a PSA vaccine, comprising administration of an antibody of the invention.

The invention also provides pharmaceutical compositions comprising an antibody of the invention, or an antigen-binding portion thereof, and a pharmaceutically acceptable carrier. The pharmaceutical composition can be administered alone or in combination with an agent, e.g., an agent for treating cancer such as a chemotherapeutic agent or a vaccine or other immunomodulatory agent.

The invention also provides isolated polynucleotides comprising a nucleotide sequence selected from: (a) nucleotides that encode the amino acid sequence of amino acid residues 20-467 of SEQ ID NO:3; (b) nucleotides that encode the amino acid sequence of SEQ ID NO:3; (c) nucleotides that encode the amino acid sequence of amino acid residues 21-236 of SEQ ID NO:6; (d) nucleotides that encode the amino acid sequence of SEQ ID NO:6; (e) nucleotides that encode the amino acid sequence of amino acid residues 20-470 of SEQ ID NO:9; (f) nucleotides that encode the amino acid sequence of SEQ ID NO:9; and (g) nucleotides that encode a fragment of an amino acid sequence of (a) to (f), such as a variable region, constant region, or one or more CDRs. The isolated polynucleotides of the invention further comprise nucleotide sequences encoding at least one CDR of FIG. 3, at least one CDR of FIG. 4, or at least one CDR of FIG. 7. The invention further provides isolated polynucleotides that comprise the nucleotide sequence of SEQ ID NO:1, SEQ ID NO:4, or SEQ ID NO:7.

The invention also provides isolated polypeptides comprising an amino acid sequence selected from the group consisting of SEQ ID NO:3, SEQ ID NO:6, and SEQ ID NO:9. In another aspect, the invention provides isolated polypeptides comprising the amino acid sequence of amino acid residues 20-467 of SEQ ID NO:3, isolated polypeptides comprising the amino acid sequence of amino acid residues 21-236 of SEQ ID NO:6, and isolated polypeptides comprising the amino acid sequence of amino acid residues 20-470 of SEQ ID NO:9. In another aspect, the invention provides isolated polypeptides comprising the amino acid sequence of at least one CDR of FIG. 3, FIG. 4, or FIG. 7, or at least the variable or constant region of FIG. 3, FIG. 4, or FIG. 7.

The invention further includes an immunoglobulin having binding specificity for H4-1BB, said immunoglobulin comprising an antigen binding region. In one aspect, the immunoglobulin is a Fab or F(ab')$_2$ of an antibody of the invention.

The invention also includes a cell line that produces an antibody or antigen-binding portion thereof of the invention, recombinant expression vectors that include the nucleotides of the invention, and methods to make the antibodies of the invention by culturing an antibody-producing cell line.

BRIEF DESCRIPTION OF THE DRAWINGS

FIG. 1 shows a plasmid map of pD17-20H4.9.h4a.

FIG. 3 (FIGS. 3A-3H) shows the nucleotide sequence of the plasmid pD17-20H4.9.h4a, including the coding strand (SEQ ID NO:1), complementary strand (SEQ ID NO:2), and amino acid sequence (leader peptide is amino acid residues 1-19 of SEQ ID NO:3; heavy chain is amino acid residues 20-467 of SEQ ID NO:3) encoded by the coding strand.

FIG. 4 (FIGS. 4A-4F) shows the nucleotide sequence of the plasmid pD16gate-20H4.9.LC, including the coding strand (SEQ ID NO:4), complementary strand (SEQ ID NO:5), and amino acid sequence (leader peptide is amino acid residues 1-20 of SEQ ID NO:6; light chain is amino acid residues 21-236 of SEQ ID NO:6) encoded by the coding strand.

FIG. 7 (FIGS. 7A-7D shows the nucleotide and amino acid sequences of the 20H4.9-IgG1 heavy chain construct, including the coding strand (SEQ ID NO:7), complementary strand (SEQ ID NO:8), and amino acid sequence (leader peptide is amino acid residues 1-19 of SEQ ID NO:9; heavy chain is amino acid residues 20-470 of SEQ ID NO:9) encoded by the coding strand.

DETAILED DESCRIPTION OF THE INVENTION

The invention is directed to the preparation and characterization of antibodies, and antigen binding fragments thereof (including fusion proteins that comprise an antigen binding fragment of an antibody of the invention), for use in the treatment of a disease, such as a cancer, infectious disease, inflammatory disease, or autoimmune disease. The cancer can be, for example, prostate cancer, melanoma, or epithelial cancer.

The antibodies are capable of binding to H4-1BB, and can present high affinity for H4-1BB and effectively enhance T cell responses. In one aspect, the antibody induces IFN-γ production in co-stimulatory assays, but does not affect the binding of H4-1BB to its corresponding ligand, H4-1BBL, and does not fix complement.

The antibodies of the invention may be produced by methods well known in the art. In one aspect, the antibodies can be produced by expression in transfected cells, such as immortalized eukaryotic cells, such as myeloma or hybridoma cells.

The antibodies of the invention may be used alone, or together with other therapeutic agents such as radiotherapy (including radiation), hormonal therapy, cytotoxic agents, vaccines, and other immunomodulatory agents, such us cytokines and biological response modifiers. These agents are particularly useful in treating cancer and immune-proliferative disorders.

Figure 1:
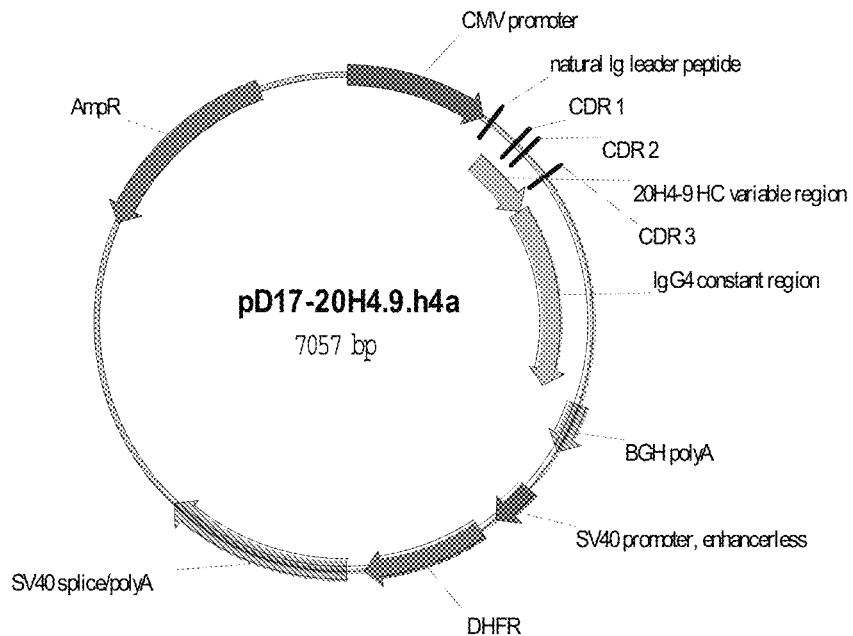
Figure 2:
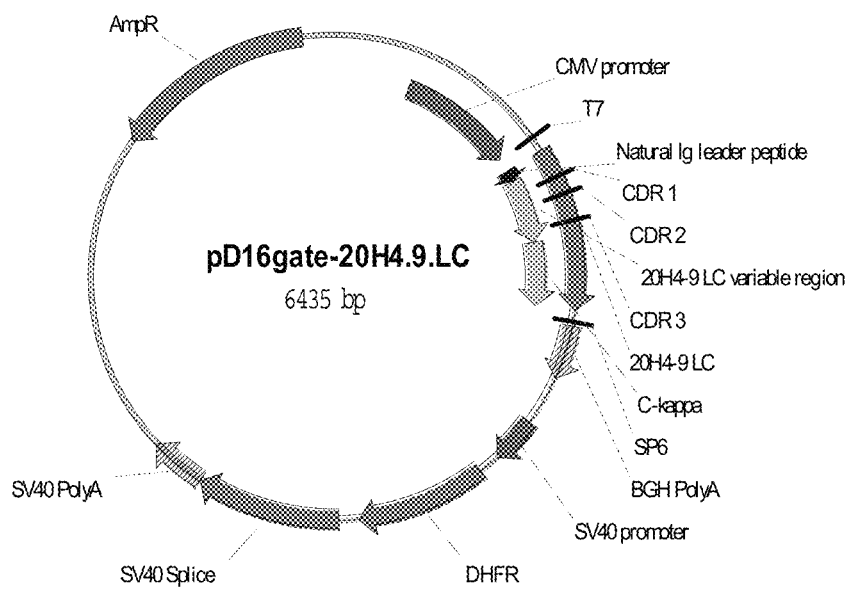
FIG. 2 shows a plasmid map of pD16gate-20H4.9.LC.

In one aspect, the invention provides the monoclonal antibody (mab) 20H4.9-IgG4. FIGS. 1 and 2 provide plasmid maps of pD17-20H4.9.h4a and pD16gate-20H4.9.LC, respectively, that can be used to produce mab 20H4.9-IgG4. FIG. 3 (FIGS. 3A-3H) provides the nucleotide sequence of the plasmid pD17-20H4.9.h4a, including the coding strand (SEQ ID NO:1), complementary strand (SEQ ID NO:2), and amino acid sequence (leader peptide is amino acid residues 1-19 of SEQ ID NO:3; heavy chain is amino acid residues 20-467 of SEQ ID NO:3) encoded by the coding strand. FIG. 4 (FIGS. 4A-4F) shows the nucleotide sequence of the plasmid pD16gate-20H4.9.LC, including the coding strand (SEQ ID NO:4), complementary strand (SEQ ID NO:5), and amino acid sequence (leader peptide is amino acid residues 1-20 of SEQ ID NO:6; light chain is amino acid residues 21-236 of SEQ ID NO:6) encoded by the coding strand.

Figure 5:
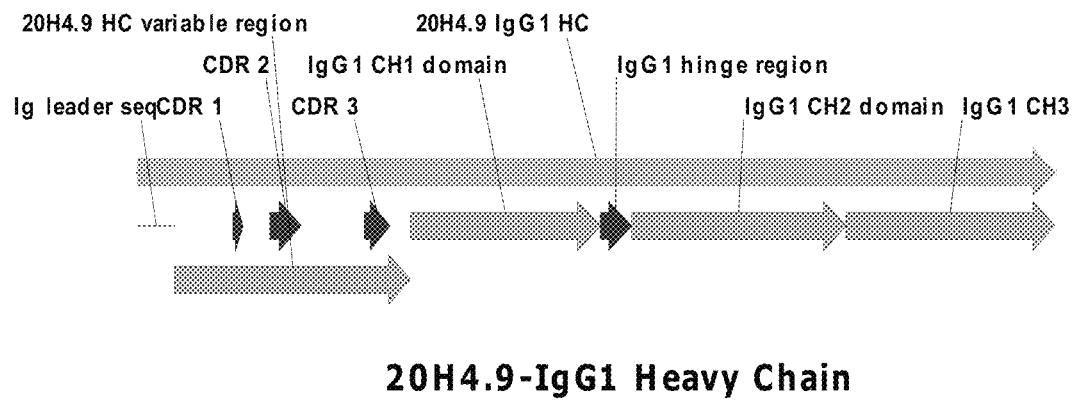
FIG. 5 shows a schematic of the 20H4.9-IgG1 heavy chain sequence construct.
Figure 6:
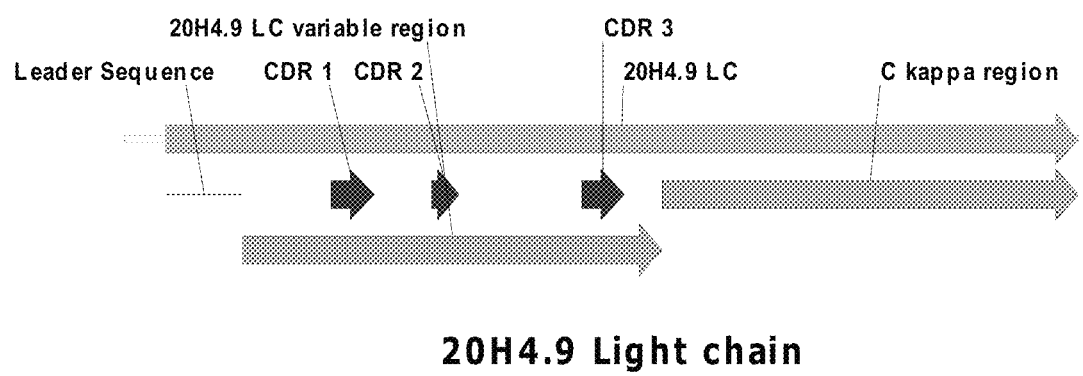
FIG. 6 shows a schematic of the 20H4.9 light chain sequence construct.

In another aspect, the invention provides the monoclonal antibody (mab) 20H4.9-IgG1. FIG. 5 schematically shows a heavy chain sequence construct of mab 20H4.9-IgG1. FIG. 6 schematically shows a light chain sequence construct of mab 20H4.9, for both mab 20H4.9-IgG4 and 20 H4.9-IgG1. FIG. 7 provides the nucleotide sequence (coding strand (SEQ ID NO:7) and complementary strand (SEQ ID NO:8)) of the heavy chain sequence construct of FIG. 5, and the amino acid sequence (leader peptide is amino acid residues 1-19 of SEQ ID NO:9; heavy chain is amino acid residues 20-470 of SEQ ID NO:9) encoded by the coding strand. The light chain of mab 20H4.9-IgG1 is the same as the light chain of mab 20H4.9-IgG4.

The invention also encompasses antibodies with conservative amino acid substitutions from the heavy and light chain amino acid sequences depicted in SEQ ID NOS:3, 6, and 9 that have substantially no effect on H4-1BB binding. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine.

The polynucleotides encoding the polypeptides of the invention typically further comprise an expression control sequence operably linked to the polypeptide coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into an appropriate host, the host is maintained under conditions suitable for high level expression of the nucleotide sequences and, as desired, the collection and purification of the light chain, heavy chain, light/heavy chain dimers or intact antibody, binding fragments or other immunoglobulin form may follow. (See, S. Beychok, Cells of Immunoglobulin Synthesis, Academic Press, N.Y. (1979)). Single chain antibodies or minibodies (single chain antibodies fused to one or more CH domains) may also be produced by joining nucleic acid sequences encoding the VL and VH regions disclosed herein with DNA encoding a polypeptide linker.

Prokaryotic hosts, such as *E. coli*, and other microbes, such as yeast, may be used to express an antibody of the invention. In addition to microorganisms, mammalian tissue cell culture may also be used to express and produce the antibodies of the invention. Eukaryotic cells may be preferred, because a number of suitable host cell lines capable of secreting intact immunoglobulins have been developed including, for example, CHO (chinese hamster ovary) cell lines, COS (African green monkey fibroblast cell line) cell lines, HeLa cells, myeloma cell lines, and hybridomas. Expression vectors for these cells can include expression control sequences, such as a promoter or enhancer, and necessary processing information sites, such as ribosome binding sites, RNA splice sites, polyadenylation sites, and transcriptional terminator sequences, all well known in the art.

The vectors containing the DNA segments of interest (e.g., the heavy and/or light chain encoding sequences and expression control sequences) can be transferred into the host cell by well-known methods, which vary depending on the type of cellular host. For example, calcium chloride transfection is commonly used for prokaryotic cells, whereas calcium phosphate treatment, lipofection, or electroporation may be used for other cellular hosts. (See, e.g., T. Maniatis et al., Molecular Cloning: A Laboratory Manual, Cold Spring Harbor Press (1982)).

Once expressed, the antibodies, their dimers, individual light and heavy chains, or other immunoglobulin forms, can be purified according to standard procedures in the art, such as ammonium sulfate precipitation, affinity columns, column chromatography, gel electrophoresis, and the like. Substantially pure immunoglobulins of at least 90 to 95% homogeneity are desirable, and 98 to 99% or more homogeneity are more desirable.

The antibodies of the invention are useful for modulating T cell and antibody-mediated immune responses. Typical disease states suitable for treatment include cancers, infectious diseases, inflammatory diseases, and autoimmune diseases such as multiple sclerosis, rheumatoid arthritis, systemic lupus erythematosus, and myaesthenia gravis.

The invention also provides pharmaceutical compositions comprising at least one antibody of the invention and a pharmaceutically acceptable carrier. The pharmaceutical compositions may be sterilized by conventional well known sterilization techniques. The pharmaceutical compositions can also contain pharmaceutically acceptable auxiliary substances as required to approximate physiological conditions such as pH adjusting and buffering agents, stability enhancing agents such as mannitol or tween 80, toxicity adjusting agents and the like, for example, sodium acetate, sodium chloride, potassium chloride, calcium chloride, sodium lactate, or human albumin.

The antibodies and pharmaceutical compositions of the invention are particularly useful for parenteral administration, including subcutaneous, intramuscular, and intravenous administration. The pharmaceutical compositions for parenteral administration can comprise a solution of the antibody dissolved in an acceptable carrier, preferably an aqueous carrier. A variety of aqueous carriers can be used, all well known in the art, e.g., water, buffered water, saline, glycine and the like. These solutions are sterile and generally free of particulate matter. It is especially advantageous to formulate parenteral compositions in dosage unit form for ease of administration and uniformity of dosage.

The pharmaceutical composition can further comprise an additional agent for treatment of a disease. In one aspect, the pharmaceutical composition includes an agent for treatment of a cancer, an infectious disease, inflammatory disease, or autoimmune disease. The antibody of the invention can also be co-administered or separately administered with an additional agent for treatment of a disease.

The antibodies of the invention can be used with other agents to enhance the immune response to cancerous cells in a patient. In one aspect, the antibody is used in combination with an immunogenic agent, such as cancerous cells, purified tumor antigens (including recombinant proteins, peptides, and carbohydrate molecules), or cells transfected with genes encoding immune stimulating cytokines and cell surface antigens. In another aspect, the antibody is used in combination with a vaccine such as, for example, a tumor cell vaccine, a DNA vaccine, a gene-modified tumor cell vaccine, such as GM-CSF-modified tumor cell vaccine, a peptide vaccine, or an antigen-loaded dendritic cell vaccine.

Many experimental strategies for vaccination against tumors have been devised. In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al., P.N.A.S., 90:3539-43 (1993); E. Jafee et al., J. Clin. Oncol., 19:145-56 (2001); R. Salgia et al., J. Clin. Oncol., 21:624-30 (2003)).

The study of gene expression and large scale gene expression patterns in various tumors has led to the definition of so called tumor specific antigens (S. Rosenberg, Immunity 10:281-7 (1999)). In many cases, these tumor specific antigens are differentiation antigens expressed in the tumors and in the cell from which the tumor arose, for example melanocyte antigens gp 100, MAGE antigens, Trp-2. Many of these antigens can be shown to be the targets of tumor specific T cells found in the host. The antibodies of the invention may be used in conjunction with a collection of recombinant proteins and/or peptides expressed in a tumor in order to amplify and direct the immune response to these antigens towards a Th1 response. These proteins are normally viewed by the immune system as self antigens and are therefore tolerant to them.

In one aspect of the invention, the antibody is combined with an immunodulatory agent comprising the SIV gag antigen (as a model for HIV DNA vaccine) or prostate specific antigen (PSA), or a DNA vaccine comprising a nucleotide sequence that encodes the SIV gag antigen or prostate specific antigen (PSA). PSA vaccines are described in, for example, M. Pavlenko et al., Br. J. Cancer, 91(4):688-94 (2004); J. Wolchok et al., Semin. Oncol., 30(5):659-66 (2003); J. Kim et al., Clin. Cancer Res., 7(3 Suppl.):882s-889s (2001). SIV gag vaccines are described in, for example, B. Makitalo et al., J. Gen. Virol., 85(Pt 8):2407-19 (2004); N. Letvin et al., J. Virol., 78(14):7490-7 (2004); S. Mossman et al., AIDS Res. Hum. Retroviruses., 20(4):425-34 (2004); F. Bertley et al., J.

Immunol., 172(6):3745-57 (2004); L. Patterson et al., J. Virol., 78(5):2212-21 (2004); E. O'Neill et al., AIDS Res. Hum. Retroviruses, 19(10):883-90 (2003); Z. Bu et al., Virology, 309(2):272-81 (2003).

The tumor antigen may also include, for example, the protein telomerase, which is required for the synthesis of telomeres of chromosomes and which is expressed in more than 85% of human cancers and in only a limited number of somatic tissues (N. Kim et al., Science, 266, 2011-2013 (1994)). Tumor antigen may also be "neo-antigens" expressed in cancer cells because of somatic mutations that alter protein sequence or create fusion proteins between two unrelated sequences, or idiotype from B cell tumors. Other tumor vaccines may include the proteins from viruses implicated in human cancers such a Human Papilloma Viruses (HPV), Hepatitis Viruses (HBV and HCV), and Kaposi's Herpes Sarcoma Virus (KHSV). Another form of tumor specific antigen which may be used with an antibody of the invention is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (R. Suot et al., Science 269: 1585-1588 (1995); Y. Tamura et al., Science 278: 117-120 (1997)).

The antibodies of the invention can also be used to enhance the immune response to vaccines to viral antigens, such as HIV or HCV. The antibodies of the invention can also be used to enhance the immune response to other immunomodulatory agents, and to elicit a memory immune response. Examples of these agents are cytokines such as GM-CSF, IL-2, IL-15, IL-12, F13 ligand, CD40 ligand, adjuvants such as CpG-oligodeoxynucleotide (bacterial DNA), or antibodies to OX-40 or CTLA-4.

The pharmaceutical compositions of the invention can be administered for prophylactic and/or therapeutic treatments. In therapeutic application, the pharmaceutical composition is administered to a patient already suffering from a disease, in an amount sufficient to cure or at least partially arrest or treat the disease. An amount adequate to accomplish this is defined as a "therapeutically effective dose." Amounts effective for this use will depend upon the severity of the disease state and the patient (including, for example, the general state of the patient's own immune system), and can be determined by one skilled in the art. In prophylactic applications, the pharmaceutical composition is administered to a patient not already in the disease state, to enhance the patient's resistance to the disease state. Such an amount is defined to be a "prophylactically effective dose." In this use, the precise amounts depend upon the patient's state of health (including, for example, the general state of the patient's own immune system), and can be determined by one skilled in the art. In one aspect, the prophylactic use is for the prevention of tumor recurrence.

EXAMPLES

Example 1

Generation of Antibodies

Materials and Methods

Fully human monoclonal antibodies to the human CD137 (4-1BB) receptor were generated in the HuMAb-Mouse® (Medarex, Inc., Princeton, N.J.). HuMAb mice were immunized five times intraperitoneally (i.p.) and subcutaneously (s.c.) with 25 µg of the extracellular domain of human CD137 in RIBI adjuvant (Ribi Immunochemical). Prior to fusion, mice were boosted intravenously (i.v.) with the same amount of antigen. Spleen cells from immunized mice with adequate titers of antibodies to huCD137 were fused to mouse myeloma cells following standard procedures.

Anti-human CD3 mab (clone:HIT3a), ELISA kits for human and monkey IFN-γ, cytometric bead array (CBA) kits, and all conjugated antibodies for flow cytometry were purchased from BD Pharmingen (San Diego, Calif.). Human $IgG_1$ λ and Human $IgG_1$ κ were purchased from Sigma-Aldrich (St. Louis, Mo.). CEM cells (ATCC-CRL 2265) were purchased from ATCC. Culture media (RPMI), and fetal bovine serum (FBS) were purchased from Mediatech Inc. (Herndon, Va.). Sheep Red Blood Alsevers was purchased from Colorado Serum Co. (Denver, Colo.).

Hybridoma screening: Detection of binding to huCD137 by ELISA: To identify hybridomas secreting anti-human CD137 antibodies, ELISA plates (Nunc MaxiSorp) were coated with human CD137-mouse $IgG_{2b}$ fusion protein at 1 µg/ml in PBS overnight at 4° C. Plates were then washed 3 times with PBS with 0.01% Tween-80 (PBS-T), and subsequently blocked with PBS-T plus 1% bovine serum albumin (BSA), for 20 min at room temperature. Fifty microliters of supernatants diluted 1:3 in PBS-T were added to the plates and incubated for 1-2 hr at ambient temperature. Afterwards, plates were washed as before, and binding of antibodies was detected by an incubation with alkaline phosphatase-conjugated goat F(ab')$_2$ anti-human IgG antibody (Jackson Laboratories, West Grove, Pa.). Plates were developed with pNPP and read at 405 nm.

Blocking assay: Twenty-six hybridomas secreting antibodies that recognized huCD137 by ELISA were evaluated for their ability to allow CD137-CD137L interactions. These analyses were conducted initially in an ELISA format. Plates were coated with human CD137-muIgG$_{2b}$ at 0.2 µg/ml, 100 µl/well. Serial dilutions of the mab 20H4.9-IgG1, or control antibodies, diluted in PBS-T and 1% bovine serum albumin, were added to the plate. CD137L-CD8 fusion protein was added to the wells at a concentration of 0.2 µg/ml. Binding of antibodies was detected with a biotinylated anti-CD8 antibody (0.2 µg/ml, Ancell Corporation, Bayport, Minn.). After several washes, streptavidin-alkaline phosphatase (1:2000) and pNPP for the detection of bound antibodies were added, and the plates were read at 405 nm.

To confirm that the selected antibodies did not alter CD137-CD137L binding, purified antibodies were further characterized by BIAcore analyses. All experiments were carried out on a BIAcore 3000 instrument (BIAcore Inc., Piscataway, N.J.). Human CD137 was immobilized covalently at a high density on a carboxy-methylated dextran surface of a BIAcore sensorchip (BIAcore Inc., Piscataway, N.J.). Injections were conducted at 2 µg/mL in 10 mM acetate buffer, pH 5.0. Unoccupied active esters were subsequently blocked by injection of an excess of ethanolamine Regeneration of the surface was done with 10 mM glycine, pH 2.0.

Purified samples of anti-CD137 antibodies were diluted to concentrations between 200 and 1000 nM using HEPES buffered saline, pH 7.4, supplemented with 0.15 M NaCl and 0.005% surfactant P20 (HBS-EP). Human CD137L-CD8 fusion proteins (huCD137L) were used as source of CD137 ligand. Experiments were conducted in which huCD137L was injected prior to anti-CD137 antibodies, or vice versa. Injections were performed at a flow rate of 5 µL/min. Bound ligand and antibodies were removed by regeneration with 10 mM glycine buffer, pH 2.0.

Human T-cell purification: T-cells or PBMCs were obtained from healthy human donors. Blood was collected in EDTA, suspended in elutriation buffer (RPMI containing 2.5 mM EDTA, 10 µg/ml polymyxin B), underlayed with Lymphocyte Separation Medium (LSM, Mediatech Inc., Herndon, Va.), and centrifuged at 1800 rpm for 25 minutes. Cellular interfaces were collected, and centrifuged at 1500 rpm for 10 minutes. Afterwards, cell pellets were resuspended in elutriation buffer and washed Sheep Red Blood Cells (SRBC, 1:10 dilution), and incubated on ice for 1 hour. Cells were then underlayed with LSM and centrifuged at 2500 rpm for 25 minutes. Interfaces were removed and SRBC were lysed with SRBC Lysis Buffer. Isolated T-cells were washed and resuspended in 10% FBS/RPMI.

Flow Cytometric analyses: Binding of anti-human CD137 antibodies to CD137 expressed on cells was determined by flow cytometry. A human T-cell leukemia cell line (CEM) or cynomolgus monkey peripheral blood monocytic cells (PBMC) were used for these studies. These cells do not express CD137 constitutively, but the receptor can be induced by stimulation with phorbol myristate (PMA, 10 ng/ml) and ionomycin (1 µM) for 18 hr. Cells were then washed and incubated with various concentrations of the antibodies in staining buffer (phosphate buffer saline, PBS, plus 1% FCS, and 0.01% sodium azide). Binding of the antibodies to stimulated or non-stimulated cells was detected by a fluorescein (FITC) or phycoerthrin (PE) conjugated goat anti-human IgG (Jackson Immunoresearch, West Grove, Pa.). To confirm expression of CD137, a fusion protein consisting of the extracellular domain of CD137 ligand and mouse CD8 was used (Ancell Corporation, Bayport, Minn.), followed by incubation with PE-conjugated anti-mouse CD8 (BD Pharmingen, San Diego, Calif.). Samples were fixed in 1% formalin, kept at 4° C., and read by flow cytometry.

Functional assays: Primary human T-cells or monkey PBMC obtained from healthy donors were stimulated with immobilized anti-CD3 antibody to provide the first signal for T-cell activation, and co-stimulated with human anti-human CD137 antibodies. As a non-specific control, a humanized anti-carcinoma antibody (BR96) was used at the same antibody concentration. Plates were coated with anti-CD3 antibody (0.5-1 µg/ml) at 4° C. overnight. The next day T-cells or PBMC were plated at 1-1.5×10$^5$/well concentrations. Synthesis of IFN-γ was measured after 72 hours of culture at 37° C. either by cytometric bead array (CBA) or by ELISA.

Cytokine Assays

ELISA: After stimulation of T-cells at various times, plates were centrifuged and media was removed. Cytokine levels were detected by an ELISA in accordance with the manufacturer's instructions (BD Pharmingen, San Diego, Calif.). In brief, test samples and standards were added to anti-cytokine-coated 96-well plates. After incubation for 2 hr at ambient temperature, plates were washed 3 times in PBS-T and then incubated first with a working detector antibody, followed by the addition of substrate. Absorbance was read at 405 nm, and concentrations were calculated based on the standard curve.

Cytometric Bead Array: Another method used to determine cytokine production in vitro was flow cytometry using the Cytometric Bead array (CBA) developed by BD Pharmingen. Levels of IFN-γ, IL-2, IL-5, IL-4, IL-10, and TNF-α were measured in culture supernatants following manufacturers' instructions. Results were analyzed by flow cytometry with the CBA analysis software.

Results

Figure 8A:
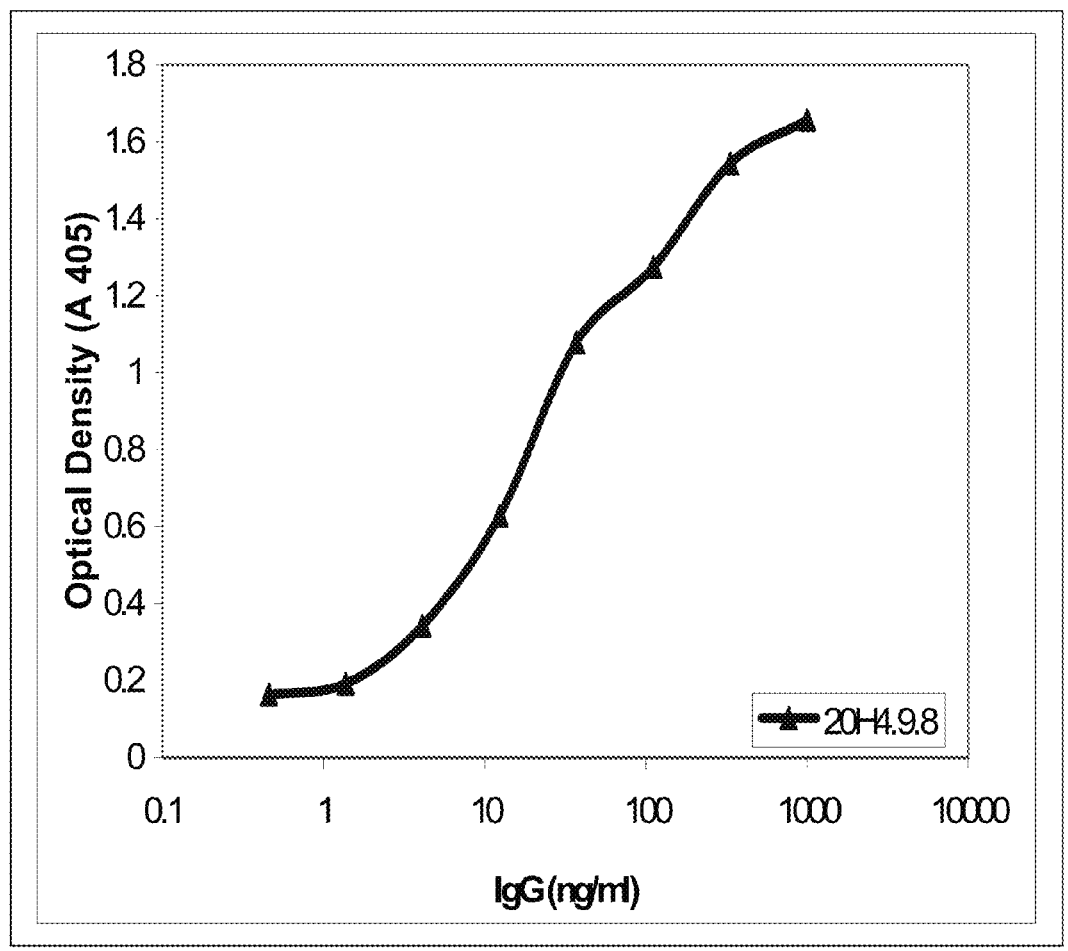
FIG. 8 (FIGS. 8A-8B) illustrates the results obtained from the binding of mab 20H4.9-IgG1 to human CD137 by ELISA (FIG. 8A) and the effect of mab 20H4.9-IgG1 on CD137-CD137L interaction (FIG. 8B).
Figure 8B:
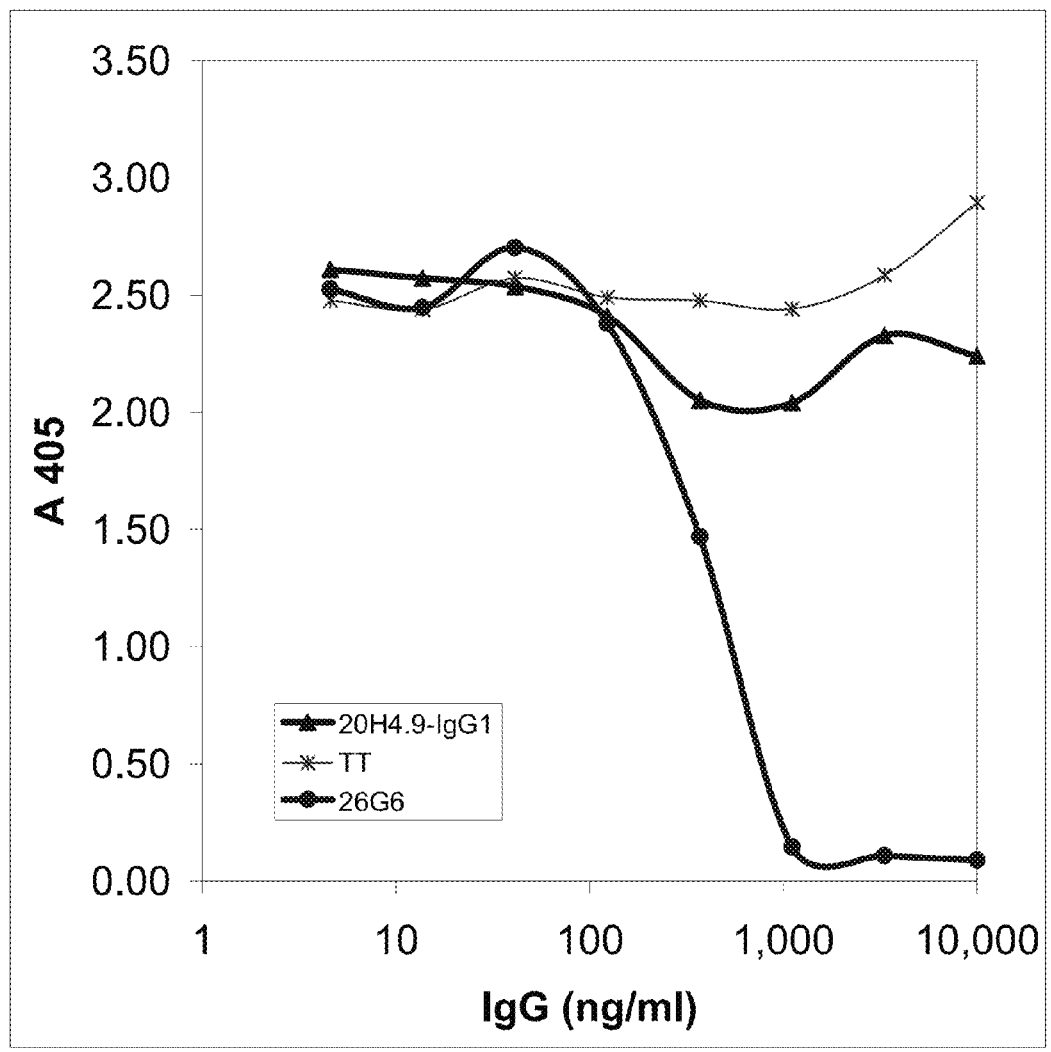

Hybridomas secreting antibodies that showed binding to human CD137 were further expanded, and subcloned. Secreted antibodies were purified and tested for their ability to bind to huCD137 and to allow the interaction of CD137-CD137L. Of the panel of anti-human CD137 antibodies evaluated, mab 20H4.9-IgG1 was selected for further evaluation based on its binding profile and non-blocking properties. The 20H4.9-IgG1 antibody is IgG1 kappa as determined by ELISA using alkaline phosphatase anti-human IgG1, 2, 3, 4, and anti-kappa and lambda reagents (Southern Biotech, Birmingham, Ala.). FIG. 8 (FIG. 8A—binding to human CD137 by ELISA; FIG. 8B—effect of mab 20H4.9-IgG1 on CD137-CD137L interaction) provides the initial characterization of mab 20H4.9-IgG1. Serial dilutions of mab 20H4.9-IgG1, 26G6 (a blocking anti-CD137 antibody), or tetanus toxoid (TT, negative control) were evaluated for their ability to alter binding of CD137 to CD137L. Mab 20H4.9-IgG1 at concentrations up to 10 µg/ml did not block CD137L binding, whereas mab 26G6 inhibited binding at concentrations >0.37 µg/ml.

Figure 9A:
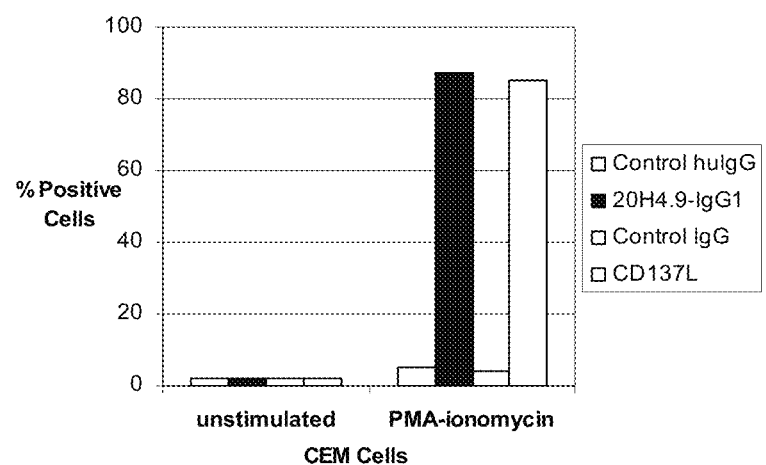
FIG. 9 (FIGS. 9A-9B) illustrates the results obtained from the binding of mab 20H4.9-IgG1 to PMA-ionomycin stimulated human or cynomolgus monkey cells. Human CEM (FIG. 9A) or monkey PBMC (FIG. 9B) were incubated with 20H4.9-IgG1 or human CD137L fusion protein.
Figure 9B:
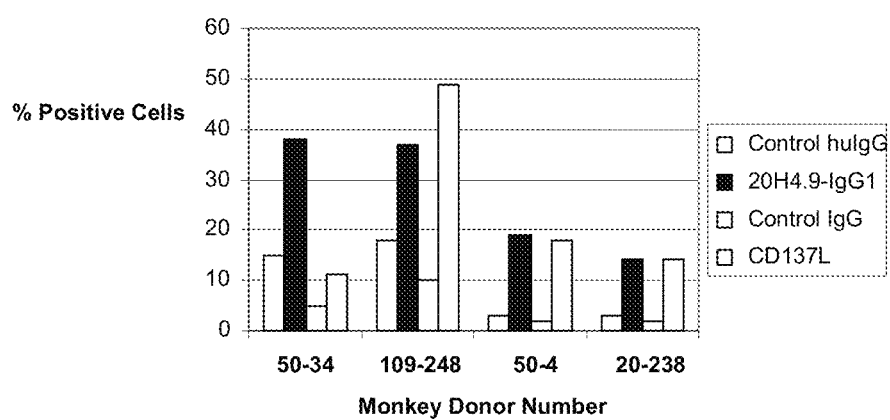

Mab 20H4.9-IgG1 was also tested for reactivity towards CD137 expressed on human T-cells (CEM) and in cynomolgus monkey peripheral blood monocytic cells (PBMC) stimulated with PMA and ionomycin. Previous studies determined that CD137 is upregulated on T-cells following activation with PMA and ionomycin. Control molecules consisted of an irrelevant human IgG antibody (negative control) or CD137L-CD8 fusion protein (positive control, BD Pharmingen, San Diego, Calif.). Results from these studies indicated that mab 20H4.9-IgG1 bound to activated human CEM and PBMCs from cynomolgus monkeys, with minimum binding to unstimulated cells. Similar percentages of positive cells were detected with either mab 20H4.9-IgG1 or CD137L. FIG. 9 provides the results obtained demonstrating the binding of mab 20H4.9-IgG1 to PMA-ionomycin stimulated human or cynomolgus monkey cells. Human CEM (FIG. 9A) or monkey PBMC (FIG. 9B) were incubated with 20H4.9-IgG1 or human CD137L fusion protein. Secondary antibodies were added and samples were read by flow cytometry.

Figures 10A, 10B:
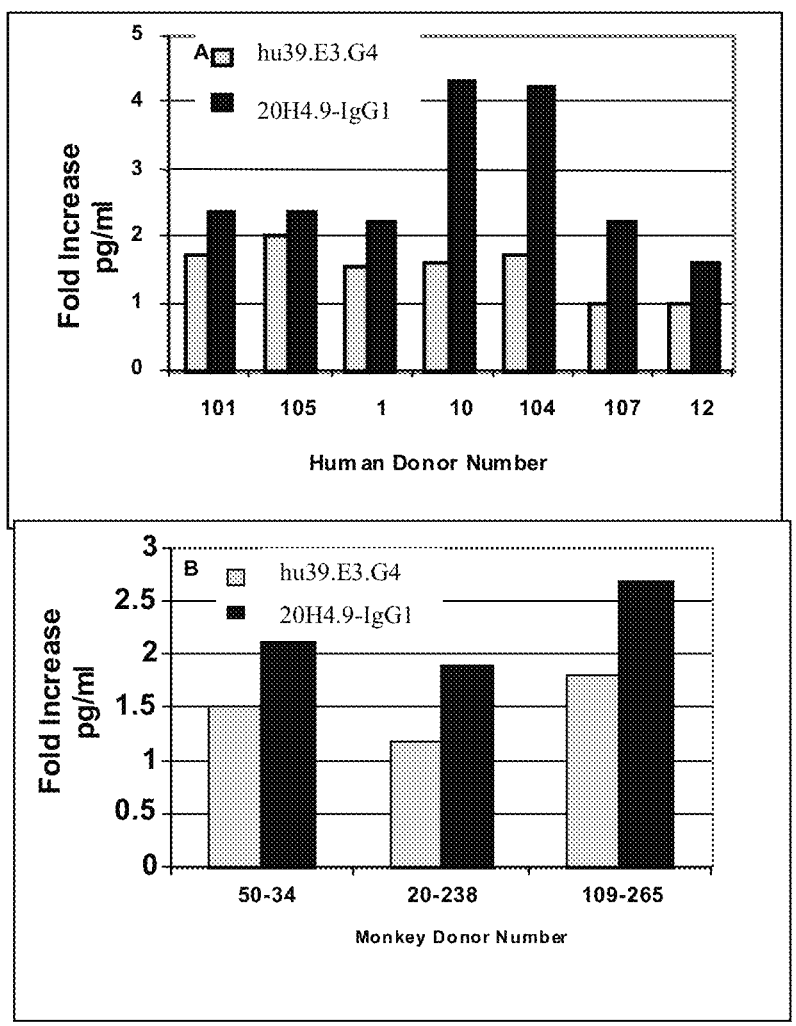
FIG. 10 (FIGS. 10A-10B) illustrates the results obtained by induction of IFN-γ in co-stimulatory studies with anti-CD137 antibodies, which are expressed as fold increase in pg/ml over controls. Due to the variable background response among donors, data was normalized relative to control treatments (=1). Median IFN-γ baseline level for human T-cells (FIG. 10A) or monkey PBMC (FIG. 10B) stimulated with anti-CD3 alone was 592 pg/ml and 505 pg/ml respectively.

Next, it was determined whether mab 20H4.9-IgG1 could induce enhancement of IFN-γ in costimulatory assays in the presence of anti-CD3 stimulation, the key functional effect desired for an agonistic CD137 antibody. Mab 20H4.9-IgG1 was evaluated for its co-stimulatory activity in functional studies in human and monkey lymphocytes. Based on initial data, a concentration of 20 ug/ml anti-CD137 antibody (excess antibody) was used in these studies. Levels of anti-CD3 antibody between 0.2-1 µg/ml were tested which resulted in 10-20% CD137-positive lymphocytes. Levels of IFN-γ in supernatants were measured after 72 h of culture. As shown in FIG. 10, mab 20H4.9-IgG1 enhanced IFN-γ synthesis in both human and monkey costimulatory assays to levels significantly higher than controls. Results of studies conducted with T-cells isolated from 8 healthy human donors showed that in six of them, mab 20H4.9-IgG1 enhanced IFN-γ synthesis between 2.2-4.3-fold compared to controls. One of the other two donors showed a 1.6-fold increase. The level of enhancement was superior to that observed with hu39E3.G4, a humanized anti-CD137 antibody provided in published PCT Application WO04/010947 (herein incorporated by reference) which showed augmentation of IFN-γ in 5 out of 8 donors and at levels lower than mab 20H4.9-IgG1 (1.5-2-fold increase) (FIG. 10A). In monkey costimulatory studies, mab 20H4.9-IgG1 also demonstrated enhanced functional activity resulting in significant augmentation of IFN-γ over controls (FIG. 10B). As in the human studies, enhancement of IFN-γ was consistently higher than with hu39E3.G4.

Induction of TNF-α synthesis above control levels was also observed in human cultures, albeit at much lower levels than IFN-γ. TNF-α levels induced by anti-CD3 antibody alone (baseline) were about 20-50 fold lower than baseline levels for IFN-γ. Mab 20H4.9-IgG1 induced an increase of ~2 to 4.7-fold in 3 out of 8 donors. Again, hu39E3.G4 (tested in parallel) induced ~2-fold increase in the same donors but at lower levels. Other cytokines tested, IL-2, IL-5, IL-10, and IL-4 did not change significantly with either treatment.

Together these studies demonstrated that mab 20H4.9-IgG1 presented the functional activity desired in both humans and monkeys by inducing a Th1-type of response. Significantly, since in vivo anti-tumor activity is associated with the ability of anti-CD137 antibodies to induce IFN-γ synthesis, these results supported the selection of mab 20H4.9-IgG1 for isotype switching.

Example 2

In Vitro Characterization of mab 20H4.9-IgG4

Based on its binding kinetics, inability to block CD137-CD137L interaction, and functional effects on human T-cells, mab 20H4.9-IgG1 was selected for switching to an IgG4 form. The IgG4 form of mab 20H4.9-IgG1 is 20H4.9-IgG4 (depicted in FIGS. 3 and 4).

The second phase of these studies involved the comparison of the in vitro properties of mab 20H4.9-IgG4 and mab 20H4.9-IgG1. In this section, the binding kinetic properties, and functional effects of both antibodies in human and monkey lymphocytes are described.

Binding Kinetics

Figure 11:
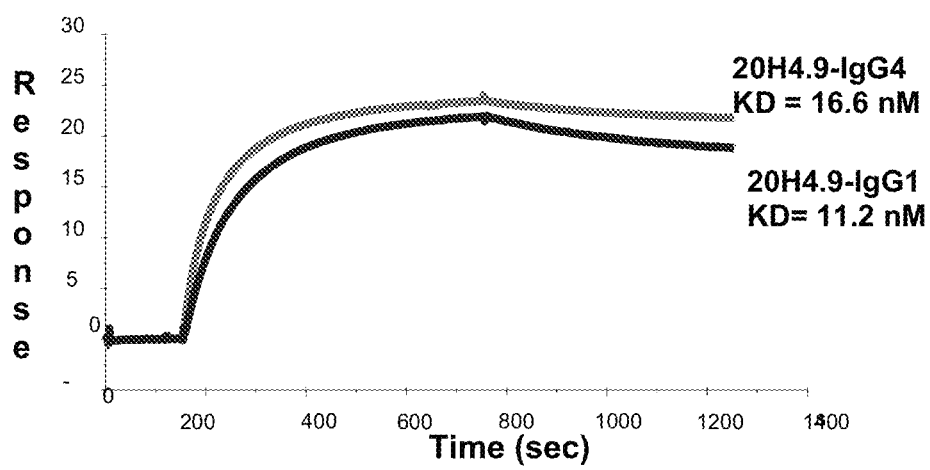
FIG. 11 provides plasmon resonance plots of binding of mab 20H4.9-IgG4 and mab 20H4.9-IgG1 to human CD137.
Figure 13A:
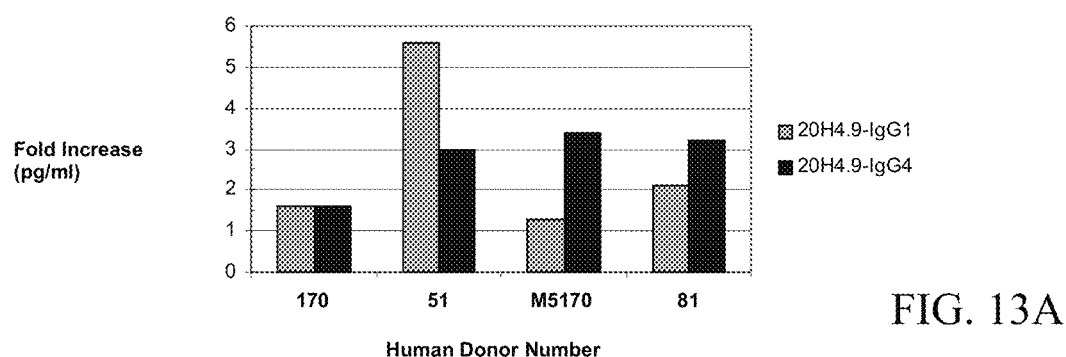
FIG. 13 (FIGS. 13A-B) illustrates the induction of IFN-γ in co-stimulatory studies with anti-CD137 antibodies. The results are expressed as fold increase in pg/ml over controls. Due to the variable background response among donors, data was normalized relative to control treatments (=1). Median IFN-γ baseline level for human T-cells (FIG. 13A) or monkey PBMC (FIG. 13B) stimulated with anti-CD3 alone was 592 pg/ml and 505 pg/ml respectively.
Figure 13B:
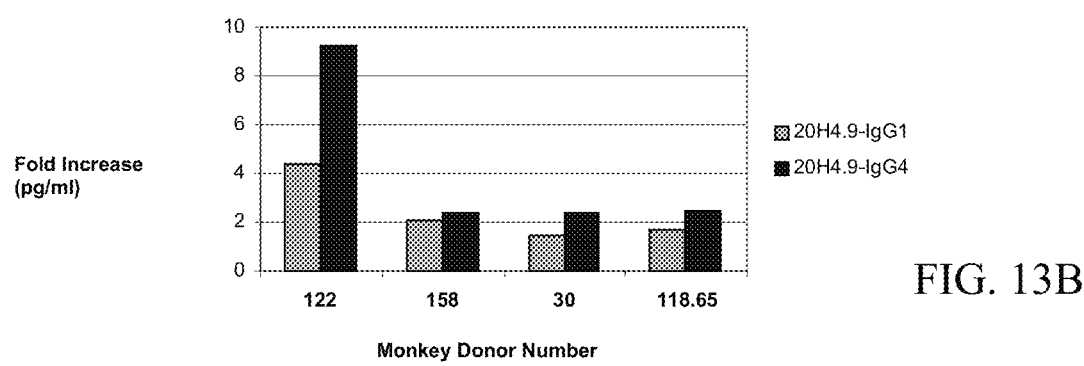

Kinetic properties of anti-human CD137 antibodies were evaluated by surface plasmon resonance using a BIAcore 3000 instrument. The antigen, human CD137-murine $IgG_{2a}$, was immobilized covalently at a low density on the surface of a CM5 sensorchip. Mab 20H4.9-IgG4 and mab 20H4.9-IgG1 were injected at concentrations between 25 and 200 nM. FIG. 11 depicts injections at 100 nM for both mab 20H4.9-IgG1 and mab 20H4.9-IgG4. Data calculated using BIAevaluation software (bivalent model, global curve fit analysis) resulted in kinetic parameters that were similar for both antibodies (see Table 1). Dissociation constants $K_D$ for mab 20H4.9-IgG1 and mab 20H4.9-IgG4 were determined as 11.2 and 16.6 nM, respectively. Under similar experimental conditions, mab 20H4.9-IgG4 did not bind to murine 4-1BB.

studies were conducted to compare the activity of mab 20H4.9-IgG4 to the parent mab 20H4.9-IgG1 in monkey PBMC and human T-cells. The functional effects of mab 20H4.9-IgG4 on human and monkey T-cells or PBMC were determined and compared to its parental molecule, mab 20H4.9-IgG1. Primary human T-cells or monkey PBMC obtained from healthy donors were stimulated with anti-CD3 antibody (0.5 µg/ml-1 µg/ml)+/−anti-human CD137 antibodies. Synthesis of IFN-γ was measured after 72 h of culture at 37° C. by cytometric bead array (CBA) for human samples or by ELISA for monkey samples. Antibodies were tested in costimulatory assays in the presence of suboptimal concentrations of anti-CD3 antibody (1 µg/ml) or Concavalin A (1 µg/ml) (donors M5170 and 81 only). Results are expressed as fold increase in pg/ml over controls. Due to the variable background response among donors, data was normalized relative to control treatments (=1). FIG. 13A provides the human T-cell results and FIG. 13B provides the monkey PBMC results. As shown in FIGS. 13A-13B, mab 20H4.9-IgG4 demonstrated costimulatory properties yielding higher levels of IFN-γ in human and monkey cells compared to controls. The level of enhancement of IFN-γ synthesis was comparable to its parental molecule in human and monkey samples.

Figure 14A:
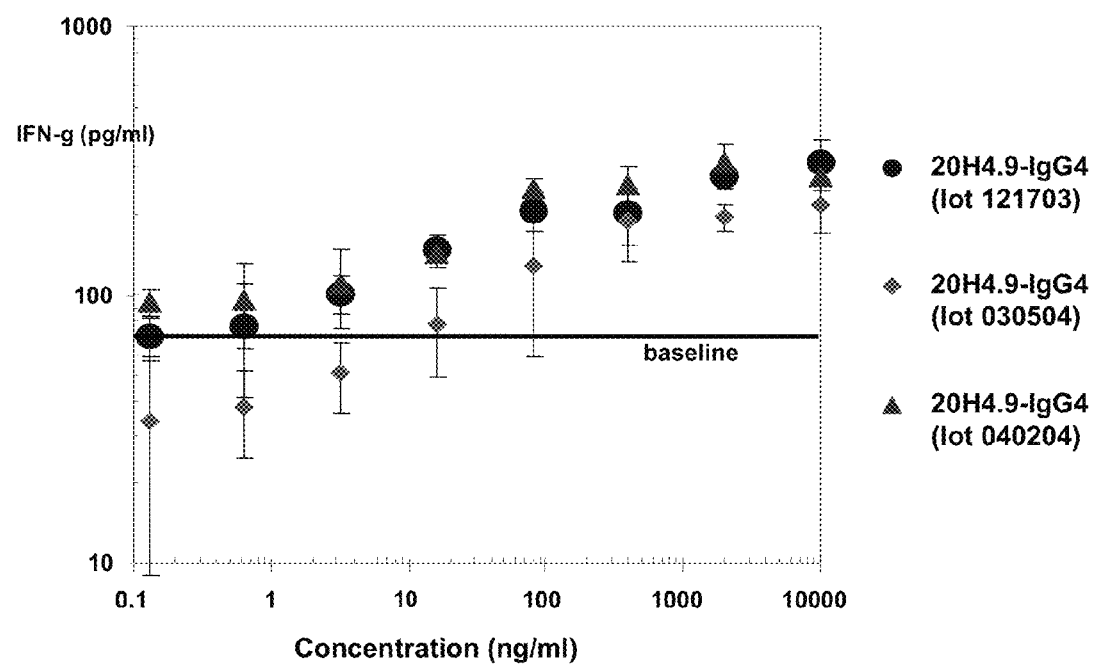
FIG. 14 (FIGS. 14A-14B) illustrates the results obtained of dose-dependent enhancement of IFN-γ synthesis by mab 20H4.9-IgG4 (FIG. 14A), and effect of antibody crosslinking by addition of crosslinking anti-human IgG antibody (7 µg/ml) (FIG. 14B).
Figure 14B:
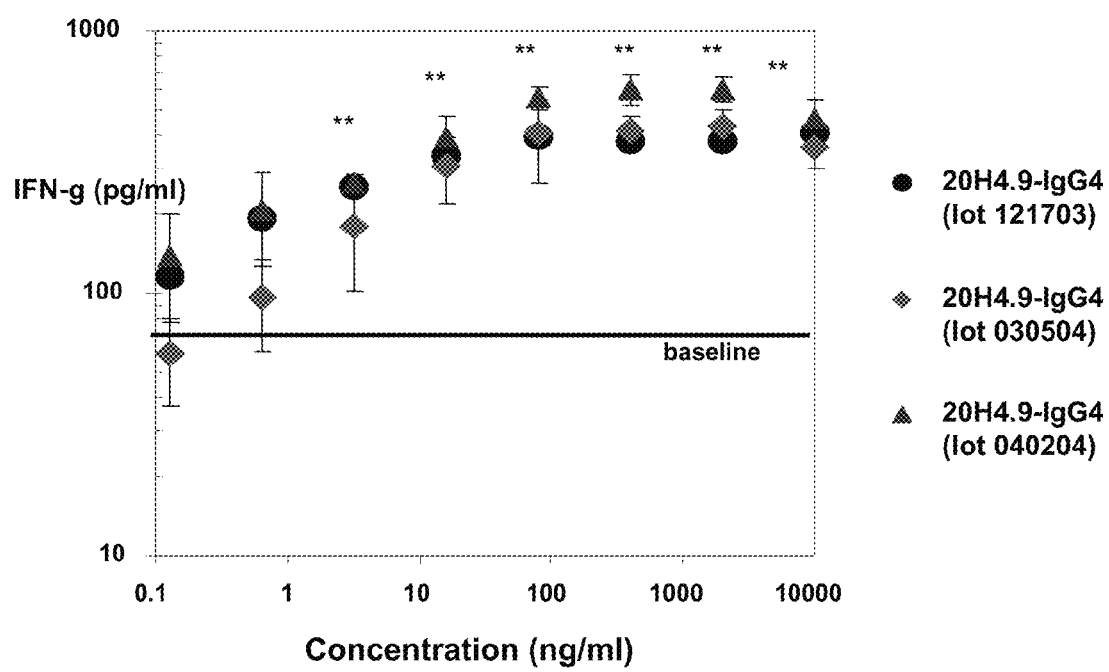

Subsequently, the effect of antibody cross-linking on the functional effect of mab 20H4.9-IgG4 was evaluated. It has been shown that cross-linking of antibodies may result in potentiation of their signaling ability. Thus, a study was conducted to determine the functional activity of several batches of mab 20H4.9-IgG4±an anti-human IgG antibody. As shown in FIG. 14A, significant enhancement of IFN-γ synthesis was observed for all lots tested in the absence of cross-linking antibodies, with a plateau at concentrations of 400 ng/ml. The augmentation of IFNγ synthesis by mab 20H4.9-IgG4 was further enhanced by the addition of anti-human IgG cross-linking antibody as shown in FIG. 14B. Different batches of mab 20H4.9-IgG4 had comparable cellular activities.

Thus, cross-linking of mab 20H4.9-IgG4 resulted in an enhancement of the ability of the antibody to induce IFN-γ

TABLE 1

Comparison of the binding kinetics of mab 20H4.9-IgG4 and mab 20H4.9-IgG1

| antibody | $k_{a1}$ (1/Ms) | $k_{d1}$ (1/s) | $k_{a2}$ (1/RUs) | kd2 (1/s) | Rmax (RU) | $K_A1$ | $K_D1$ (nM) |
|---|---|---|---|---|---|---|---|
| 20H4.9-IgG1 | 3.43E+04 | 3.85E−04 | 2.30E−05 | 1.51E−03 | 262 | 8.91E+07 | 11.22 |
| 20H4.9-IgG4 | 3.92E+04 | 6.51E−04 | 0.0755 | 0.105 | 409 | 6.02E+07 | 16.61 |

Flow Cytometric Analyses

Figure 12:
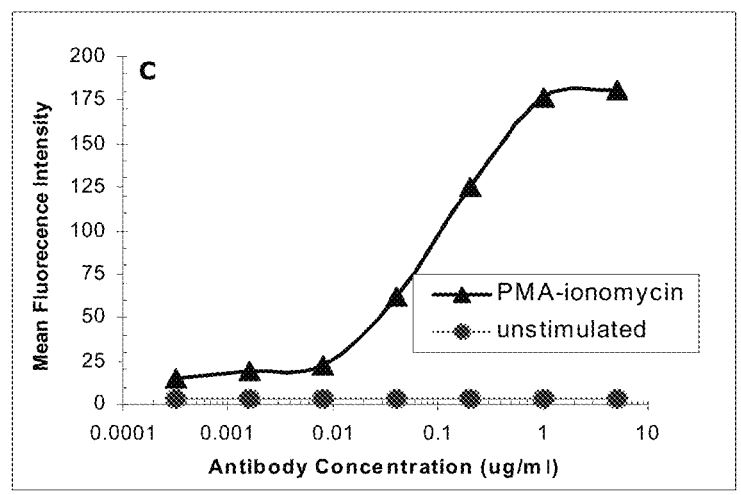
FIG. 12 illustrates the concentration-dependent binding of 20H4.9-IgG4 to PMA ionomycin stimulated human CEM cells, but no binding to unstimulated CEM cells.

Biotinylated mab 20H4.9-IgG4 at concentrations ranging from 0.32 ng/ml to 5 µg/ml was tested for binding to CEM cells±PMA-ionomycin. Mab 20H4.9-IgG4 bound to PMA-ionomycin stimulated CEM cells in a concentration-dependent manner. Saturation was achieved at 0.2 µg/ml. On the other hand, as shown for its parental molecule, mab 20H4.9-IgG1, mab 20H4.9-IgG4 did not bind to CEM cells that were not stimulated with PMA-ionomycin (FIG. 12). Concentration-dependent binding of mab 20H4-.9-IgG4 was demonstrated in PMA-ionomycin stimulated CEM cells (FIG. 12). Samples were read by flow cytometry.

Cellular/Functional Assays

To confirm that the process of switching the isotype of mab 20H4.9-IgG1 did not alter the activity of the antibody, in vitro synthesis. Antibody cross-linking in vivo may occur by cellular receptors for the Fc portion of immunoglobulins or by antibody dimerization. Mab 20H4.9-IgG4 is of the IgG4 isotype, which, compared to other IgG isotypes, has low affinity for Fc receptors. However, IgG4 can bind to FcγRI (CD64) expressed on monocytes and neutrophils.

Figure 15:
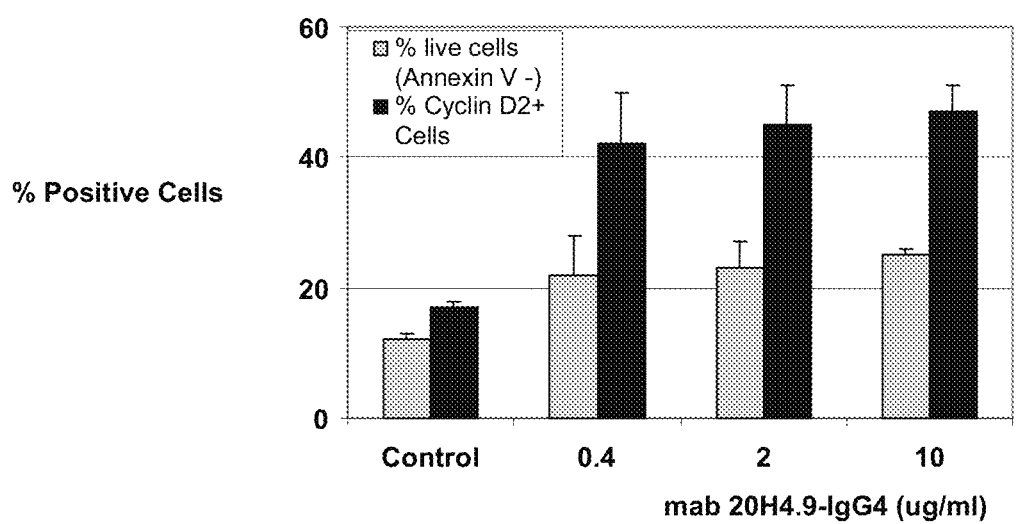
FIG. 15 illustrates the effect of mab 20H4.9-IgG4 on T-cell survival and cell cycle progression. Human T-cells were costimulated with anti-CD3 (1 ug/ml)±mab 20H4.9-IgG4 at the concentrations listed. Six days after initiation of the assays, cells were collected and stained with Annexin-V and propidium iodide to determine the number of live cells (Annexin V/PI negative), or PE-conjugated cyclin D2 to detect cycling cells. Results represent the mean(±SD) of 4 lots of mab 20H4.9-IgG4 tested in parallel.

Two other approaches were used to further characterize mab 20H4.9-IgG4: (i) effect on T-cell survival and (ii) effect on cyclin D2 expression. To determine whether mab 20H4.9-IgG4 could elicit signaling through CD137 on human T-cells and provide co-stimulatory signals to T-cells leading to cell survival and expansion, human T-cells stimulated with anti-CD3 antibodies+/−mab 20H4.9-IgG4 at concentrations known to induce IFN-γ synthesis were stained with annexin-V and propidium iodide to determine the number of live cells (Annexin V/Propidium iodide negative), and with Cyclin D2 to determine its effect on cell progression. FIG. 15 shows the average results of 4 different lots of mab 20H4.9-IgG4 on cyclin D2 expression and survival of T-cells. Concentrations of mab 20H4.9-IgG4 of 0.4-10 µg/ml resulted in an increase in the number of live cells by approximately 1.8-2 fold, and yielded a significant increase in the number of cyclin D2-expressing T-cells (2.5-3 fold).

Example 3

In Vivo Evaluation of 4-1BB Antibodies in a Pharmacodynamic Model in Cynomolgus Monkeys This example illustrates the ability of mab 20H4.9-IgG4 and mab hu39E3.G4 to enhance the antigen specific immune response elicited by DNA vaccines.

Materials and Methods

Experimental animal groups: Female and male cynomolgus monkeys (2.5 to 5.0 kg) were purchased from Charles River BRF (Houston, Tex.) for this study and were housed in pairs. Each experimental group consisted of 4 males and 2 females which were randomized into groups by body weight. Experimental groups were as follows:

Group 1—SW gag and PSA DNA vaccine (2 mg each), day 0, 28, 56, i.m., plus saline control, i.v., on days 12, 15 and 19;

Group 2—SW gag and PSA DNA vaccine (2 mg each), day 0, 28, 56, i.m., plus mab hu39E3.G4, i.v., on days 12, 15 and 19;

Group 3—SW gag and PSA DNA vaccine (2 mg each), day 0, 28, 56, i.m., plus mab 20H4.9-IgG4, i.v., on days 12, 15 and 19;

Group 4—untreated control group.

Immunizations and antibody treatments: PSA and SIV gag DNA vaccines were obtained from David B. Weiner, Department of Pathology and Laboratory of Medicine, University of Pennsylvania. (See, Kim et al., Oncogene 20, 4497-4506 (2001); Muthumani et al., Vaccine 21, 629-637 (2003).)

Monkeys were immunized by the intramuscular route with both PSA and SIV gag DNA constructs (2 mg/construct/immunization) simultaneously, followed by two boosts 4 weeks apart (days 0, 28, and 56). Twelve days after the initial immunization, treatment with mab 20H4.9-IgG4 or mab hu39E3.G4 was initiated. Antibodies were administered i.v, at 50 mg/kg, on days 12, 15, and 19 after the first immunization. This schedule was chosen because it was shown to suppress the antibody response to mab hu39E3.G4.

Clinical and Clinical Pathology

Throughout the course of the study, physical examinations were conducted on all monkeys by the attending veterinarians. Blood samples for hematology and serum chemistry analyses were collected prior to vaccinations and then 12, 42, 70, 97, 134, and 168 days after immunizations.

Immunological Assays

To determine the effect on the immune responses induced by these therapeutic regimens, an enzyme-linked immune spot assay (ELISPOT) was used for the detection of IFN-γ production by antigen-specific stimulated lymphocytes. Blood samples for ELISPOT analyses were collected prior to vaccinations and then 12, 42, 70, 97, 134, and 168 days after immunizations. Synthetic peptides corresponding to the complete sequences of SIV gag and the PSA antigen were used for ex-vivo stimulation of PBMC.

Results

Figure 16A:
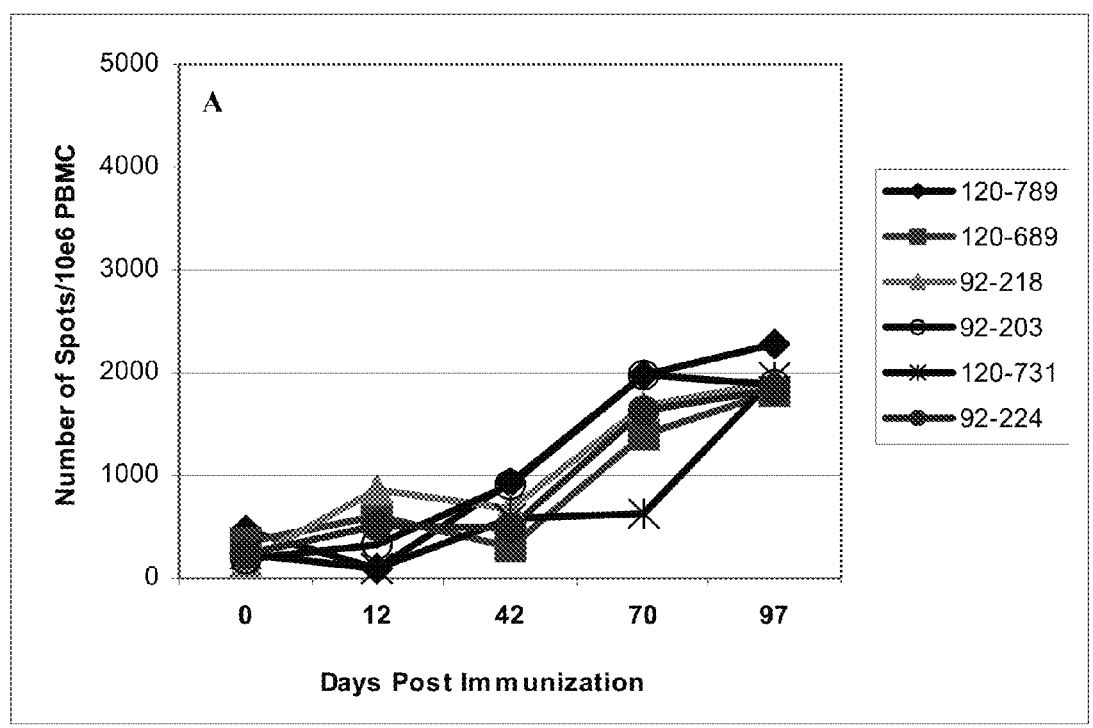
FIG. 16A), SIV gag vaccine (day 0, 28, 56) and mab 20H4.9-IgG4 (day 12, 15 and 19.
Figure 16B:
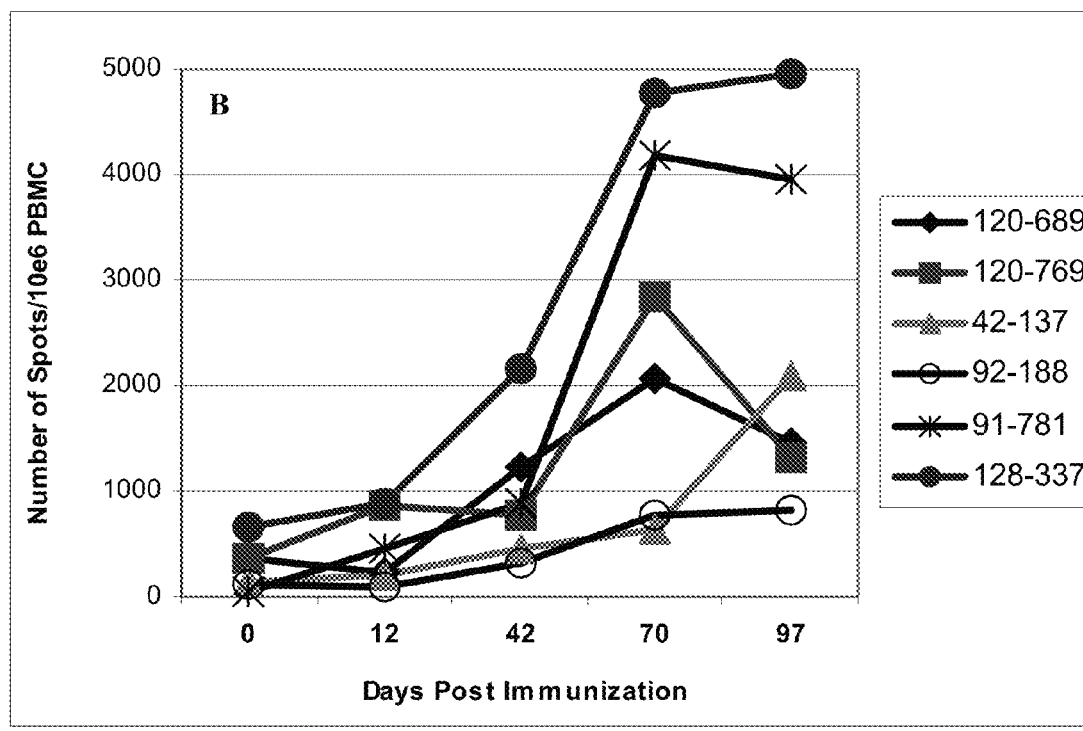
FIG. 16B), or SIV gag vaccine (day 0, 28, 56) and hu39E3.G4 (day 12, 15 and 19.
Figure 16C:
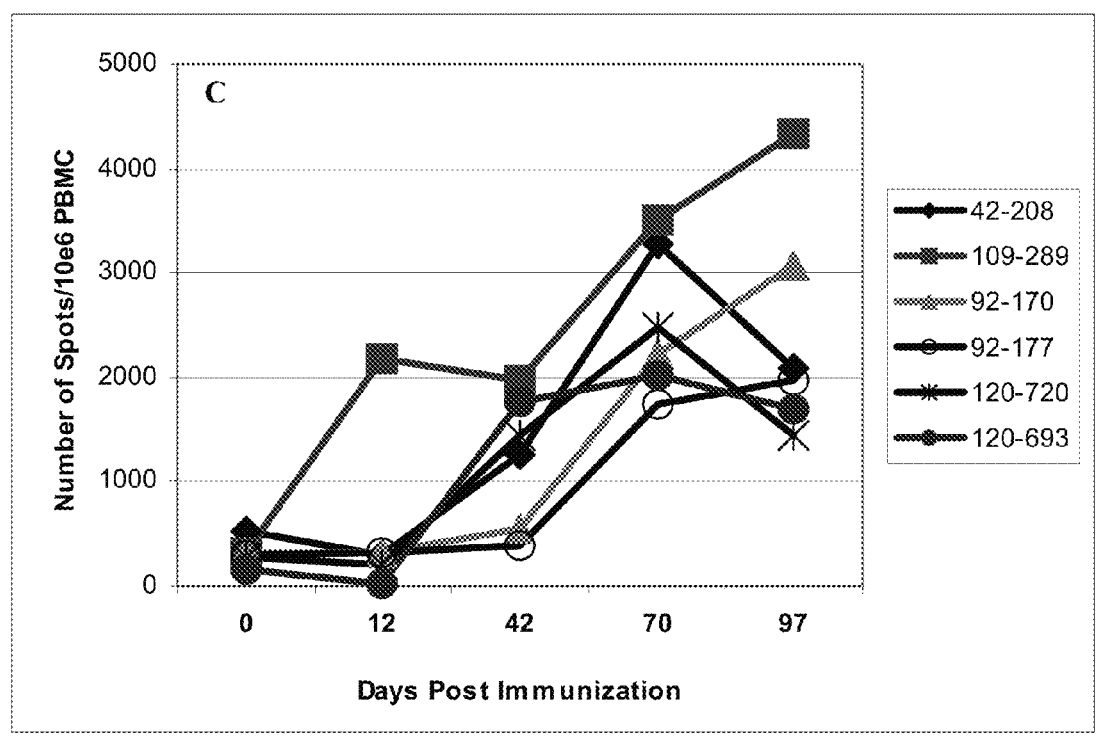
FIG. 16C). A group of animals was left untreated (FIG. 16D). At various times following treatment, blood was collected, and PBMC were separated and evaluated for their ability to secrete IFN-γ in the presence of antigen stimulation.
Figure 16D:
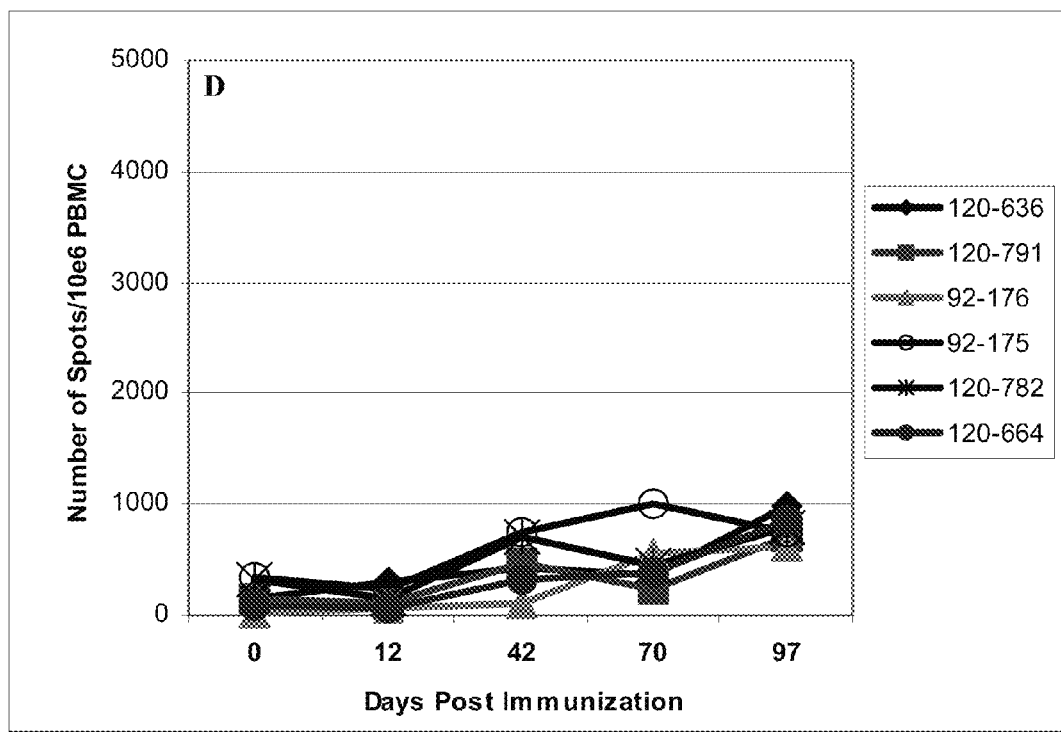
FIG. 16 (FIGS. 16A-16D) shows in cynomolgus monkeys the antigen-specific IFN-γ response as measured by ELISPOT after treatment with a DNA vaccine±anti-human 4-1BB antibodies. Animals were treated with a SIV gag vaccine (day 0, 28, 56.

Antigen-specific IFN-γ secreting cells in response to PSA or SIV gag peptides were quantitated by ELISPOT. FIG. 16 (FIGS. 16A-16D) illustrates the results obtained from Groups 1-4, respectively. The level of response to PSA was very low in all groups, indicating that the vaccine by itself did not induce a measurable and consistent immune response when compared to non-vaccinated animals. On the other hand, SIV gag vaccination alone resulted in significant number of antigen-specific IFN-γ secreting cells that augmented over time (FIG. 16A). Untreated animals (not vaccinated) showed 100-1,000 spots/$10^6$ PBMC throughout the course of the study (FIG. 16D). These results established the threshold response to the vaccine; animals that presented <1,000 spots/$10^6$ PBMC were considered non-responders. In the group of animals that received vaccine, 5 out of 6 monkeys showed an increased response overtime, with a mean number of spots after the third immunization (day 70) of 1,727 spots/$10^6$ PBMC (SD=242, range=1,403-1,968 spots/$10^6$ PBMC). One monkey was considered a non-responder (620 spots/million PBMC). Since in these studies MHC typing was not done, it is likely that the lack of T cell responses to the vaccine by some monkeys may be due to MHC-mismatch. Remarkably, on day 70, 4 out of 6 animals treated with SIV gag plus mab 20H4.9-IgG4 presented a significant higher number of IFN-γ spots (FIG. 16C) compared to control animals (FIG. 16D) and to macaques that were immunized with DNA vaccine alone (FIG. 16A). The mean number of spots after the third immunization for the mab 20H4.9-IgG4-treated group was of 3,465 spots/$10^6$ PBMC (SD=1,236, range=2,070-4,780 spots/$10^6$ PBMC). Two monkeys in that group did not respond to the vaccine (<800 spots/million PBMC). Following the third immunization (day 70), treatment with mab hu39E3.G4 plus DNA vaccine resulted in 6 out of 6 animals considered as responders with a mean number of spots/$10^6$ PBMC of 2,348 (SD=588, range=1,738-3,283) (FIG. 16B). For this group, the range of the number of spots was lower compared to those macaques treated with mab 20H4.9-IgG4.

Treatment with both mab 20H4.9-IgG4 and mab hu9E3.G4 was well tolerated and did not result in any significant changes in clinical signs, clinical chemistry, or hematological parameters relative to control monkeys.

These data show that mab 20H4.9-IgG4 treatment in combination with a DNA vaccine elicited an in vivo enhancement of the magnitude of the specific cellular response to the test antigen relative to controls or to treatment with mab hu39E3.G4, as measured by antigen specific IFN-γ-secreting cells. Since only one dose level of the antibodies and one dosing regimen were used in these preliminary studies, it is unlikely that maximal responses were induced, and further work to optimize conditions is required. Clearly, however, even with this non-optimized protocol, an enhancement of the cellular response to test antigens was achieved with mab 20H4.9-IgG4, suggesting that modulation of CD137 function may be an attractive approach for augmenting the effectiveness of DNA vaccines.

Although the invention has been described in some detail by way of illustration and example for purposes of clarity and understanding, it will be apparent that certain changes and modifications may be practiced within the scope of the appended claims.

The invention claimed is:

1. A monoclonal antibody or antigen-binding portion thereof that specifically binds to 4-1BB, comprising a light chain variable region and a heavy chain variable region, said light chain variable region comprises a CDR1 having amino acids 44-54 of SEQ ID NO:6, a CDR2 having amino acids 70-76 of SEQ ID NO:6, and a CDR3 having amino acids 109-119 of SEQ ID NO:6; and said heavy chain variable region comprises a CDR1 having amino acids 50-54 of SEQ ID NO:3, a CDR2 having amino acids 69-84 of SEQ ID NO:3, and a CDR3 having amino acids 117-129 of SEQ ID NO:3, and said monoclonal antibody is an IgG4 antibody.

2. The monoclonal antibody or antigen-binding portion thereof of claim 1, wherein: said light chain comprises a variable region having amino acids 21-129 of SEQ ID NO:6; and said heavy chain comprises a variable region having amino acids 20-140 of SEQ ID NO:3.

3. A monoclonal antibody comprising a light chain and a heavy chain, wherein said light chain comprises amino acid residues 21-236 of SEQ ID NO:6 and said heavy chain comprises amino acid residues 20-467 of SEQ ID NO:3, and said monoclonal antibody is an IgG4 antibody.

4. A pharmaceutical composition comprising: the monoclonal antibody or antigen-binding portion thereof of claim 1; and a pharmaceutically acceptable carrier.

5. A pharmaceutical composition comprising: the monoclonal antibody of claim 3; and a pharmaceutically acceptable carrier.

6. A method for treating a cancer in a subject comprising administering a therapeutically effective amount of the monoclonal antibody or antigen-binding portion thereof of claim 1 to said subject.

* * * * *

SEQUENCE LISTING

<160> NUMBER OF SEQ ID NOS: 9

<210> SEQ ID NO 1
<211> LENGTH: 7057
<212> TYPE: DNA
<213> ORGANISM: Artificial
<220> FEATURE:
<223> OTHER INFORMATION: pD17-20H4.9.h4a coding strand

<400> SEQUENCE: 1

```
cgatgtacgg gccagatata cgcgttgaca ttgattattg actagttatt aatagtaatc      60
aattacgggg tcattagttc atagcccata tatggagttc cgcgttacat aacttacggt     120
aaatggcccg cctggctgac cgcccaacga ccccccgccca ttgacgtcaa taatgacgta    180
tgttcccata gtaacgccaa tagggacttt ccattgacgt caatgggtgg actatttacg    240
gtaaactgcc cacttggcag tacatcaagt gtatcatatg ccaagtacgc cccctattga    300
cgtcaatgac ggtaaatggc ccgcctggca ttatgcccag tacatgacct tatgggactt    360
tcctacttgg cagtacatct acgtattagt catcgctatt accatggtga tgcggttttg    420
gcagtacatc aatgggcgtg atagcggtt tgactcacgg ggatttccaa gtctccaccc     480
cattgacgtc aatgggagtt tgttttggca ccaaaatcaa cgggactttc caaaatgtcg    540
taacaactcc gccccattga cgcaaatggg cggtaggcgt gtacggtggg aggtctatat    600
aagcagagct ctctggctaa ctagagaacc cactgcttac tggcttatcg aaattaatac    660
gactcactat agggagaccc aagcttggta ccgccatgaa acacctgtgg ttcttcctcc    720
tcctggtggc agctcccaga tgggtcctgt cccaggtgca actacagcag tggggcgcag    780
gactgttgaa gccttcggag accctgtccc tcacctgcgc tgtctatggt gggtccttca    840
gtggttacta ctggagctgg atacgccagt ccccagagaa ggggctggag tggattgggg    900
aaatcaatca tggtggatac gtcacctaca atccgtccct cgagagtcga gtcaccatat    960
cagtagacac gtccaagaac cagttctccc tgaagctgag ctctgtgacc gccgcggaca   1020
cggctgtata ttactgtgcg agggactatg tccggggaa ttatgactgg tacttcgatc   1080
tctggggccg tggcaccctg gtcactgtct cctcagctag caccaagggc ccatccgtct   1140
tccccctggc gccctgctcc aggagcacct ccgagagcac agccgccctg gctgcctgg   1200 tcaaggacta cttccccgaa ccggtgacgg tgtcgtggaa ctcaggcgcc ctgaccagcg   1260
gcgtgcacac cttcccggct gtcctacagt cctcaggact ctactccctc agcagcgtgg   1320
tgaccgtgcc ctccagcagc ttgggcacga agacctacac ctgcaacgta gatcacaagc   1380
ccagcaacac caaggtggac aagagagttg agtccaaata tggtcccacct tgcccacctt   1440 gcccagcacc tgagttcctg gggggaccat cagtcttcct gttccccca aaacccaagg   1500 acactctcat gatctcccgg acccctgagg tcacgtgcgt ggtggtggac gtgagccagg   1560
aagaccccga ggtccagttc aactggtacg tggatggcgt ggaggtgcat aatgccaaga   1620
caaagccgcg ggaggagcag ttcaacagca cgtaccgtgt ggtcagcgtc ctcaccgtcc   1680
tgcaccagga ctggctgaac ggcaaggagt acaagtgcaa ggtctccaac aaaggcctcc   1740
cgtcctccat cgagaaaacc atctccaaag ccaaagggca gccccgagag ccacaggtgt   1800
acaccctgcc cccatcccag gaggagatga ccaagaacca ggtcagcctg acctgcctgg   1860
tcaaaggctt ctaccccagc gacatcgccg tggagtggga gagcaatggg cagccggaga   1920
acaactacaa gaccacgcct cccgtgctgg actccgacgg ctccttcttc ctctacagca   1980
ggctaaccgt ggacaagagc aggtggcagg aggggaatgt cttctcatgc tccgtgatgc   2040
```

-continued

```
atgaggctct gcacaaccac tacacacaga agagcctctc cctgtctctg ggtaaatgat    2100
ctagagggcc ctattctata gtgtcaccta aatgctagag ctcgctgatc agcctcgact    2160
gtgccttcta gttgccagcc atctgttgtt tgccctccc ccgtgccttc cttgaccctg     2220
gaaggtgcca ctcccactgt cctttcctaa taaaatgagg aaattgcatc gcattgtctg    2280
agtaggtgtc attctattct ggggggtggg gtggggcagg acagcaaggg ggaggattgg    2340
gaagacaata gcaggcatgc tgggatgcg gtgggctcta tggcttctga gcggaaaga      2400
accagctggg gctctagggg gtatccccac gcgccctgta gcggcgcatt aagcgcggcg    2460
ggtgtggtgg ttacgcgcag cgtgaccgct acacttgcca gcgccctagc gcccgctcct    2520
ttcgctttct tcccttcctt tctcgccacg ttcgccgggc tctcaaaaa agggaaaaaa     2580
agcatgcatc tcaattagtc agcaaccata gtcccgcccc taactccgcc catcccgccc    2640
ctaactccgc ccagttccgc ccattctccg ccccatggct gactaatttt ttttatttat    2700
gcagaggccg aggccgcctc ggcctctgag ctattccaga agtagtgagg aggctttttt    2760
ggaggcctag gcttttgcaa aaagcttgga cagctcaggg ctgcgatttc gcgccaaact    2820
tgacggcaat cctagcgtga aggctggtag gatttatcc ccgctgccat catggttcga     2880
ccattgaact gcatcgtcgc cgtgtcccaa aatatgggga ttggcaagaa cggagaccta    2940
ccctggcctc cgctcaggaa cgagttcaag tacttccaaa gaatgaccac aacctcttca    3000
gtggaaggta aacagaatct ggtgattatg ggtaggaaaa cctggttctc cattcctgag    3060
aagaatcgac ctttaaagga cagaattaat atagttctca gtagagaact caaagaacca    3120
ccacgaggag ctcattttct tgccaaaagt ttggatgatg ccttaagact tattgaacaa    3180
ccggaattgg caagtaaagt agacatggtt tggatagtcg gaggcagttc tgtttaccag    3240
gaagccatga atcaaccagg ccaccttaga ctctttgtga caaggatcat gcaggaattt    3300
gaaagtgaca cgttttttccc agaaattgat ttggggaaat ataaacttct cccagaatac    3360
ccaggcgtcc tctctgaggt ccaggaggaa aaaggcatca agtataagtt tgaagtctac    3420
gagaagaaag actaacagga agatgctttc aagttctctg ctccccctcct aaagctatgc    3480
atttttataa gaccatggga cttttgctgg ctttagatct ctttgtgaag gaaccttact    3540
tctgtggtgt gacataattg gacaaactac ctacagagat ttaaagctct aaggtaaata    3600
taaaattttt aagtgtataa tgtgttaaac tactgattct aattgtttgt gtattttaga    3660
ttccaaccta tggaactgat gaatgggagc agtggtggaa tgcctttaat gaggaaaacc    3720
tgttttgctc agaagaaatg ccatctagtg atgatgaggc tactgctgac tctcaacatt    3780
ctactcctcc aaaaaagaag agaaaggtag aagaccccaa ggactttcct tcagaattgc    3840
taagtttttt gagtcatgct gtgtttagta atagaactct tgcttgcttt gctatttaca    3900
ccacaaagga aaaagctgca ctgctataca agaaaattat ggaaaaatat tctgtaaccct    3960
ttataagtag gcataacagt tataatcata acatactgtt ttttcttact ccacacaggc    4020
atagagtgtc tgctattaat aactatgctc aaaaattgtg taccctttagc ttttttaattt   4080
gtaaaggggt taataaggaa tatttgatgt atagtgcctt gactagagat cataatcagc    4140
cataccacat ttgtagaggt tttacttgct ttaaaaaacc tcccacacct cccccctgaac    4200
ctgaaacata aaatgaatgc aattgttgtt gttaacttgt ttattgcagc ttataatggt    4260
tacaaataaa gcaatagcat cacaaatttc acaaataaag catttttttc actgcattct    4320
agttgtggtt tgtccaaact catcaatgta tcttatcatg tctggatcgg ctggatgatc    4380
```

```
ctccagcgcg gggatctcat gctggagttc ttcgcccacc ccaacttgtt tattgcagct    4440
tataatggtt acaaataaag caatagcatc acaaatttca caaataaagc attttttca     4500 ctgcattcta gttgtggttt gtccaaactc atcaatgtat cttatcatgt ctgtataccg    4560
tcgacctcta gctagagctt ggcgtaatca tggtcatagc tgtttcctgt gtgaaattgt    4620
tatccgctca caattccaca acatacga gccggaagca taaagtgtaa agcctggggt      4680
gcctaatgag tgagctaact cacattaatt gcgttgcgct cactgcccgc tttccagtcg    4740
ggaaacctgt cgtgccagct gcattaatga atcggccaac gcgcgggag aggcggtttg      4800 cgtattgggc gctcttccgc ttcctcgctc actgactcgc tgcgctcggt cgttcggctg    4860
cggcgagcgg tatcagctca ctcaaaggcg gtaatacggt tatccacaga atcaggggat    4920
aacgcaggaa agaacatgtg agcaaaaggc cagcaaaagg ccaggaaccg taaaaaggcc    4980
gcgttgctgg cgtttttcca taggctccgc ccccctgacg agcatcacaa aaatcgacgc    5040
tcaagtcaga ggtggcgaaa cccgacagga ctataaagat accaggcgtt tccccctgga    5100
agctccctcg tgcgctctcc tgttccgacc ctgccgctta ccggatacct gtccgccttt    5160
ctcccttcgg gaagcgtggc gctttctcaa tgctcacgct gtaggtatct cagttcggtg    5220
taggtcgttc gctccaagct gggctgtgtg cacgaacccc ccgttcagcc cgaccgctgc    5280
gccttatccg gtaactatcg tcttgagtcc aacccggtaa gacacgactt atcgccactg    5340
gcagcagcca ctggtaacag gattagcaga gcgaggtatg taggcggtgc tacagagttc    5400
ttgaagtggt ggcctaacta cggctacact agaaggacag tatttggtat ctgcgctctg    5460
ctgaagccag ttaccttcgg aaaaagagtt ggtagctctt gatccggcaa acaaaccacc    5520
gctggtagcg gtggttttttt tgtttgcaag cagcagatta cgcgcagaaa aaaggatct    5580 caagaagatc ctttgatctt ttctacgggg tctgacgctc agtggaacga aaactcacgt    5640
taagggattt tggtcatgag attatcaaaa aggatcttca cctagatcct tttaaattaa    5700
aaatgaagtt ttaaatcaat ctaaagtata tatgagtaaa cttggtctga cagttaccaa    5760
tgcttaatca gtgaggcacc tatctcagcg atctgtctat ttcgttcatc catagttgcc    5820
tgactccccg tcgtgtagat aactacgata cgggagggct taccatctgg ccccagtgct    5880
gcaatgatac cgcgagaccc acgctcaccg gctccagatt tatcagcaat aaaccagcca    5940
gccgaagggg ccgagcgcag aagtggtcct gcaactttat ccgcctccat ccagtctatt    6000
aattgttgcc gggaagctag agtaagtagt tcgccagtta atagtttgcg caacgttgtt    6060
gccattgcta caggcatcgt ggtgtcacgc tcgtcgtttg gtatggcttc attcagctcc    6120
ggttcccaac gatcaaggcg agttacatga tcccccatgt tgtgcaaaaa agcggttagc    6180
tccttcggtc ctccgatcgt tgtcagaagt aagttggccg cagtgttatc actcatggtt    6240
atggcagcac tgcataattc tcttactgtc atgccatccg taagatgctt ttctgtgact    6300
ggtgagtact caaccaagtc attctgagaa tagtgtatgc ggcgaccgag ttgctcttgc    6360
ccggcgtcaa tacgggataa taccgcgcca catagcagaa ctttaaaagt gctcatcatt    6420
ggaaaacgtt cttcggggcg aaaactctca aggatcttac cgctgttgag atccagttcg    6480
atgtaaccca ctcgtgcacc caactgatct tcagcatctt ttactttcac cagcgtttct    6540
gggtgagcaa aaacaggaag gcaaaatgcc gcaaaaaagg gaataagggc gacacggaaa    6600
tgttgaatac tcatactctt cctttttcaa tattattgaa gcatttatca gggttattgt    6660
ctcatgagcg gatacatatt tgaatgtatt tagaaaaata aacaataggg gttccgcgc     6720 acatttcccc gaaaagtgcc acctgacgtc gacggatcgg gagatctgct aggtgacctg    6780
```

| | | | |
|---|---|---|---|
| aggcgcgccg | gcttcgaata | gccagagtaa | ccttttttt taattttatt ttattttatt | 6840 |
| tttgagatgg | agtttggcgc | cgatctcccg | atccccatg gtcgactctc agtacaatct | 6900 |
| gctctgatgc | cgcatagtta | agccagtatc | tgctccctgc ttgtgtgttg gaggtcgctg | 6960 |
| agtagtgcgc | gagcaaaatt | taagctacaa | caaggcaagg cttgaccgac aattgcatga | 7020 |
| agaatctgct | tagggttagg | cgttttgcgc | tgcttcg | 7057 |

<210> SEQ ID NO 2
<211> LENGTH: 7057
<212> TYPE: DNA
<213> ORGANISM: Artificial
<220> FEATURE:
<223> OTHER INFORMATION: pD17-20H4.9.h4a complementary strand

<400> SEQUENCE: 2

| | | | | |
|---|---|---|---|---|
| gctacatgcc | cggtctatat | gcgcaactgt | aactaataac tgatcaataa ttatcattag | 60 |
| ttaatgcccc | agtaatcaag | tatcgggtat | atacctcaag gcgcaatgta ttgaatgcca | 120 |
| tttaccgggc | ggaccgactg | gcgggttgct | ggggcgggt aactgcagtt attactgcat | 180 |
| acaagggtat | cattgcggtt | atccctgaaa | ggtaactgca gttacccacc tgataaatgc | 240 |
| catttgacgg | gtgaaccgtc | atgtagttca | catagtatac ggttcatgcg ggggataact | 300 |
| gcagttactg | ccatttaccg | gcggaccgt | aatacgggtc atgtactgga taccctgaa | 360 |
| aggatgaacc | gtcatgtaga | tgcataatca | gtagcgataa tggtaccact acgccaaaac | 420 |
| cgtcatgtag | ttacccgcac | ctatcgccaa | actgagtgcc cctaaaggtt cagaggtggg | 480 |
| gtaactgcag | ttaccctcaa | acaaaaccgt | ggttttagtt gccctgaaag gttttacagc | 540 |
| attgttgagg | cggggtaact | gcgtttaccc | gccatccgca catgccaccc tccagatata | 600 |
| ttcgtctcga | gagaccgatt | gatctcttgg | gtgacgaatg accgaatagc tttaattatg | 660 |
| ctgagtgata | tccctctggg | ttcgaaccat | ggcggtactt tgtggacacc aagaaggagg | 720 |
| aggaccaccg | tcgagggtct | acccaggaca | gggtccacgt tgatgtcgtc accccgcgtc | 780 |
| ctgacaactt | cggaagcctc | tgggacaggg | agtggacgcg acagatacca cccaggaagt | 840 |
| caccaatgat | gacctcgacc | tatgcggtca | ggggtctctt ccccgacctc acctaaccc | 900 |
| tttagttagt | accacctatg | cagtggatgt | taggcaggga gctctcagct cagtggtata | 960 |
| gtcatctgtg | caggttcttg | gtcaagaggg | acttcgactc gagacactgg cggcgcctgt | 1020 |
| gccgacatat | aatgacacgc | tccctgatac | caggcccctt aatactgacc atgaagctag | 1080 |
| agacccccggc | accgtgggac | cagtgacaga | ggagtcgatc gtggttcccg ggtaggcaga | 1140 |
| agggggaccg | cgggacgagg | tcctcgtgga | ggctctcgtg tcggcgggac ccgacggacc | 1200 |
| agttcctgat | gaaggggctt | ggccactgcc | acagcacctt gagtccgcgg gactggtcgc | 1260 |
| cgcacgtgtg | gaagggccga | caggatgtca | ggagtcctga gatgagggag tcgtcgcacc | 1320 |
| actggcacgg | gaggtcgtcg | aaccgtgct | tctggatgtg gacgttgcat ctagtgttcg | 1380 |
| ggtcgttgtg | gttccacctg | ttctctcaac | tcaggtttat accaggtgga acgggtggaa | 1440 |
| cgggtcgtgg | actcaaggac | cccctggta | gtcagaagga caagggggt tttgggttcc | 1500 |
| tgtgagagta | ctagagggcc | tggggactcc | agtgcacgca ccaccactg cactcggtcc | 1560 |
| ttctggggct | ccaggtcaag | ttgaccatgc | acctaccgca cctccacgta ttacggttct | 1620 |
| gtttcggcgc | cctcctcgtc | aagttgtcgt | gcatggcaca ccagtcgcag gagtggcagg | 1680 |
| acgtggtcct | gaccgacttg | ccgttcctca | tgttcacgtt ccagaggttg tttccggagg | 1740 |

```
gcaggaggta gctcttttgg tagaggtttc ggtttcccgt cggggctctc ggtgtccaca    1800
tgtgggacgg gggtagggtc ctcctctact ggttcttggt ccagtcggac tggacggacc    1860
agtttccgaa gatggggtcg ctgtagcggc acctcaccct ctcgttaccc gtcggcctct    1920
tgttgatgtt ctggtgcgga gggcacgacc tgaggctgcc gaggaagaag agatgtcgt    1980 ccgattggca cctgttctcg tccaccgtcc tccccttaca gaagagtacg aggcactacg    2040
tactccgaga cgtgttggtg atgtgtgtct tctcggagag ggacagagac ccatttacta    2100
gatctcccgg gataagatat cacagtggat ttacgatctc gagcgactag tcggagctga    2160
cacggaagat caacggtcgg tagacaacaa acggggaggg ggcacggaag gaactgggac    2220
cttccacggt gagggtgaca ggaaaggatt attttactcc tttaacgtag cgtaacagac    2280
tcatccacag taagataaga cccccaccc caccccgtcc tgtcgttccc cctcctaacc    2340
cttctgttat cgtccgtacg accccctacgc cacccgagat accgaagact ccgcctttct    2400
tggtcgaccc cgagatcccc catagggtg cgcgggacat cgccgcgtaa ttcgcgccgc    2460
ccacaccacc aatgcgcgtc gcactggcga tgtgaacggt cgcgggatcg cgggcgagga    2520
aagcgaaaga agggaaggaa agagcggtgc aagcggcccg gagagttttt tccctttttt    2580
tcgtacgtag agttaatcag tcgttggtat cagggcgggg attgaggcgg gtagggcggg    2640
gattgaggcg ggtcaaggcg ggtaagaggc ggggtaccga ctgattaaaa aaaataaata    2700
cgtctccggc tccggcggag ccggagactc gataaggtct tcatcactcc tccgaaaaaa    2760
cctccggatc cgaaaacgtt tttcgaacct gtcgagtccc gacgctaaag cgcggtttga    2820
actgccgtta ggatcgcact tccgaccatc ctaaaatagg ggcgacggta gtaccaagct    2880
ggtaacttga cgtagcagcg gcacaggggtt ttataccect aaccgttctt gcctctggat    2940
gggaccggag gcgagtcctt gctcaagttc atgaaggttt cttactggtg ttggagaagt    3000
caccttccat ttgtcttaga ccactaatac ccatccttt ggaccaagag gtaaggactc    3060
ttcttagctg gaaatttcct gtcttaatta tatcaagagt catctcttga gtttcttggt    3120
ggtgctcctc gagtaaaaga acggttttca aacctactac ggaattctga ataacttgtt    3180
ggccttaacc gttcatttca tctgtaccaa acctatcagc ctccgtcaag acaaatggtc    3240
cttcggtact tagttggtcc ggtggaatct gagaaacact gttcctagta cgtccttaaa    3300
ctttcactgt gcaaaagggg tcttttaacta aaccccttta tatttgaaga gggtcttatg    3360
ggtccgcagg agagactcca ggtcctcctt ttccgtagt tcatattcaa acttcagatg    3420
ctcttctttc tgattgtcct tctacgaaag ttcaagagac gagggagga tttcgatacg    3480 taaaaatatt ctggtaccct gaaaacgacc gaaatctaga gaaacacttc cttggaatga    3540
agacaccaca ctgtattaac ctgtttgatg gatgtctcta aatttcgaga ttccatttat    3600
atttttaaaa ttcacatatt acacaatttg atgactaaga ttaacaaaca cataaaatct    3660
aaggttggat accttgacta cttaccctcg tcaccacctt acggaaatta ctccttttgg    3720
acaaaacgag tcttctttac ggtagatcac tactactccg atgacgactg agagttgtaa    3780
gatgaggagg ttttttcttc tctttccatc ttctggggtt cctgaaagga agtcttaacg    3840
attcaaaaaa ctcagtacga cacaaatcat tatcttgaga acgaacgaaa cgataaatgt    3900
ggtgtttcct ttttcgacgt gacgatatgt tcttttaata ccttttttata agacattgga    3960 aatattcatc cgtattgtca atattagtat tgtatgacaa aaaagaatga ggtgtgtccg    4020
tatctcacag acgataatta ttgatacgag ttttaaacac atggaaatcg aaaaattaaa    4080
catttcccca attattcctt ataaactaca tatcacggaa ctgatctcta gtattagtcg    4140
```

```
gtatggtgta acatctcca aaatgaacga aattttttgg agggtgtgga gggggacttg    4200
gactttgtat tttacttacg ttaacaacaa caattgaaca aataacgtcg aatattacca    4260
atgtttattt cgttatcgta gtgtttaaag tgtttatttc gtaaaaaaag tgacgtaaga    4320
tcaacaccaa acaggtttga gtagttacat agaatagtac agacctagcc gacctactag    4380
gaggtcgcgc ccctagagta cgacctcaag aagcgggtgg ggttgaacaa ataacgtcga    4440
atattaccaa tgtttatttc gttatcgtag tgtttaaagt gtttatttcg taaaaaaagt    4500
gacgtaagat caacaccaaa caggtttgag tagttacata gaatagtaca gacatatggc    4560
agctggagat cgatctcgaa ccgcattagt accagtatcg acaaggaca cactttaaca    4620 ataggcgagt gttaaggtgt gttgtatgct cggccttcgt atttcacatt tcggacccca    4680
cggattactc actcgattga gtgtaattaa cgcaacgcga gtgacgggcg aaaggtcagc    4740
cctttggaca gcacggtcga cgtaattact tagccggttg cgcgcccctc tccgccaaac    4800
gcataacccg cgagaaggcg aaggagcgag tgactgagcg acgcgagcca gcaagccgac    4860
gccgctcgcc atagtcgagt gagtttccgc cattatgcca ataggtgtct tagtccccta    4920
ttgcgtcctt tcttgtacac tcgttttccg gtcgttttcc ggtccttggc attttccgg    4980 cgcaacgacc gcaaaaaggt atccgaggcg ggggactgc tcgtagtgtt tttagctgcg    5040
agttcagtct ccaccgcttt gggctgtcct gatatttcta tggtccgcaa aggggacct    5100 tcgagggagc acgcgagagg acaaggctgg gacggcgaat ggcctatgga caggcggaaa    5160
gagggaagcc cttcgcaccg cgaaagagtt acgagtgcga catccataga gtcaagccac    5220
atccagcaag cgaggttcga cccgacacac gtgcttgggg ggcaagtcgg gctggcgacg    5280
cggaataggc cattgatagc agaactcagg ttgggccatt ctgtgctgaa tagcggtgac    5340
cgtcgtcggt gaccattgtc ctaatcgtct cgctccatac atccgccacg atgtctcaag    5400
aacttcacca ccggattgat gccgatgtga tcttcctgtc ataaaccata dacgcgagac    5460
gacttcggtc aatggaagcc ttttctcaa ccatcgagaa ctaggccgtt tgtttggtgg    5520
cgaccatcgc caccaaaaaa acaaacgttc gtcgtctaat gcgcgtcttt ttttcctaga    5580
gttcttctag gaaactagaa aagatgcccc agactgcgag tcaccttgct tttgagtgca    5640
attccctaaa accagtactc taatagtttt tcctagaagt ggatctagga aaatttaatt    5700
tttacttcaa aatttagtta gatttcatat atactcattt gaaccagact gtcaatggtt    5760
acgaattagt cactccgtgg atagagtcgc tagacagata aagcaagtag gtatcaacgg    5820
actgaggggc agcacatcta ttgatgctat gccctcccga atggtagacc ggggtcacga    5880
cgttactatg gcgctctggg tgcgagtggc cgaggtctaa atagtcgtta tttggtcggt    5940
cggccttccc ggctcgcgtc ttcaccagga cgttgaaata gcggaggta ggtcagataa     6000 ttaacaacgg cccttcgatc tcattcatca agcggtcaat tatcaaacgc gttgcaacaa    6060
cggtaacgat gtccgtagca ccacagtgcg agcagcaaac cataccgaag taagtcgagg    6120
ccaagggttg ctagttccgc tcaatgtact aggggggtaca acacgttttt tcgccaatcg    6180
aggaagccag gaggctagca acagtcttca ttcaaccggc gtcacaatag tgagtaccaa    6240
taccgtcgtg acgtattaag agaatgacag tacggtaggc attctacgaa aagacactga    6300
ccactcatga gttggttcag taagactctt atcacatacg ccgctggctc aacgagaacg    6360
ggccgcagtt atgccctatt atggcgcggt gtatcgtctt gaaattttca cgagtagtaa    6420 cctttttgcaa gaagccccgc ttttgagagt tcctagaatg gcgacaactc taggtcaagc    6480
```

| | |
|---|---:|
| tacattgggt gagcacgtgg gttgactaga agtcgtagaa aatgaaagtg gtcgcaaaga | 6540 |
| cccactcgtt tttgtccttc cgttttacgg cgttttttcc cttattcccg ctgtgccttt | 6600 |
| acaacttatg agtatgagaa ggaaaaagtt ataataactt cgtaaatagt cccaataaca | 6660 |
| gagtactcgc ctatgtataa acttacataa atctttttat ttgtttatcc ccaaggcgcg | 6720 |
| tgtaaagggg cttttcacgg tggactgcag ctgcctagcc ctctagacga tccactggac | 6780 |
| tccgcgcggc cgaagcttat cggtctcatt ggaaaaaaaa attaaaataa aataaaataa | 6840 |
| aaactctacc tcaaaccgcg gctagagggc taggggatac cagctgagag tcatgttaga | 6900 |
| cgagactacg gcgtatcaat tcggtcatag acgagggacg aacacacaac ctccagcgac | 6960 |
| tcatcacgcg ctcgttttaa attcgatgtt gttccgttcc gaactggctg ttaacgtact | 7020 |
| tcttagacga atcccaatcc gcaaaacgcg acgaagc | 7057 |

<210> SEQ ID NO 3
<211> LENGTH: 467
<212> TYPE: PRT
<213> ORGANISM: Artificial
<220> FEATURE:
<223> OTHER INFORMATION: pD17-20H4.9.h4a amino acid sequence

<400> SEQUENCE: 3

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Ser Pro Glu Lys Gly Leu
    50                  55                  60

Glu Trp Ile Gly Glu Ile Asn His Gly Gly Tyr Val Thr Tyr Asn Pro
65                  70                  75                  80

Ser Leu Glu Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Tyr Gly Pro Gly Asn Tyr Asp Trp Tyr Phe Asp
        115                 120                 125

Leu Trp Gly Arg Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
```

-continued

```
                    260                 265                 270
Ile Ser Arg Thr Pro Glu Val Thr Cys Val Val Asp Val Ser Gln
            275                 280                 285
Glu Asp Pro Glu Val Gln Phe Asn Trp Tyr Val Asp Gly Val Glu Val
        290                 295                 300
His Asn Ala Lys Thr Lys Pro Arg Glu Glu Gln Phe Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Gly Leu Pro Ser Ser Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Gln Glu Glu Met Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Arg Leu Thr Val
            420                 425                 430
Asp Lys Ser Arg Trp Gln Glu Gly Asn Val Phe Ser Cys Ser Val Met
        435                 440                 445
His Glu Ala Leu His Asn His Tyr Thr Gln Lys Ser Leu Ser Leu Ser
    450                 455                 460
Leu Gly Lys
465

<210> SEQ ID NO 4
<211> LENGTH: 6435
<212> TYPE: DNA
<213> ORGANISM: Artificial
<220> FEATURE:
<223> OTHER INFORMATION: pD16gate-20H4.9.LC coding strand

<400> SEQUENCE: 4
gacggatcgg gagatctgct agcccgggtg acctgaggcg cgccggcttc gaatagccag      60
agtaaccttt ttttttaatt ttattttatt ttattttttga gatggagttt ggcgccgatc     120
tcccgatccc ctatggtcga ctctcagtac aatctgctct gatgccgcat agttaagcca     180
gtatctgctc cctgcttgtg tgttggaggt cgctgagtag tgcgcgagca aaatttaagc     240
tacaacaagg caaggcttga ccgacaattg catgaagaat ctgcttaggg ttaggcgttt     300
tgcgctgctt cgcgatgtac gggccagata tacgcgttga cattgattat tgactagtta     360
ttaatagtaa tcaattacgg ggtcattagt tcatagccca tatatggagt tccgcgttac     420
ataacttacg gtaaatggcc cgcctggctg accgcccaac gacccccgcc cattgacgtc     480
aataatgacg tatgttccca tagtaacgcc aatagggact ttccattgac gtcaatgggt     540
ggagtattta cggtaaactg cccacttggc agtacatcaa gtgtatcata tgccaagtac     600
gccccctatt gacgtcaatg acggtaaatg gcccgcctgg cattatgccc agtacatgac     660
cttatgggac tttcctactt ggcagtacat ctacgtatta gtcatcgcta ttaccatggt     720
gatgcggttt tggcagtaca tcaatgggcg tggatagcgg tttgactcac ggggatttcc     780
aagtctccac cccattgacg tcaatgggag tttgttttgg caccaaaatc aacgggactt     840
```

```
tccaaaatgt cgtaacaact ccgccccatt gacgcaaatg ggcggtaggc gtgtacggtg      900
ggaggtctat ataagcagag ctctctggct aactagagaa cccactgctt actggcttat      960
cgaaattaat acgactcact atagggagac ccaagcttat caacaagttt gtacaaaaaa     1020
gcaggctggt accatggaag ccccagctca gcttctcttc ctcctgctac tctggctccc     1080
agataccacc ggagaaattg tgttgacaca gtctccagcc accctgtctt tgtctccagg     1140
ggaaagagcc accctctcct gcagggccag tcagagtgtt agcagctact agcctggta      1200 ccaacagaaa cctggccagg ctcccaggct cctcatctat gatgcatcca acagggccac     1260
tggcatccca gccaggttca gtggcagtgg gtctgggaca gacttcactc tcaccatcag     1320
cagcctagag cctgaagatt ttgcagttta ttactgtcag cagcgtagca actggcctcc     1380
ggcgctcact ttcggcggag ggaccaaggt ggagatcaaa cgtacggtgg ctgcaccatc     1440
tgtcttcatc ttcccgccat ctgatgagca gttgaaatct ggaactgcct ctgttgtgtg     1500
cctgctgaat aacttctatc ccagagaggc caaagtacag tggaaggtgg ataacgccct     1560
ccaatcgggt aactcccagg agagtgtcac agagcaggac agcaaggaca gcacctacag     1620
cctcagcagc accctgacgc tgagcaaagc agactacgag aaacacaaag tctacgcctg     1680
cgaagtcacc catcagggcc tgagctcgcc cgtcacaaag agcttcaaca ggggagagtg     1740
ttagacccag cttcttgta caaagtggtt gatctagagg gcccctattct atagtgtcac     1800 ctaaatgcta gagctcgctg atcagcctcg actgtgcctt ctagttgcca gccatctgtt     1860
gtttgcccct cccccgtgcc ttccttgacc ctggaaggtg ccactcccac tgtcctttcc     1920
taataaaatg aggaaattgc atcgcattgt ctgagtaggt gtcattctat tctggggggt     1980
ggggtggggc aggacagcaa gggggaggat tgggaagaca atagcaggca tgctggggat     2040
gcggtgggct ctatggcttc tgaggcggaa agaaccagct ggggctctag ggggtatccc     2100
cacgcgccct gtagcggcgc attaagcgcg gcgggtgtgg tggttacgcg cagcgtgacc     2160
gctacacttg ccagcgccct agcgcccgct cctttcgctt tcttcccttc ctttctcgcc     2220
acgttcgccg gcctctcaa aaagggaaa aaagcatgc atctcaatta gtcagcaacc     2280
atagtcccgc ccctaactcc gcccatcccg ccctaactc cgcccagttc cgcccattct     2340
ccgccccatg gctgactaat ttttttatt tatgcagagg ccgaggccgc ctcggcctct     2400
gagctattcc agaagtagtg aggaggcttt tttggaggcc taggcttttg caaaaagctt     2460 gggggggacag ctcagggctg cgatttcgcg ccaaacttga cggcaatcct agcgtgaagg     2520
ctggtaggat tttatcccg ctgccatcat ggttcgacca ttgaactgca tcgtcgccgt     2580
gtcccaaaat atggggattg caagaacgg agacctaccc tggcctccgc tcaggaacga     2640
gttcaagtac ttccaaagaa tgaccacaac ctcttcagtg aaggtaaac agaatctggt     2700 gattatgggt aggaaaacct ggttctccat tcctgagaag aatcgacctt taaaggacag     2760
aattaatata gttctcagta gagaactcaa agaaccacca cgaggagctc attttcttgc     2820 caaaagttttg gatgatgcct taagacttat tgaacaaccg gaattggcaa gtaaagtaga     2880
catggtttgg atagtcggag gcagttctgt ttaccaggaa gccatgaatc aaccaggcca     2940
cctcagactc tttgtgacaa ggatcatgca ggaatttgaa agtgacacgt ttttcccaga     3000
aattgatttg gggaaatata aacttctccc agaatacccca ggcgtcctct ctgaggtcca     3060
ggaggaaaaa ggcatcaagt ataagttttga agtctacgag aagaaagact aacaggaaga     3120
tgctttcaag ttctctgctc ccctcctaaa gctatgcatt tttataagac catgggactt     3180
ttgctggctt tagatctgat ctttgtgaag gaaccttact tctgtggtgt gacataattg     3240
```

```
gacaaactac ctacagagat ttaaagctct aaggtaaata taaaattttt aagtgtataa      3300
tgtgttaaac tactgattct aattgtttgt gtattttaga ttccaaccta tggaactgat      3360
gaatgggagc agtggtggaa tgcctttaat gaggaaaacc tgttttgctc agaagaaatg      3420
ccatctagtg atgatgaggc tactgctgac tctcaacatt ctactcctcc aaaaaagaag      3480
agaaaggtag aagaccccaa ggactttcct tcagaattgc taagtttttt gagtcatgct      3540
gtgtttagta atagaactct tgcttgcttt gctatttaca ccacaaagga aaaagctgca      3600
ctgctataca agaaaattat ggaaaaatat tctgtaacct ttataagtag cataacagt       3660 tataatcata acatactgtt ttttcttact ccacacaggc atagagtgtc tgctattaat      3720
aactatgctc aaaaattgtg tacctttagc ttttaatttt gtaaaggggt taataaggaa      3780
tatttgatgt atagtgcctt gactagagat cgatcataat cagccatacc acatttgtag      3840
aggttttact tgcttttaaaa aacctcccac acctccccct gaacctgaaa cataaaatga     3900
atgcaattgt tgttgttaac ttgtttattg cagcttataa tggttacaaa taaagcaata      3960
gcatcacaaa tttcacaaat aaagcatttt tttcactgca ttctagttgt ggtttgtcca      4020
aactcatcaa tgtatcttat catgtctgga tcggctggat gatcctccag cgcggggatc      4080
tcatgctgga gttcttcgcc caccccaact tgtttattgc agcttataat ggttacaaat      4140
aaagcaatag catcacaaat ttcacaaata aagcattttt ttcactgcat tctagttgtg      4200
gtttgtccaa actcatcaat gtatcttatc atgtctgtat accgtcgacc tctagctaga      4260
gcttggcgta atcatggtca tagctgtttc ctgtgtgaaa ttgttatccg ctcacaattc      4320
cacacaacat acgagccgga agcataaagt gtaaagcctg gggtgcctaa tgagtgagct      4380
aactcacatt aattgcgttg cgctcactgc ccgctttcca gtcgggaaac ctgtcgtgcc      4440
agctgcatta atgaatcggc caacgcgcgg ggagaggcgg tttgcgtatt gggcgctctt      4500
ccgcttcctc gctcactgac tcgctgcgct cggtcgttcg gctgcggcga gcggtatcag      4560
ctcactcaaa ggcggtaata cggttatcca cagaatcagg ggataacgca ggaaagaaca      4620
tgtgagcaaa aggccagcaa aaggccagga accgtaaaaa ggccgcgttg ctggcgtttt      4680
tccataggct ccgcccccct gacgagcatc acaaaaatcg acgctcaagt cagaggtggc      4740
gaaacccgac aggactataa agataccagg cgtttccccc tggaagctcc ctcgtgcgct      4800
ctcctgttcc gaccctgccg cttaccggat acctgtccgc ctttctccct tcgggaagcg      4860
tggcgctttc tcatagctca cgctgtaggt atctcagttc ggtgtaggtc gttcgctcca      4920
agctgggctg tgtgcacgaa ccccccgttc agcccgaccg ctgcgcctta ccggtaact       4980 atcgtcttga gtccaacccg gtaagacacg acttatcgcc actggcagca gccactggta      5040
acaggattag cagagcgagg tatgtaggcg gtgctacaga gttcttgaag tggtggccta      5100
actacggcta cactagaagg aacagtattt ggtatctgcg ctctgctgaa gccagttacc      5160
ttcggaaaaa gagttggtag ctcttgatcc ggcaaacaaa ccaccgctgg tagcggtggt      5220
ttttttgttt gcaagcagca gattacgcgc agaaaaaaag gatctcaaga agatcctttg      5280
atcttttcta cggggtctga cgctcagtgg aacgaaaact cacgttaagg gattttggtc      5340
atgagattat caaaaaggat cttcacctag atccttttaa attaaaaatg aagttttaaa      5400
tcaatctaaa gtatatatga gtaaacttgg tctgacagtt accaatgctt aatcagtgag      5460
gcacctatct cagcgatctg tctatttcgt tcatccatag ttgcctgact ccccgtcgtg      5520
tagataacta cgatacggga gggcttacca tctggcccca gtgctgcaat gataccgcga      5580
```

```
gacccacgct caccggctcc agatttatca gcaataaacc agccagccgg aagggccgag    5640
cgcagaagtg gtcctgcaac tttatccgcc tccatccagt ctattaattg ttgccgggaa    5700
gctagagtaa gtagttcgcc agttaatagt ttgcgcaacg ttgttgccat tgctacaggc    5760
atcgtggtgt cacgctcgtc gtttggtatg gcttcattca gctccggttc caacgatca    5820
aggcgagtta catgatcccc catgttgtgc aaaaaagcgg ttagctcctt cggtcctccg    5880
atcgttgtca gaagtaagtt ggccgcagtg ttatcactca tggttatggc agcactgcat    5940
aattctctta ctgtcatgcc atccgtaaga tgcttttctg tgactggtga gtactcaacc    6000
aagtcattct gagaatagtg tatgcggcga ccgagttgct cttgcccggc gtcaatacgg    6060
gataataccg cgccacatag cagaacttta aaagtgctca tcattggaaa acgttcttcg    6120
gggcgaaaac tctcaaggat cttaccgctg ttgagatcca gttcgatgta acccactcgt    6180
gcacccaact gatcttcagc atcttttact ttcaccagcg tttctgggtg agcaaaaaca    6240
ggaaggcaaa atgccgcaaa aaagggaata agggcgacac ggaaatgttg aatactcata    6300
ctcttccttt ttcaatatta ttgaagcatt tatcagggtt attgtctcat gagcggatac    6360
atatttgaat gtatttagaa aaataaacaa ataggggttc cgcgcacatt tccccgaaaa    6420
gtgccacctg acgtc                                                      6435

<210> SEQ ID NO 5
<211> LENGTH: 6435
<212> TYPE: DNA
<213> ORGANISM: Artificial
<220> FEATURE:
<223> OTHER INFORMATION: pD16gate-20H4.9.LC complementary strand

<400> SEQUENCE: 5
ctgcctagcc ctctagacga tcgggcccac tggactccgc gcggccgaag cttatcggtc      60
tcattggaaa aaaaaattaa aataaataa aataaaaact ctacctcaaa ccgcggctag     120
agggctaggg gataccagct gagagtcatg ttagacgaga ctacggcgta tcaattcggt     180
catagacgag ggacgaacac acaacctcca gcgactcatc acgcgctcgt tttaaattcg     240
atgttgttcc gttccgaact ggctgttaac gtacttctta gacgaatccc aatccgcaaa     300
acgcgacgaa gcgctacatg cccggtctat atgcgcaact gtaactaata actgatcaat     360
aattatcatt agttaatgcc ccagtaatca agtatcgggt atatacctca aggcgcaatg     420
tattgaatgc catttaccgg gcggaccgac tggcgggttg ctggggggcgg gtaactgcag     480
ttattactgc atacaagggt atcattgcgg ttatccctga aggtaactg cagttaccca     540
cctcataaat gccatttgac gggtgaaccg tcatgtagtt cacatagtat acggttcatg     600
cgggggataa ctgcagttac tgccatttac cgggcggacc gtaatacggg tcatgtactg     660
gaatacctg aaaggatgaa ccgtcatgta gatgcataat cagtagcgat aatggtacca     720
ctacgccaaa accgtcatgt agttaccgc acctatcgcc aaactgagtg cccctaaagg     780
ttcagaggtg gggtaactgc agttaccctc aaacaaaacc gtggttttag ttgccctgaa     840
aggttttaca gcattgttga ggcggggtaa ctgcgtttac ccgccatccg cacatgccac     900
cctccagata tattcgtctc gagagaccga ttgatctctt gggtgacgaa tgaccgaata     960
gctttaatta tgctgagtga tatccctctg ggttcgaata gttgttcaaa catgtttttt    1020
cgtccgacca tggtaccttc ggggtcgagt cgaagagaag gaggacgatg agaccgaggg    1080
tctatggtgg cctctttaac acaactgtgt cagaggtcgg tggacagaa acagaggtcc    1140
cctttctcgg tgggagagga cgtcccggtc agtctcacaa tcgtcgatga atcggaccat    1200
```

```
ggttgtcttt ggaccggtcc gagggtccga ggagtagata ctacgtaggt tgtcccggtg    1260
accgtagggt cggtccaagt caccgtcacc cagaccctgt ctgaagtgag agtggtagtc    1320
gtcggatctc ggacttctaa aacgtcaaat aatgacagtc gtcgcatcgt tgaccggagg    1380
ccgcgagtga aagccgcctc cctggttcca cctctagttt gcatgccacc gacgtggtag    1440
acagaagtag aagggcggta gactactcgt caactttaga ccttgacgga gacaacacac    1500
ggacgactta ttgaagatag ggtctctccg gtttcatgtc accttccacc tattgcggga    1560
ggttagccca ttgagggtcc tctcacagtg tctcgtcctg tcgttcctgt cgtggatgtc    1620
ggagtcgtcg tgggactgcg actcgtttcg tctgatgctc tttgtgtttc agatgcggac    1680
gcttcagtgg gtagtcccgg actcgagcgg gcagtgtttc tcgaagttgt cccctctcac    1740
aatctgggtc gaaagaacat gtttcaccaa ctagatctcc cgggataaga tatcacagtg    1800
gatttacgat ctcgagcgac tagtcggagc tgacacggaa gatcaacggt cggtagacaa    1860
caaacgggga gggggcacgg aaggaactgg gaccttccac ggtgagggtg acaggaaagg    1920
attattttac tcctttaacg tagcgtaaca gactcatcca cagtaagata agaccccca    1980 ccccaccccg tcctgtcgtt ccccctccta acccttctgt tatcgtccgt acgacccta    2040 cgccacccga gataccgaag actccgcctt tcttggtcga ccccgagatc ccccataggg    2100
gtgcgcggga catcgccgcg taattcgcgc cgcccacacc accaatgcgc gtcgcactgg    2160
cgatgtgaac ggtcgcggga tcgcgggcga ggaaagcgaa agaagggaag gaaagagcgg    2220
tgcaagcggc ccggagagtt tttccctttt ttttcgtacg tagagttaat cagtcgttgg    2280
tatcagggcg gggattgagg cgggtagggc ggggattgag gcgggtcaag gcgggtaaga    2340 ggcgggtac cgactgatta aaaaaaataa atacgtctcc ggctccggcg gagccggaga    2400
ctcgataagg tcttcatcac tcctccgaaa aaacctccgg atccgaaaac gttttttcgaa    2460 cccccctgtc gagtcccgac gctaaagcgc ggtttgaact gccgttagga tcgcacttcc    2520
gaccatccta aaatagggc gacggtagta ccaagctggt aacttgacgt agcagcggca    2580 cagggttta taccctaac cgttcttgcc tctggatggg accggaggcg agtccttgct    2640
caagttcatg aaggtttctt actggtgttg gagaagtcac cttccatttg tcttagacca    2700 ctaatacccca tccttttgga ccaagaggta aggactcttc ttagctggaa atttcctgtc    2760
ttaattatat caagagtcat ctcttgagtt tcttggtggt gctcctcgag taaaagaacg    2820
gttttcaaac ctactacgga attctgaata acttgttggc cttaaccgtt catttcatct    2880
gtaccaaacc tatcagcctc cgtcaagaca aatggtcctt cggtacttag ttggtccggt    2940
ggagtctgag aaacactgtt cctagtacgt ccttaaactt tcactgtgca aaaagggtct    3000
ttaactaaac cctttatat ttgaagaggg tcttatgggt ccgcaggaga gactccaggt    3060
cctccttttt ccgtagttca tattcaaact tcagatgctc ttctttctga ttgtccttct    3120
acgaaagttc aagagacgag gggaggattt cgatacgtaa aaatattctg gtaccctgaa    3180
aacgaccgaa atctagacta gaaacacttc cttggaatga agacaccaca ctgtattaac    3240
ctgtttgatg gatgtctcta aatttcgaga ttccatttat atttttaaaaa ttcacatatt    3300 acacaatttg atgactaaga ttaacaaaca cataaaatct aaggttggat accttgacta    3360
cttaccctcg tcaccacctt acggaaatta ctccttttgg acaaaacgag tcttctttac    3420
ggtagatcac tactactccg atgacgactg agagttgtaa gatgaggagg ttttttcttc    3480
tctttccatc ttctggggtt cctgaaagga agtcttaacg attcaaaaaa ctcagtacga    3540
```

```
cacaaatcat tatcttgaga acgaacgaaa cgataaatgt ggtgtttcct ttttcgacgt    3600
gacgatatgt tcttttaata ccttttata agacattgga aatattcatc cgtattgtca    3660
atattagtat tgtatgacaa aaagaatga ggtgtgtccg tatctcacag acgataatta    3720
ttgatacgag tttttaacac atggaaatcg aaaaattaaa catttcccca attattcctt    3780
ataaactaca tatcacggaa ctgatctcta gctagtatta gtcggtatgg tgtaaacatc    3840
tccaaaatga acgaaatttt ttggagggtg tggagggga cttggacttt gtattttact    3900
tacgttaaca acaacaattg aacaaataac gtcgaatatt accaatgttt atttcgttat    3960
cgtagtgttt aaagtgttta tttcgtaaaa aagtgacgt aagatcaaca ccaaacaggt    4020
ttgagtagtt acatagaata gtacagacct agccgaccta ctaggaggtc gcgccctag    4080 agtacgacct caagaagcgg gtggggttga acaaataacg tcgaatatta ccaatgttta    4140
tttcgttatc gtagtgttta aagtgtttat ttcgtaaaaa aagtgacgta agatcaacac    4200
caaacaggtt tgagtagtta catagaatag tacagacata tggcagctgg agatcgatct    4260
cgaaccgcat tagtaccagt atcgacaaag gacacacttt aacaataggc gagtgttaag    4320
gtgtgttgta tgctcggcct tcgtatttca catttcggac cccacggatt actcactcga    4380
ttgagtgtaa ttaacgcaac gcgagtgacg ggcgaaaggt cagcccttg acagcacgg    4440 tcgacgtaat tacttagccg gttgcgcgcc cctctccgcc aaacgcataa cccgcgagaa    4500
ggcgaaggag cgagtgactg agcgacgcga gccagcaagc cgacgccgct cgccatagtc    4560
gagtgagttt ccgccattat gccaataggt gtcttagtcc cctattgcgt cctttcttgt    4620
acactcgttt tccggtcgtt ttccggtcct tggcatttt ccggcgcaac gaccgcaaaa    4680
aggtatccga ggcggggga ctgctcgtag tgtttttagc tgcgagttca gtctccaccg    4740
ctttgggctg tcctgatatt tctatggtcc gcaaaggggg accttcgagg gagcacgcga    4800
gaggacaagg ctgggacggc gaatggccta tggacaggcg gaaagaggga agcccttcgc    4860
accgcgaaag agtatcgagt gcgacatcca tagagtcaag ccacatccag caagcgaggt    4920
tcgacccgac acacgtgctt ggggggcaag tcgggctggc gacgcggaat aggccattga    4980
tagcagaact caggttgggc cattctgtgc tgaatagcgg tgaccgtcgt cggtgaccat    5040
tgtcctaatc gtctcgctcc atacatccgc cacgatgtct caagaacttc accaccggat    5100
tgatgccgat gtgatcttcc ttgtcataaa ccatagacgc gagacgactt cggtcaatgg    5160 aagcctttt ctcaaccatc gagaactagg ccgtttgttt ggtggcgacc atcgccacca    5220 aaaaacaaa cgttcgtcgt ctaatgcgcg tctttttttc ctagagttct tctaggaaac    5280
tagaaaagat gccccagact gcgagtcacc ttgcttttga gtgcaattcc ctaaaaccag    5340
tactctaata gttttctcta gaagtggatc taggaaaatt taatttttac ttcaaaattt    5400
agttagattt catatatact catttgaacc agactgtcaa tggttacgaa ttagtcactc    5460
cgtggataga gtcgctagac agataaagca agtaggtatc aacggactga ggggcagcac    5520
atctattgat gctatgccct cccgaatggt agaccgggt cacgacgtta ctatggcgct    5580
ctgggtgcga gtggccgagg tctaaatagt cgttatttgg tcggtcggcc ttcccggctc    5640
gcgtcttcac caggacgttg aaataggcgg aggtaggtca gataattaac aacgcccctt    5700
cgatctcatt catcaagcgg tcaattatca aacgcgttgc aacaacggta acgatgtccg    5760
tagcaccaca gtgcgagcag caaaccatac cgaagtaagt cgaggccaag ggttgctagt    5820
tccgctcaat gtactagggg gtacaacacg ttttttcgcc aatcgaggaa gccaggaggc    5880
tagcaacagt cttcattcaa ccggcgtcac aatagtgagt accaataccg tcgtgacgta    5940
```

```
ttaagagaat gacagtacgg taggcattct acgaaaagac actgaccact catgagttgg    6000
ttcagtaaga ctcttatcac atacgccgct ggctcaacga gaacgggccg cagttatgcc    6060
ctattatggc gcggtgtatc gtcttgaaat tttcacgagt agtaaccttt tgcaagaagc    6120
cccgcttttg agagttccta gaatggcgac aactctaggt caagctacat gggtgagca    6180 cgtgggttga ctagaagtcg tagaaaatga aagtggtcgc aaagacccac tcgttttgt    6240 ccttccgttt tacggcgttt tttcccttat tcccgctgtg cctttacaac ttatgagtat    6300
gagaaggaaa aagttataat aacttcgtaa atagtcccaa taacagagta ctcgcctatg    6360
tataaactta cataaatctt tttatttgtt tatccccaag gcgcgtgtaa agggctttt    6420 cacggtggac tgcag                                                     6435
```

<210> SEQ ID NO 6
<211> LENGTH: 236
<212> TYPE: PRT
<213> ORGANISM: Artificial
<220> FEATURE:
<223> OTHER INFORMATION: pD16gate-20H4.9.LC amino acid sequence

<400> SEQUENCE: 6

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Pro Ala Leu Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 7
<211> LENGTH: 1413
<212> TYPE: DNA
<213> ORGANISM: Artificial

<220> FEATURE:
<223> OTHER INFORMATION: 20H4.9-IgG1 coding strand

<400> SEQUENCE: 7

| | |
|---|---|
| atgaaacacc tgtggttctt cctcctcctg gtggcagctc ccagatgggt cctgtcccag | 60 |
| gtgcaactac agcagtgggg cgcaggactg ttgaagcctt cggagaccct gtccctcacc | 120 |
| tgcgctgtct atggtgggtc cttcagtggt tactactgga gctggatacg ccagtcccca | 180 |
| gagaaggggc tggagtggat tgggaaatc aatcatggtg atacgtcac ctacaatccg | 240 |
| tccctcgaga gtcgagtcac catatcagta gacacgtcca agaaccagtt ctccctgaag | 300 |
| ctgagctctg tgaccgccgc ggacacggct gtatattact gtgcgaggga ctatggtccg | 360 |
| gggaattatg actggtactt cgatctctgg ggccgtggca ccctggtcac tgtctcctca | 420 |
| gcctccacca agggcccatc ggtcttcccc ctggcaccct cctccaagag cacctctggg | 480 |
| ggcacagcgg ccctgggctg cctggtcaag gactacttcc ccgaaccggt gacggtgtcg | 540 |
| tggaactcag gcgccctgac cagcggcgtg cacaccttcc cggctgtcct acagtcctca | 600 |
| ggactctact ccctcagcag cgtggtgacc gtgccctcca gcagcttggg cacccagacc | 660 |
| tacatctgca acgtgaatca caagcccagc aacaccaagg tggacaagag agttgagccc | 720 |
| aaatcttgtg acaaaactca cacatgccca ccgtgcccag cacctgaact cctggggga | 780 |
| ccgtcagtct tcctcttccc cccaaaaccc aaggacaccc tcatgatctc ccggacccct | 840 |
| gaggtcacat gcgtggtggt ggacgtgagc cacgaagacc ctgaggtcaa gttcaactgg | 900 |
| tacgtggacg gcgtggaggt gcataatgcc aagacaaagc cgcgggagga gcagtacaac | 960 |
| agcacgtacc gtgtggtcag cgtcctcacc gtcctgcacc aggactggct gaatggcaag | 1020 |
| gagtacaagt gcaaggtctc caacaaagcc ctcccagccc ccatcgagaa aaccatctcc | 1080 |
| aaagccaaag ggcagccccg agaaccacag gtgtacaccc tgcccccatc ccgggatgag | 1140 |
| ctgaccaaga accaggtcag cctgacctgc ctggtcaaag gcttctatcc cagcgacatc | 1200 |
| gccgtggagt gggagagcaa tgggcagccg gagaacaact acaagaccac gcctcccgtg | 1260 |
| ctggactccg acggctcctt cttcctctac agcaagctca ccgtggacaa gagcaggtgg | 1320 |
| cagcagggga acgtcttctc atgctccgtg atgcatgagg ctctgcacaa ccactacacg | 1380 |
| cagaagagcc tctccctgtc cccgggtaaa tga | 1413 |

<210> SEQ ID NO 8
<211> LENGTH: 1413
<212> TYPE: DNA
<213> ORGANISM: Artificial
<220> FEATURE:
<223> OTHER INFORMATION: 20H4.9-IgG1 complementary strand

<400> SEQUENCE: 8

| | |
|---|---|
| tactttgtgg acaccaagaa ggaggaggac caccgtcgag ggtctaccca ggacagggtc | 60 |
| cacgttgatg tcgtcacccc gcgtcctgac aacttcggaa gcctctggga cagggagtgg | 120 |
| acgcgacaga taccacccag gaagtcacca atgatgacct cgacctatgc ggtcagggt | 180 |
| ctcttcccg acctcaccta accccttag ttagtaccac ctatgcagtg gatgttaggc | 240 |
| agggagctct cagctcagtg gtatagtcat ctgtgcaggt tcttggtcaa gagggacttc | 300 |
| gactcgagac actggcggcg cctgtgccga catataatga cacgctccct gataccaggc | 360 |
| cccttaatac tgaccatgaa gctagagacc cggcaccgt gggaccagtg acagaggagt | 420 |
| cggaggtggt tcccgggtag ccagaagggg gaccgtggga ggaggttctc gtggagaccc | 480 |

```
ccgtgtcgcc gggacccgac ggaccagttc ctgatgaagg ggcttggcca ctgccacagc   540
accttgagtc cgcgggactg gtcgccgcac gtgtggaagg gccgacagga tgtcaggagt   600
cctgagatga gggagtcgtc gcaccactgg cacgggaggt cgtcgaaccc gtgggtctgg   660
atgtagacgt tgcacttagt gttcgggtcg ttgtggttcc acctgttctc tcaactcggg   720
tttagaacac tgttttgagt gtgtacgggt ggcacgggtc gtggacttga ggaccccct    780 ggcagtcaga aggagaaggg gggttttggg ttcctgtggg agtactagag gcctggggga   840
ctccagtgta cgcaccacca cctgcactcg gtgcttctgg actccagtt caagttgacc    900 atgcacctgc cgcacctcca cgtattacgg ttctgtttcg gcgccctcct cgtcatgttg   960
tcgtgcatgg cacaccagtc gcaggagtgg caggacgtgg tcctgaccga cttaccgttc  1020
ctcatgttca cgttccagag gttgtttcgg gagggtcggg ggtagctctt ttggtagagg  1080
tttcggtttc ccgtcggggc tcttggtgtc cacatgtggg acgggggtag ggccctactc  1140
gactggttct tggtccagtc ggactggacg gaccagtttc cgaagatagg gtcgctgtag  1200
cggcacctca ccctctcgtt acccgtcggc ctcttgttga tgttctggtg cggagggcac  1260
gacctgaggc tgccgaggaa gaaggagatg tcgttcgagt ggcacctgtt ctcgtccacc  1320 gtcgtccct tgcagaagag tacgaggcac tacgtactcc gagacgtgtt ggtgatgtgc   1380
gtcttctcgg agagggacag gggcccattt act                                1413
```

<210> SEQ ID NO 9
<211> LENGTH: 470
<212> TYPE: PRT
<213> ORGANISM: Artificial
<220> FEATURE:
<223> OTHER INFORMATION: 20H4.9-IgG1 amino acid sequence

<400> SEQUENCE: 9

```
Met Lys His Leu Trp Phe Phe Leu Leu Leu Val Ala Ala Pro Arg Trp
 1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Ser Pro Glu Lys Gly Leu
    50                  55                  60

Glu Trp Ile Gly Glu Ile Asn His Gly Gly Tyr Val Thr Tyr Asn Pro
65                  70                  75                  80

Ser Leu Glu Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Tyr Gly Pro Gly Asn Tyr Asp Trp Tyr Phe Asp
        115                 120                 125

Leu Trp Gly Arg Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
```

-continued

```
            195                 200                 205
Val Thr Val Pro Ser Ser Leu Gly Thr Gln Thr Tyr Ile Cys Asn
        210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465             470
```